US012723263B2

(12) United States Patent
Jauze et al.

(10) Patent No.: US 12,723,263 B2
(45) Date of Patent: Sep. 1, 2026

(54) VECTORS ENCODING A GLUCOSE-6-PHOSPHATASE (G6PASE-A) FOR GENE THERAPY

(71) Applicants: GENETHON, Évry-Courcouronnes (FR); INSTITUT NATIONAL DE LA SANTE ET DE LA RECHERCHE MEDICALE (INSERM), Paris (FR); UNIVERSITE D'EVRY VAL D'ESSONNE, Évry-Courcouronnes (FR); UNIVERSITE CLAUDE BERNARD LYON 1, Villeurbanne (FR)

(72) Inventors: Louisa Jauze, Vitry-sur-Seine (FR); Fabienne Rajas, Salt-en-Donzy (FR); Giuseppe Ronzitti, Fontainebleau (FR)

(73) Assignees: GENETHON, Évry-Courcouronnes (FR); INSTITUT NATIONAL DE LA SANTE ET DE LA RECHERCHE MEDICALE (INSERM), Paris (FR); UNIVERSITE D'EVRY VAL D'ESSONNE, Évry-Courcouronnes (FR); UNIVERSITE CLAUDE BERNARD LYON, Villeurbanne (FR)

( * ) Notice: Subject to any disclaimer, the term of this patent is extended or adjusted under 35 U.S.C. 154(b) by 715 days.

(21) Appl. No.: 17/926,709

(22) PCT Filed: May 21, 2021

(86) PCT No.: PCT/EP2021/063728
§ 371 (c)(1),
(2) Date: Nov. 21, 2022

(87) PCT Pub. No.: WO2021/234176
PCT Pub. Date: Nov. 25, 2021

(65) Prior Publication Data

US 2023/0203534 A1 Jun. 29, 2023

(30) Foreign Application Priority Data

May 22, 2020 (EP) .................................... 20305540

(51) Int. Cl.
*C12N 15/86* (2006.01)
*C07K 14/81* (2006.01)
*C12N 9/16* (2006.01)

(52) U.S. Cl.
CPC .......... *C12N 15/86* (2013.01); *C07K 14/8125* (2013.01); *C12N 9/16* (2013.01); *C12Y 301/03009* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS 10,415,044 B2 * 9/2019 Chou ................. A61K 48/0075

FOREIGN PATENT DOCUMENTS

| | | | | |
|---|---|---|---|---|
| CN | 107636153 A | 1/2018 | | |
| CN | 109843930 A | 6/2019 | | |
| JP | 2004532822 A | 10/2004 | | |
| JP | 2019533990 A | 11/2019 | | |
| JP | 2019533991 A | 11/2019 | | |
| WO | 2002071843 A1 | 9/2002 | | |
| WO | 2015081101 A1 | 6/2015 | | |
| WO | 2015081101 A8 | 6/2015 | | |
| WO | 2016106303 A1 | 6/2016 | | |
| WO | 2018046774 A1 | 3/2018 | | |
| WO | 2018046775 A1 | 3/2018 | | |
| WO | WO-2018129586 A1 * | 7/2018 | ............. | C12N 15/86 |
| WO | WO-2020014209 A1 * | 1/2020 | ............. | C12N 15/88 |

OTHER PUBLICATIONS

Genecards page for G6PC1, Updated Mar. 30, 2025, https://www.genecards.org/cgi-bin/carddisp.pl?gene=G6PC1 (Year: 2025).*
Vector Builder, GC content calculator results for U.S. Pat. No. 10,415,044B2, https://en.vectorbuilder.com/tool/gc-content-calculator.html (Year: 2026).*
Sommer, Birgit (Authorized Officer), International Search Report and Written Opinion of the International Searching Authority for International Application No. PCT/EP2021/063728 mailed Sep. 3, 2021, 11 pages.
Extended European Search Report for European Patent Application No. 20305540.5 dated Oct. 23, 2020, 3 pages.
Grinshpun et al., "Neonatal Gene Therapy of Glycogen Storage Disease Type la Using a Feline Immunodeficiency Virus-based Vector", Molecular Therapy, 2010, vol. 18, No. 9, pp. 1592-1598.
Jauze et al., "Challenges of Gene Therapy for the Treatment of Glycogen Storage Diseases Type I and Type III", Human Gene Therapy, 2019, vol. 30, No. 10, pp. 1263-1273.
Derks, T. G. J., "Positive Cohorts 1 & 2 Results From the Phase 1/2, AAV8-mediated Liver-directed Gene Therapy Trial in Glycogen Storage Disease Type 1a (GSD1a)—First presentation of Cohort 2 data", University of Groningen, 2019, 19 pages.

* cited by examiner

*Primary Examiner* — Allison M Fox
*Assistant Examiner* — Marisol Ann O'Neill
(74) *Attorney, Agent, or Firm* — MH2 Technology Law Group, LLP

(57) ABSTRACT

The invention relates to an adeno-associated virus (AAV) vector comprising a nucleic acid construct for the expression of a glucose-6-phosphatase-a (G6Pase-a) in a cell, the construct comprising a nucleic acid sequence encoding the G6Pase-a, wherein the nucleic acid sequence encoding the G6Pase-a is operably linked to a human alpha-1 antitrypsin (hAAT) promoter, a cell transformed with the vector of the invention, a composition comprising the vector or the cell of the invention, and the use thereof.

22 Claims, 5 Drawing Sheets

Figure 1:
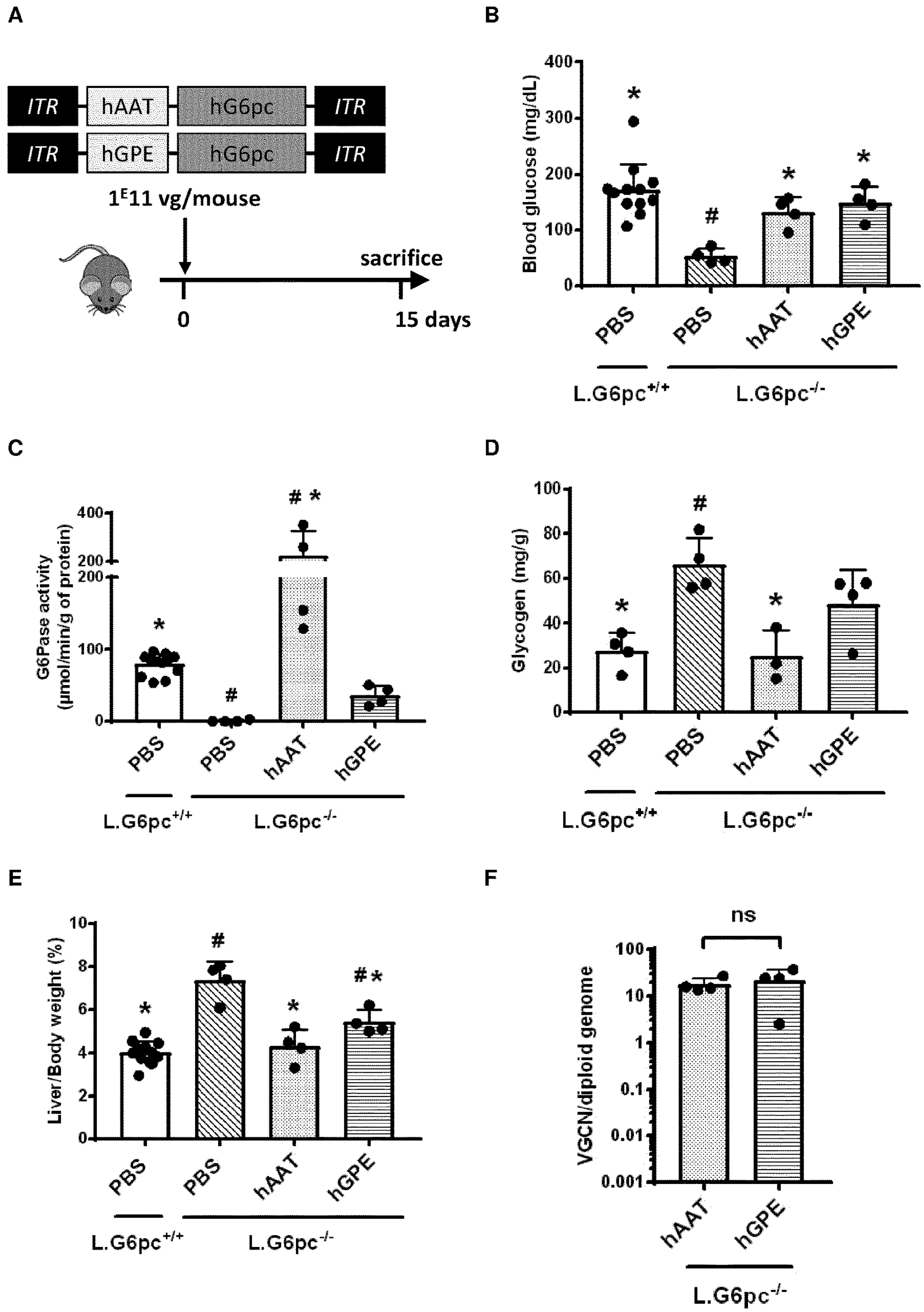

Specification includes a Sequence Listing.

FIGURES

6A

6B

SEQUENCE LISTING

<160> NUMBER OF SEQ ID NOS: 58

<210> SEQ ID NO 1
<211> LENGTH: 357
<212> TYPE: PRT
<213> ORGANISM: Homo sapiens
<220> FEATURE:
<221> NAME/KEY: MISC_FEATURE
<222> LOCATION: (1)..(357)
<223> OTHER INFORMATION: hG6Pase-a wt (amino acid)

<400> SEQUENCE: 1

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350
```

His Lys Lys Ser Leu
355

<210> SEQ ID NO 2
<211> LENGTH: 1074
<212> TYPE: DNA
<213> ORGANISM: Homo sapiens
<220> FEATURE:
<221> NAME/KEY: misc_feature
<222> LOCATION: (1)..(1074)
<223> OTHER INFORMATION: hG6pc wt (nucleic acid) (encoding SEQ ID NO:1)

<400> SEQUENCE: 2
atggaggaag gaatgaatgt tctccatgac tttgggatcc agtcaacaca ttacctccag 60
gtgaattacc aagactccca ggactggttc atcttggtgt ccgtgatcgc agacctcagg 120
aatgccttct acgtcctctt ccccatctgg ttccatcttc aggaagctgt gggcattaaa 180
ctcctttggg tagctgtgat tggagactgg ctcaacctcg tctttaagtg gattctcttt 240
ggacagcgtc catactggtg ggttttggat actgactact acagcaacac ttccgtgccc 300
ctgataaagc agttccctgt aacctgtgag actggaccag ggagcccctc tggccatgcc 360
atgggcacag caggtgtata ctacgtgatg gtcacatcta ctctttccat ctttcaggga 420
aagataaagc cgacctacag atttcggtgc ttgaatgtca ttttgtggtt gggattctgg 480
gctgtgcagc tgaatgtctg tctgtcacga atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagcttcgcc 660
atcggatttt atctgctgct caagggactg ggtgtagacc tcctgtggac tctggagaaa 720
gcccagaggt ggtgcgagca gccagaatgg gtccacattg acaccacacc ctttgccagc 780
ctcctcaaga acctgggcac gctctttggc ctggggctgg ctctcaactc cagcatgtac 840
agggagagct gcaaggggaa actcagcaag tggctcccat tccgcctcag ctctattgta 900
gcctccctcg tcctcctgca cgtctttgac tccttgaaac ccccatccca agtcgagctg 960
gtcttctacg tcttgtcctt ctgcaagagt gcggtagtgc ccctggcatc cgtcagtgtc 1020
atcccctact gcctcgccca ggtcctgggc cagccgcaca agaagtcgtt gtaa 1074

<210> SEQ ID NO 3
<211> LENGTH: 1074
<212> TYPE: DNA
<213> ORGANISM: Artificial Sequence
<220> FEATURE:
<223> OTHER INFORMATION: hG6pc co 3 (nucleic acid) (Codon optimized - encoding SEQ ID NO : 1 used in Example 5)

<400> SEQUENCE: 3
atggaggagg gaatgaatgt gctgcacgac ttcgggattc agtctaccca ctatctccaa 60
gtcaattatc aagacagtca agattggttc atcctcgtct ccgttatagc tgacctcagg 120
aatgcttttt atgtactgtt cccaatatgg tttcatctgc aagaagcagt tggaattaaa 180
ctgctgtggg tggccgtaat cggagactgg ttgaacctgg tgttcaaatg gatccttttt 240
ggtcagaggc catattggtg ggtcttggac accgactatt atagcaacac atctgtaccc 300
ctgataaagc aattccctgt aacgtgtgaa actgggcctg ggtcacccag tggacacgcg 360
atggggactg ccggggttta ctacgtaatg gttactagca cgcttagcat tttccagggc 420
aagatcaaac cgacttatcg cttccgatgc ctcaatgtga tcctctggct gggattctgg 480

-continued

```
gcggttcaac tgaacgtatg cctctcacgg atttatctgg ctgcacattt cccgcatcaa    540

gtagtggctg gtgtgttgtc tggcatagca gtggctgaaa cattctcaca cattcattct    600

atttacaacg cttcattgaa aaaatacttt ctgattactt tttttctttt cagctttgca    660

attggctttt acttgctgct taaaggtctt ggcgtcgacc tgctctggac tcttgagaaa    720

gcgcaacgct ggtgcgaaca acccgagtgg gtccacatag atacgacccc gttcgcgtct    780

cttctgaaaa atctcggtac cctcttcgga ctgggacttg ctttgaattc ttcaatgtat    840

cgggaatcct gcaagggcaa actgtccaag tggttgccct ttcgcctttc aagcattgtc    900

gcttcccttg tgctcctgca cgtcttcgac tcactgaagc cgccgagcca agtcgagctc    960

gtgttttacg tgttgtcttt ctgtaaaagt gccgtcgtgc cactcgccag tgtgagcgtg   1020

ataccttatt gcctcgcaca ggtgcttggg cagcctcata agaagtctct gtaa         1074
```

```
<210> SEQ ID NO 4
<211> LENGTH: 1074
<212> TYPE: DNA
<213> ORGANISM: Artificial Sequence
<220> FEATURE:
<223> OTHER INFORMATION: hG6pc mut (nucleic acid) (identical to SEQ ID
      NO: 2 except for a c >g mutation at position 893) (Encoding SEQ ID
      NO : 12)

<400> SEQUENCE: 4

atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctgtattgta    900

gcctccctcg tcctcctgca cgtctttgac tccttgaaac ccccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa         1074
```

```
<210> SEQ ID NO 5
<211> LENGTH: 1074
<212> TYPE: DNA
<213> ORGANISM: Artificial Sequence
<220> FEATURE:
<223> OTHER INFORMATION: hG6pc mut co (Nucleic acid)(Codon optimized -
      encoding SEQ ID NO : 12)

<400> SEQUENCE: 5
```

-continued

```
atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctgtattgta    900

gcctccctcg tcctcctgca cgtctttgac tccttgaaac ccccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa         1074
```

```
<210> SEQ ID NO 6
<211> LENGTH: 2700
<212> TYPE: DNA
<213> ORGANISM: Artificial Sequence
<220> FEATURE:
<223> OTHER INFORMATION: hGPE promoter (4 nucleotides difference to hGPE
      promoter in NG011808.1)

<400> SEQUENCE: 6

tggaggaagc agaaaggggc tggcaggtgg aaagatgagg accagctcat cgtctcatga     60

ctatgaggtt gctctgatcc agaggtgccc cctgcctggt ggcccaccgc caggaagact    120

cccactgtcc ctggatgccc agagtgggat gtcaactcca tcacttatca actccttatc    180

catagggta ttcttcctga ggcgtctcag aaaacagggc cctccccata tgctgaccac    240

ataatagaac ccctcccaac tcagagaccc tggctgctag ctgccctggc atgacccaga    300

cagtggcctt tgtatatgtt tttagactca ccttgactca cctctgacca tagaaactct    360

catcccagag gtcactgcaa tagttactcc acaacagagg cttatctggg tagagggagg    420

ctccctacct atggcccagc agccctgaca gtgcagatca catatacccc acgccccagc    480

actgcctgcc acgcatgggc ttactttaca cccacccaca gtcaccaaca cattacctgc    540

tctccaaggt taggcgtggc aggagaagtt tgcttggacc agcagaaacc atgcagtcaa    600

ggacaactgg agtcagcatg ggctgggtgc gagcccttgg tggggtgggg aggagactcc    660

aggtcatacc tcctggagga tgttttaatc atttccagca tggaatgctg tcaacttttg    720

ccacagattc attagctctg agtttctttt ttctgtcccc agctacccct tacatgtcaa    780

tatggactta atgatgggaa attcaggcaa gtttttaaac attttattcc ccctggctct    840

tatcctcaaa aaatgcatga atttggaggc agtggctcat gcctgtaatc ccaatgcttt    900

gctaggttga ggcgggagga tcacttgaag ccaggaattt gagaccagcc tgggccgcat    960
```

-continued

```
agtgagaccc cgtttctaca aaaataaata aataaataat aaataatagt gatatgaagc   1020

atgattaaat agccctattt tttaaaatgc atgagttcgt tacctgattc attccctggt   1080

tcctttcaca gtcctccgtg acccaagtgt tagggttttg gtctctctac tatttgtagg   1140

ctgatatata gtatacacac acacacacac acacatatac acacacacag tgtatcttga   1200

gctttctttt gtatatctac acacatatgt ataagaaagc tcaagatata gaagcccttt   1260

ttcaaaaata actgaaagtt tcaaactctt taagtctcca gttaccattt tgctggtatt   1320

cttatttgga accatacatt catcatattg ttgcacagta agactataca ttcattattt   1380

tgcttaaacg tatgagttaa aacacttggc caggcatggt ggttcacacc tgtaatccca   1440

gagctttggg aagccaagac tggcagtact cttgagctca ggaattcaag accagcctgg   1500

gcaacatgga aaaaccccat ctctacaaaa gatagaaaaa ttagccaggc atggtggcgt   1560

gtgcctgtgg tcccagctac tcaggaggct gaggtgggag gatcacatta gcccaggagg   1620

ttgaggctgc agtgagccgt gattatgcca ctgcactcca gcctgggaga cagagtgaga   1680

ccctgtttca aaaaaaagag agagaaaatt taaaaaagaa aacaacacca agggctgtaa   1740

ctttaaggtc attaaatgaa ttaatcactg cattcaaaaa cgattacttt ctggccctaa   1800

gagacatgag gccaatacca ggaagggggt tgatctccca aaccagaggc agaccctaga   1860

ctctaataca gttaaggaaa gaccagcaag atgatagtcc ccaatacaat agaagttact   1920

atattttatt tgttgttttt cttttgtttt gttttgtttt gttttgtttt gttttagaga   1980

ctggggtctt gctcgattgc ccaggctgta gtgcagcggt gggacaatag ctcactgcag   2040

actccaactc ctgggctcaa gcaatcctcc tgcctcagcc tcctgaatag ctgggactac   2100

aagggtacac catcacacac accaaaacaa ttttttaaat ttttgtgtag aaacgagggt   2160

cttgctttgt tgcccaggct ggtctccaac tcctggcttc aagggatcct cccacctcag   2220

cctcccaaat tgctgggatt acaggtgtga gccaccacaa ccagccagaa ctttactaat   2280

tttaaaatta agaacttaaa acttgaatag ctagagcacc aagatttttc tttgtcccca   2340

aataagtgca gttgcaggca tagaaaatct gacatctttg caagaatcat cgtggatgta   2400

gactctgtcc tgtgtctctg gcctggtttc ggggaccagg agggcagacc cttgcactgc   2460

caagaagcat gccaaagtta atcattggcc ctgctgagta catggccgat caggctgttt   2520

ttgtgtgcct gtttttctat tttacgtaaa tcaccctgaa catgtttgca tcaacctact   2580

ggtgatgcac ctttgatcaa tacattttag acaaacgtgg tttttgagtc caaagatcag   2640

ggctgggttg acctgaatac tggatacagg gcatataaaa caggggcaag gcacagactc   2700
```

<210> SEQ ID NO 7
<211> LENGTH: 727
<212> TYPE: DNA
<213> ORGANISM: Artificial Sequence
<220> FEATURE:
<223> OTHER INFORMATION: ApoE enhancer + hAAT promoter

<400> SEQUENCE: 7

```
aggctcagag gcacacagga gtttctgggc tcaccctgcc cccttccaac ccctcagttc     60

ccatcctcca gcagctgttt gtgtgctgcc tctgaagtcc acactgaaca aacttcagcc    120

tactcatgtc cctaaaatgg gcaaacattg caagcagcaa acagcaaaca cacagccctc    180

cctgcctgct gaccttggag ctggggcaga ggtcagagac ctctctgggc ccatgccacc    240

tccaacatcc actcgacccc ttggaatttc ggtggagagg agcagaggtt gtcctggcgt    300

ggtttaggta gtgtgagagg ggtacccggg gatcttgcta ccagtggaac agccactaag    360
```

-continued

```
gattctgcag tgagagcaga gggccagcta agtggtactc tcccagagac tgtctgactc    420

acgccacccc ctccaccttg gacacaggac gctgtggttt ctgagccagg tacaatgact    480

cctttcggta agtgcagtgg aagctgtaca ctgcccaggc aaagcgtccg ggcagcgtag    540

gcgggcgact cagatcccag ccagtggact tagcccctgt ttgctcctcc gataactggg    600

gtgaccttgg ttaatattca ccagcagcct cccccgttgc cctctggat ccactgctta     660

aatacggacg aggacagggc cctgtctcct cagcttcagg caccaccact gacctgggac    720

agtgaat                                                              727
```

```
<210> SEQ ID NO 8
<211> LENGTH: 406
<212> TYPE: DNA
<213> ORGANISM: Artificial Sequence
<220> FEATURE:
<223> OTHER INFORMATION: hAAT promoter

<400> SEQUENCE: 8

gtacccgggg atcttgctac cagtggaaca gccactaagg attctgcagt gagagcagag     60

ggccagctaa gtggtactct cccagagact gtctgactca cgccaccccc tccaccttgg    120

acacaggacg ctgtggtttc tgagccaggt acaatgactc ctttcggtaa gtgcagtgga    180

agctgtacac tgcccaggca aagcgtccgg gcagcgtagg cgggcgactc agatcccagc    240

cagtggactt agcccctgtt tgctcctccg ataactgggg tgaccttggt taatattcac    300

cagcagcctc ccccgttgcc cctctggatc cactgcttaa atacggacga ggacagggcc    360

ctgtctcctc agcttcaggc accaccactg acctgggaca gtgaat                   406
```

```
<210> SEQ ID NO 9
<211> LENGTH: 321
<212> TYPE: DNA
<213> ORGANISM: Artificial Sequence
<220> FEATURE:
<223> OTHER INFORMATION: ApoE enhancer

<400> SEQUENCE: 9

aggctcagag gcacacagga gtttctgggc tcaccctgcc cccttccaac ccctcagttc     60

ccatcctcca gcagctgttt gtgtgctgcc tctgaagtcc acactgaaca aacttcagcc    120

tactcatgtc cctaaaatgg gcaaacattg caagcagcaa acagcaaaca cacagccctc    180

cctgcctgct gaccttggag ctggggcaga ggtcagagac ctctctgggc ccatgccacc    240

tccaacatcc actcgacccc ttggaatttc ggtggagagg agcagaggtt gtcctggcgt    300

ggtttaggta gtgtgagagg g                                              321
```

```
<210> SEQ ID NO 10
<211> LENGTH: 4492
<212> TYPE: DNA
<213> ORGANISM: Artificial Sequence
<220> FEATURE:
<223> OTHER INFORMATION: hGPE_HBB2_hG6pcwt_bGH (expression cassette used
      in examples 1, 2 and 3)

<400> SEQUENCE: 10

tggaggaagc agaaaggggc tggcaggtgg aaagatgagg accagctcat cgtctcatga     60

ctatgaggtt gctctgatcc agaggtgccc cctgcctggt ggcccaccgc caggaagact    120

cccactgtcc ctggatgccc agagtgggat gtcaactcca tcacttatca actccttatc    180

catagggta ttcttcctga ggcgtctcag aaaacagggc cctccccata tgctgaccac     240
```

-continued

```
ataatagaac cctcccaac tcagagaccc tggctgctag ctgccctggc atgacccaga    300
cagtggcctt tgtatatgtt tttagactca ccttgactca cctctgacca tagaaactct    360
catcccagag gtcactgcaa tagttactcc acaacagagg cttatctggg tagagggagg    420
ctccctacct atggcccagc agccctgaca gtgcagatca catataccc acgccccagc    480
actgcctgcc acgcatgggc ttactttaca cccacccaca gtcaccaaca cattacctgc    540
tctccaaggt taggcgtggc aggagaagtt tgcttggacc agcagaaacc atgcagtcaa    600
ggacaactgg agtcagcatg ggctgggtgc gagcccttgg tggggtgggg aggagactcc    660
aggtcatacc tcctggagga tgttttaatc atttccagca tggaatgctg tcaacttttg    720
ccacagattc attagctctg agtttctttt ttctgtcccc agctacccct tacatgtcaa    780
tatggactta atgatgggaa attcaggcaa gtttttaaac attttattcc ccctggctct    840
tatcctcaaa aaatgcatga atttggaggc agtggctcat gcctgtaatc ccaatgcttt    900
gctaggttga ggcgggagga tcacttgaag ccaggaattt gagaccagcc tgggccgcat    960
agtgagaccc cgtttctaca aaaataaata aataaataat aaataatagt gatatgaagc   1020
atgattaaat agccctattt tttaaaatgc atgagttcgt tacctgattc attccctggt   1080
tcctttcaca gtcctccgtg acccaagtgt tagggttttg gtctctctac tatttgtagg   1140
ctgatatata gtatacacac acacacacac acacatatac acacacacag tgtatcttga   1200
gctttctttt gtatatctac acacatatgt ataagaaagc tcaagatata gaagcccttt   1260
ttcaaaaata actgaaagtt tcaaactctt taagtctcca gttaccattt tgctggtatt   1320
cttatttgga accatacatt catcatattg ttgcacagta agactataca ttcattattt   1380
tgcttaaacg tatgagttaa aacacttggc caggcatggt ggttcacacc tgtaatccca   1440
gagctttggg aagccaagac tggcagtact cttgagctca ggaattcaag accagcctgg   1500
gcaacatgga aaaaccccat ctctacaaaa gatagaaaaa ttagccaggc atggtggcgt   1560
gtgcctgtgg tcccagctac tcaggaggct gaggtgggag gatcacatta gcccaggagg   1620
ttgaggctgc agtgagccgt gattatgcca ctgcactcca gcctgggaga cagagtgaga   1680
ccctgtttca aaaaaaagag agagaaaatt taaaaaagaa aacaacacca agggctgtaa   1740
ctttaaggtc attaaatgaa ttaatcactg cattcaaaaa cgattacttt ctggccctaa   1800
gagacatgag gccaatacca ggaagggggt tgatctccca aaccagaggc agaccctaga   1860
ctctaataca gttaaggaaa gaccagcaag atgatagtcc ccaatacaat agaagttact   1920
atattttatt tgttgttttt cttttgtttt gttttgtttt gttttgtttt gttttagaga   1980
ctggggtctt gctcgattgc ccaggctgta gtgcagcggt gggacaatag ctcactgcag   2040
actccaactc ctgggctcaa gcaatcctcc tgcctcagcc tcctgaatag ctgggactac   2100
aagggtacac catcacacac accaaaacaa ttttttaaat ttttgtgtag aaacgagggt   2160
cttgctttgt tgcccaggct ggtctccaac tcctggcttc aagggatcct cccacctcag   2220
cctcccaaat tgctgggatt acaggtgtga gccaccacaa ccagccagaa ctttactaat   2280
tttaaaatta agaacttaaa acttgaatag ctagagcacc aagatttttc tttgtcccca   2340
aataagtgca gttgcaggca tagaaaatct gacatctttg caagaatcat cgtggatgta   2400
gactctgtcc tgtgtctctg gcctggtttc ggggaccagg agggcagacc cttgcactgc   2460
caagaagcat gccaaagtta atcattggcc ctgctgagta catggccgat caggctgttt   2520
ttgtgtgcct gtttttctat tttacgtaaa tcaccctgaa catgtttgca tcaacctact   2580
```

-continued

```
ggtgatgcac ctttgatcaa tacattttag acaaacgtgg tttttgagtc caaagatcag   2640

ggctgggttg acctgaatac tggatacagg gcatataaaa caggggcaag gcacagactc   2700

gggacccttg atgttttctt tccccttctt ttctatggtt aagttcatgt cataggaagg   2760

ggagaagtaa cagggtacac atattgacca aatcagggta attttgcatt tgtaatttta   2820

aaaaatgctt tcttctttta atatactttt ttgtttatct tatttctaat actttcccta   2880

atctctttct ttcagggcaa tattgataca atgtatcttg cctctttgca ccattctaaa   2940

gaataacagt gataatttct gggttaaggc aatagcaata tttctgcata taaatatttc   3000

tgcatataaa ttgtaactga tgtaagaggt ttcatattgc taatagcagc tacaatccag   3060

ctaccattct gcttttattt tctggttggg ataaggctgg attattctga gtccaagcta   3120

ggcccttttg ctaatcttgt tcatacctct tatcttcctc ccacagctcc tgggcaacct   3180

gctggtctct ctgctggccc atcactttgg caaagcacgc gtgccaccat ggaggaagga   3240

atgaatgttc tccatgactt tgggatccag tcaacacatt acctccaggt gaattaccaa   3300

gactcccagg actggttcat cttggtgtcc gtgatcgcag acctcaggaa tgccttctac   3360

gtcctcttcc ccatctggtt ccatcttcag gaagctgtgg gcattaaact cctttgggta   3420

gctgtgattg gagactggct caacctcgtc tttaagtgga ttctctttgg acagcgtcca   3480

tactggtggg ttttggatac tgactactac agcaacactt ccgtgcccct gataaagcag   3540

ttccctgtaa cctgtgagac tggaccaggg agcccctctg gccatgccat gggcacagca   3600

ggtgtatact acgtgatggt cacatctact ctttccatct ttcagggaaa gataaagccg   3660

acctacagat ttcggtgctt gaatgtcatt ttgtggttgg gattctgggc tgtgcagctg   3720

aatgtctgtc tgtcacgaat ctaccttgct gctcattttc ctcatcaagt tgttgctgga   3780

gtcctgtcag gcattgctgt tgcagaaact ttcagccaca tccacagcat ctataatgcc   3840

agcctcaaga aatattttct cattaccttc ttcctgttca gcttcgccat cggattttat   3900

ctgctgctca agggactggg tgtagacctc ctgtggactc tggagaaagc ccagaggtgg   3960

tgcgagcagc cagaatgggt ccacattgac accacaccct ttgccagcct cctcaagaac   4020

ctgggcacgc tctttggcct ggggctggct ctcaactcca gcatgtacag ggagagctgc   4080

aaggggaaac tcagcaagtg gctcccattc cgcctcagct ctattgtagc ctccctcgtc   4140

ctcctgcacg tctttgactc cttgaaaccc ccatcccaag tcgagctggt cttctacgtc   4200

ttgtccttct gcaagagtgc ggtagtgccc ctggcatccg tcagtgtcat cccctactgc   4260

ctcgcccagg tcctgggcca gccgcacaag aagtcgttgt aaagatctga attcaccgcg   4320

ggtttaaact gtgccttcta gttgccagcc atctgttgtt tgcccctccc ccgtgccttc   4380

cttgaccctg gaaggtgcca ctcccactgt cctttcctaa taaaatgagg aaattgcatc   4440

gcattgtctg agtaggtgtc attctattct ggggggtggg gtgggggcta gc           4492
```

<210> SEQ ID NO 11
<211> LENGTH: 3153
<212> TYPE: DNA
<213> ORGANISM: Artificial Sequence
<220> FEATURE:
<223> OTHER INFORMATION: hAAT_HBB2_hG6pc wt (expression cassette used in examples 1, 2, 3, 4 and 5)

<400> SEQUENCE: 11

```
ggatcaaggc tcagaggcac acaggagttt ctgggctcac cctgcccccct tccaacccct     60

cagttcccat cctccagcag ctgtttgtgt gctgcctctg aagtccacac tgaacaaact    120
```

-continued

```
tcagcctact catgtcccta aaatgggcaa acattgcaag cagcaaacag caaacacaca    180
gccctccctg cctgctgacc ttggagctgg ggcagaggtc agagacctct ctgggcccat    240
gccacctcca acatccactc gaccccttgg aatttcggtg gagaggagca gaggttgtcc    300
tggcgtggtt taggtagtgt gagaggggta cccggggatc ttgctaccag tggaacagcc    360
actaaggatt ctgcagtgag agcagagggc cagctaagtg gtactctccc agagactgtc    420
tgactcacgc caccccctcc accttggaca caggacgctg tggtttctga gccaggtaca    480
atgactcctt tcggtaagtg cagtggaagc tgtacactgc ccaggcaaag cgtccgggca    540
gcgtaggcgg gcgactcaga tcccagccag tggacttagc cctgtttgc tcctccgata     600
actggggtga ccttggttaa tattcaccag cagcctcccc cgttgcccct ctggatccac    660
tgcttaaata cggacgagga cagggccctg tctcctcagc ttcaggcacc accactgacc    720
tgggacagtg aatagatcct gagaacttca gggtgagtct atgggaccct tgatgttttc    780
tttccccttc ttttctatgg ttaagttcat gtcataggaa ggggagaagt aacagggtac    840
acatattgac caaatcaggg taattttgca tttgtaattt taaaaaatgc tttcttcttt    900
taatatactt ttttgtttat cttatttcta atactttccc taatctcttt ctttcagggc    960
aatattgata caatgtatct tgcctctttg caccattcta aagaataaca gtgataattt   1020
ctgggttaag gcaatagcaa tatttctgca tataaatatt tctgcatata aattgtaact   1080
gatgtaagag gtttcatatt gctaatagca gctacaatcc agctaccatt ctgcttttat   1140
tttctggttg ggataaggct ggattattct gagtccaagc taggcccttt tgctaatctt   1200
gttcatacct cttatcttcc tcccacagct cctgggcaac ctgctggtct ctctgctggc   1260
ccatcacttt ggcaaagcac gcgtgccacc atggaggaag gaatgaatgt tctccatgac   1320
tttgggatcc agtcaacaca ttacctccag gtgaattacc aagactccca ggactggttc   1380
atcttggtgt ccgtgatcgc agacctcagg aatgccttct acgtcctctt ccccatctgg   1440
ttccatcttc aggaagctgt gggcattaaa ctcctttggg tagctgtgat tggagactgg   1500
ctcaacctcg tctttaagtg gattctcttt ggacagcgtc catactggtg ggttttggat   1560
actgactact acagcaacac ttccgtgccc ctgataaagc agttccctgt aacctgtgag   1620
actggaccag ggagcccctc tggccatgcc atgggcacag caggtgtata ctacgtgatg   1680
gtcacatcta ctctttccat ctttcaggga aagataaagc cgacctacag atttcggtgc   1740
ttgaatgtca ttttgtggtt gggattctgg gctgtgcagc tgaatgtctg tctgtcacga   1800
atctaccttg ctgctcattt tcctcatcaa gttgttgctg gagtcctgtc aggcattgct   1860
gttgcagaaa ctttcagcca catccacagc atctataatg ccagcctcaa gaaatatttt   1920
ctcattacct tcttcctgtt cagcttcgcc atcggatttt atctgctgct caagggactg   1980
ggtgtagacc tcctgtggac tctggagaaa gcccagaggt ggtgcgagca gccagaatgg   2040
gtccacattg acaccacacc ctttgccagc ctcctcaaga acctgggcac gctctttggc   2100
ctggggctgg ctctcaactc cagcatgtac agggagagct gcaaggggaa actcagcaag   2160
tggctcccat tccgcctcag ctctattgta gcctccctcg tcctcctgca cgtctttgac   2220
tccttgaaac ccccatccca agtcgagctg gtcttctacg tcttgtcctt ctgcaagagt   2280
gcggtagtgc ccctggcatc cgtcagtgtc atcccctact gcctcgccca ggtcctgggc   2340
cagccgcaca agaagtcgtt gtaaagatct gaattcaccc caccagtgca ggctgcctat   2400
cagaaagtgg tggctggtgt ggctaatgcc ctggcccaca agtatcacta agctcgcttt   2460
cttgctgtcc aatttctatt aaaggttcct ttgttcccta agtccaacta ctaaactggg   2520
```

```
ggatattatg aagggccttg agcatctgga ttctgcctaa taaaaaacat ttattttcat   2580

tgcaatgatg tatttaaatt atttctgaat attttactaa aaagggaatg tgggaggtca   2640

gtgcatttaa aacataaaga aatgaagagc tagttcaaac cttgggaaaa tacactatat   2700

cttaaactcc atgaaagaag gtgaggctgc aaacagctaa tgcacattgg caacagcccc   2760

tgatgcctat gccttattca tccctcagaa aaggattcaa gtagaggctt gatttggagg   2820

ttaaagtttg gctatgctgt attttacatt acttattgtt ttagctgtcc tcatgaatgt   2880

cttttcacta cccatttgct tatcctgcat ctctcagcct tgactccact cagttctctt   2940

gcttagagat accacctttc ccctgaagtg ttccttccat gttttacggc gagatggttt   3000

ctcctcgcct ggccactcag ccttagttgt ctctgttgtc ttatagaggt ctacttgaag   3060

aaggaaaaac agggggcatg gtttgactgt cctgtgagcc cttcttccct gcctccccca   3120

ctcacagtga cccggaatcc ctcgacatgg cag                                  3153
```

<210> SEQ ID NO 12
<211> LENGTH: 357
<212> TYPE: PRT
<213> ORGANISM: Artificial Sequence
<220> FEATURE:
<223> OTHER INFORMATION: hG6Pase-a mut (amino acid)

<400> SEQUENCE: 12

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
```

```
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Cys Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355
```

<210> SEQ ID NO 13
<211> LENGTH: 1074
<212> TYPE: DNA
<213> ORGANISM: Artificial Sequence
<220> FEATURE:
<223> OTHER INFORMATION: Nucleic acid coding modified G6Pase-a (R3K)

<400> SEQUENCE: 13

```
atggagaaag gaatgaatgt tctccatgac tttgggatcc agtcaacaca ttacctccag      60

gtgaattacc aagactccca ggactggttc atcttggtgt ccgtgatcgc agacctcagg     120

aatgccttct acgtcctctt ccccatctgg ttccatcttc aggaagctgt gggcattaaa     180

ctcctttggg tagctgtgat tggagactgg ctcaacctcg tctttaagtg gattctcttt     240

ggacagcgtc catactggtg ggttttggat actgactact acagcaacac ttccgtgccc     300

ctgataaagc agttccctgt aacctgtgag actggaccag ggagcccctc tggccatgcc     360

atgggcacag caggtgtata ctacgtgatg gtcacatcta ctctttccat ctttcaggga     420

aagataaagc cgacctacag atttcggtgc ttgaatgtca ttttgtggtt gggattctgg     480

gctgtgcagc tgaatgtctg tctgtcacga atctaccttg ctgctcattt tcctcatcaa     540

gttgttgctg gagtcctgtc aggcattgct gttgcagaaa ctttcagcca catccacagc     600

atctataatg ccagcctcaa gaaatatttt ctcattacct tcttcctgtt cagcttcgcc     660

atcggatttt atctgctgct caagggactg ggtgtagacc tcctgtggac tctggagaaa     720

gcccagaggt ggtgcgagca gccagaatgg gtccacattg acaccacacc ctttgccagc     780

ctcctcaaga acctgggcac gctctttggc ctggggctgg ctctcaactc cagcatgtac     840

agggagagct gcaaggggaa actcagcaag tggctcccat tccgcctcag ctctattgta     900

gcctccctcg tcctcctgca cgtctttgac tccttgaaac ccccatccca agtcgagctg     960

gtcttctacg tcttgtcctt ctgcaagagt gcggtagtgc ccctggcatc cgtcagtgtc    1020

atcccctact gcctcgccca ggtcctgggc cagccgcaca agaagtcgtt gtaa          1074
```

<210> SEQ ID NO 14
<211> LENGTH: 1074
<212> TYPE: DNA
<213> ORGANISM: Artificial Sequence
<220> FEATURE:
<223> OTHER INFORMATION: Nucleic acid coding modified G6Pase-a (Q54R)

<400> SEQUENCE: 14

-continued

```
atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc gtgaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac cccatccca agtcgagctg     960

gtcttctacg tcttgtcctt ctgcaagagt gcggtagtgc cctggcatc cgtcagtgtc    1020

atcccctact gcctcgccca ggtcctgggc cagccgcaca agaagtcgtt gtaa         1074


<210> SEQ ID NO 15
<211> LENGTH: 1074
<212> TYPE: DNA
<213> ORGANISM: Artificial Sequence
<220> FEATURE:
<223> OTHER INFORMATION: Nucleic acid coding modified G6Pase-a (Q139R)

<400> SEQUENCE: 15

atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcgggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac cccatccca agtcgagctg     960

gtcttctacg tcttgtcctt ctgcaagagt gcggtagtgc cctggcatc cgtcagtgtc    1020
```

-continued

```
atcccctact gcctcgccca ggtcctgggc cagccgcaca agaagtcgtt gtaa        1074


<210> SEQ ID NO 16
<211> LENGTH: 1074
<212> TYPE: DNA
<213> ORGANISM: Artificial Sequence
<220> FEATURE:
<223> OTHER INFORMATION: Nucleic acid coding modified G6Pase-a (I142K)

<400> SEQUENCE: 16

atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagaaaaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac ccccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa        1074


<210> SEQ ID NO 17
<211> LENGTH: 1074
<212> TYPE: DNA
<213> ORGANISM: Artificial Sequence
<220> FEATURE:
<223> OTHER INFORMATION: Nucleic acid coding modified G6Pase-a (S196R)

<400> SEQUENCE: 17

atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttccgcca catccacagc    600
```

-continued

```
atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac cccatccca agtcgagctg    960

gtcttctacg tcttgtcctt ctgcaagagt gcggtagtgc cctggcatc cgtcagtgtc   1020

atccccctact gcctcgccca ggtcctgggc cagccgcaca agaagtcgtt gtaa        1074
```

<210> SEQ ID NO 18
<211> LENGTH: 1074
<212> TYPE: DNA
<213> ORGANISM: Artificial Sequence
<220> FEATURE:
<223> OTHER INFORMATION: Nucleic acid coding modified G6Pase-a (H199Q)

<400> SEQUENCE: 18

```
atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccagagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac cccatccca agtcgagctg    960

gtcttctacg tcttgtcctt ctgcaagagt gcggtagtgc cctggcatc cgtcagtgtc   1020

atccccctact gcctcgccca ggtcctgggc cagccgcaca agaagtcgtt gtaa        1074
```

<210> SEQ ID NO 19
<211> LENGTH: 1074
<212> TYPE: DNA
<213> ORGANISM: Artificial Sequence
<220> FEATURE:
<223> OTHER INFORMATION: Nucleic acid coding modified G6Pase-a (Q242R)

<400> SEQUENCE: 19

```
atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240
```

-continued

```
ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gccaggaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac ccccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa         1074
```

<210> SEQ ID NO 20
<211> LENGTH: 1074
<212> TYPE: DNA
<213> ORGANISM: Artificial Sequence
<220> FEATURE:
<223> OTHER INFORMATION: Nucleic acid coding modified G6Pase-a (Q247R)

<400> SEQUENCE: 20

```
atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagcg gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac ccccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa         1074
```

<210> SEQ ID NO 21
<211> LENGTH: 1074
<212> TYPE: DNA

<213> ORGANISM: Artificial Sequence
<220> FEATURE:
<223> OTHER INFORMATION: Nucleic acid coding modified G6Pase-a (L292F)

<400> SEQUENCE: 21
atggaggaag gaatgaatgt tctccatgac tttgggatcc agtcaacaca ttacctccag 60
gtgaattacc aagactccca ggactggttc atcttggtgt ccgtgatcgc agacctcagg 120
aatgccttct acgtcctctt ccccatctgg ttccatcttc aggaagctgt gggcattaaa 180
ctcctttggg tagctgtgat tggagactgg ctcaacctcg tctttaagtg gattctcttt 240
ggacagcgtc catactggtg ggttttggat actgactact acagcaacac ttccgtgccc 300
ctgataaagc agttccctgt aacctgtgag actggaccag ggagcccctc tggccatgcc 360
atgggcacag caggtgtata ctacgtgatg gtcacatcta ctctttccat ctttcaggga 420
aagataaagc cgacctacag atttcggtgc ttgaatgtca ttttgtggtt gggattctgg 480
gctgtgcagc tgaatgtctg tctgtcacga atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagcttcgcc 660
atcggatttt atctgctgct caagggactg ggtgtagacc tcctgtggac tctggagaaa 720
gcccagaggt ggtgcgagca gccagaatgg gtccacattg acaccacacc ctttgccagc 780
ctcctcaaga acctgggcac gctctttggc ctggggctgg ctctcaactc cagcatgtac 840
agggagagct gcaaggggaa actcagcaag tggttcccat tccgcctcag ctctattgta 900
gcctccctcg tcctcctgca cgtctttgac tccttgaaac cccatccca agtcgagctg 960 gtcttctacg tcttgtcctt ctgcaagagt gcggtagtgc ccctggcatc cgtcagtgtc 1020
atcccctact gcctcgccca ggtcctgggc cagccgcaca agaagtcgtt gtaa 1074

<210> SEQ ID NO 22
<211> LENGTH: 1074
<212> TYPE: DNA
<213> ORGANISM: Artificial Sequence
<220> FEATURE:
<223> OTHER INFORMATION: Nucleic acid coding modified G6Pase-a (S298C)

<400> SEQUENCE: 22
atggaggaag gaatgaatgt tctccatgac tttgggatcc agtcaacaca ttacctccag 60
gtgaattacc aagactccca ggactggttc atcttggtgt ccgtgatcgc agacctcagg 120
aatgccttct acgtcctctt ccccatctgg ttccatcttc aggaagctgt gggcattaaa 180
ctcctttggg tagctgtgat tggagactgg ctcaacctcg tctttaagtg gattctcttt 240
ggacagcgtc catactggtg ggttttggat actgactact acagcaacac ttccgtgccc 300
ctgataaagc agttccctgt aacctgtgag actggaccag ggagcccctc tggccatgcc 360
atgggcacag caggtgtata ctacgtgatg gtcacatcta ctctttccat ctttcaggga 420
aagataaagc cgacctacag atttcggtgc ttgaatgtca ttttgtggtt gggattctgg 480
gctgtgcagc tgaatgtctg tctgtcacga atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagcttcgcc 660
atcggatttt atctgctgct caagggactg ggtgtagacc tcctgtggac tctggagaaa 720
gcccagaggt ggtgcgagca gccagaatgg gtccacattg acaccacacc ctttgccagc 780
ctcctcaaga acctgggcac gctctttggc ctggggctgg ctctcaactc cagcatgtac 840

```
agggagagct gcaaggggaa actcagcaag tggctcccat tccgcctcag ctgcattgta    900

gcctccctcg tcctcctgca cgtctttgac tccttgaaac cccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa         1074


<210> SEQ ID NO 23
<211> LENGTH: 1074
<212> TYPE: DNA
<213> ORGANISM: Artificial Sequence
<220> FEATURE:
<223> OTHER INFORMATION: Nucleic acid coding modified G6Pase-a (A301V)

<400> SEQUENCE: 23

atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gtgtccctcg tcctcctgca cgtctttgac tccttgaaac cccatccca agtcgagctg    960

gtcttctacg tcttgtcctt ctgcaagagt gcggtagtgc ccctggcatc cgtcagtgtc   1020

atcccctact gcctcgccca ggtcctgggc cagccgcaca agaagtcgtt gtaa         1074


<210> SEQ ID NO 24
<211> LENGTH: 1074
<212> TYPE: DNA
<213> ORGANISM: Artificial Sequence
<220> FEATURE:
<223> OTHER INFORMATION: Nucleic acid coding modified G6Pase-a (V318T)

<400> SEQUENCE: 24

atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420
```

```
aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac ccccatccca aactgagctg    960

gtcttctacg tcttgtcctt ctgcaagagt gcggtagtgc cctggcatcc cgtcagtgtc   1020

atcccctact gcctcgccca ggtcctgggc cagccgcaca agaagtcgtt gtaa         1074
```

<210> SEQ ID NO 25
<211> LENGTH: 1074
<212> TYPE: DNA
<213> ORGANISM: Artificial Sequence
<220> FEATURE:
<223> OTHER INFORMATION: Nucleic acid coding modified G6Pase-a (V324T)

<400> SEQUENCE: 25

```
atggaggaag gaatgaatgt tctccatgac tttgggatcc agtcaacaca ttacctccag     60

gtgaattacc aagactccca ggactggttc atcttggtgt ccgtgatcgc agacctcagg    120

aatgccttct acgtcctctt ccccatctgg ttccatcttc aggaagctgt gggcattaaa    180

ctcctttggg tagctgtgat tggagactgg ctcaacctcg tctttaagtg gattctcttt    240

ggacagcgtc catactggtg ggttttggat actgactact acagcaacac ttccgtgccc    300

ctgataaagc agttccctgt aacctgtgag actggaccag ggagcccctc tggccatgcc    360

atgggcacag caggtgtata ctacgtgatg gtcacatcta ctctttccat ctttcaggga    420

aagataaagc cgacctacag atttcggtgc ttgaatgtca ttttgtggtt gggattctgg    480

gctgtgcagc tgaatgtctg tctgtcacga atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagcttcgcc    660

atcggatttt atctgctgct caagggactg ggtgtagacc tcctgtggac tctggagaaa    720

gcccagaggt ggtgcgagca gccagaatgg gtccacattg acaccacacc ctttgccagc    780

ctcctcaaga acctgggcac gctctttggc ctggggctgg ctctcaactc cagcatgtac    840

agggagagct gcaaggggaa actcagcaag tggctcccat tccgcctcag ctctattgta    900

gcctccctcg tcctcctgca cgtctttgac tccttgaaac ccccatccca agtcgagctg    960

gtcttctaca ccttgtcctt ctgcaagagt gcggtagtgc cctggcatcc cgtcagtgtc   1020

atcccctact gcctcgccca ggtcctgggc cagccgcaca agaagtcgtt gtaa         1074
```

<210> SEQ ID NO 26
<211> LENGTH: 1074
<212> TYPE: DNA
<213> ORGANISM: Artificial Sequence
<220> FEATURE:
<223> OTHER INFORMATION: Nucleic acid coding modified G6Pase-a (V332A)

<400> SEQUENCE: 26

```
atggaggaag gaatgaatgt tctccatgac tttgggatcc agtcaacaca ttacctccag     60
```

gtgaattacc aagactccca ggactggttc atcttggtgt ccgtgatcgc agacctcagg 120
aatgccttct acgtcctctt ccccatctgg ttccatcttc aggaagctgt gggcattaaa 180
ctcctttggg tagctgtgat tggagactgg ctcaacctcg tctttaagtg gattctcttt 240
ggacagcgtc catactggtg ggttttggat actgactact acagcaacac ttccgtgccc 300
ctgataaagc agttccctgt aacctgtgag actggaccag ggagcccctc tggccatgcc 360
atgggcacag caggtgtata ctacgtgatg gtcacatcta ctctttccat ctttcaggga 420
aagataaagc cgacctacag atttcggtgc ttgaatgtca ttttgtggtt gggattctgg 480
gctgtgcagc tgaatgtctg tctgtcacga atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagcttcgcc 660
atcggatttt atctgctgct caagggactg ggtgtagacc tcctgtggac tctggagaaa 720
gcccagaggt ggtgcgagca gccagaatgg gtccacattg acaccacacc ctttgccagc 780
ctcctcaaga acctgggcac gctctttggc ctggggctgg ctctcaactc cagcatgtac 840
agggagagct gcaaggggaa actcagcaag tggctcccat tccgcctcag ctctattgta 900
gcctccctcg tcctcctgca cgtctttgac tccttgaaac cccatccca agtcgagctg 960 gtcttctacg tcttgtcctt ctgcaagagt gcggcagtgc ccctggcatc cgtcagtgtc 1020
atcccctact gcctcgccca ggtcctgggc cagccgcaca agaagtcgtt gtaa 1074

<210> SEQ ID NO 27
<211> LENGTH: 1074
<212> TYPE: DNA
<213> ORGANISM: Artificial Sequence
<220> FEATURE:
<223> OTHER INFORMATION: Nucleic acid coding modified G6Pase-a (Q347R)

<400> SEQUENCE: 27
atggaggaag gaatgaatgt tctccatgac tttgggatcc agtcaacaca ttacctccag 60
gtgaattacc aagactccca ggactggttc atcttggtgt ccgtgatcgc agacctcagg 120
aatgccttct acgtcctctt ccccatctgg ttccatcttc aggaagctgt gggcattaaa 180
ctcctttggg tagctgtgat tggagactgg ctcaacctcg tctttaagtg gattctcttt 240
ggacagcgtc catactggtg ggttttggat actgactact acagcaacac ttccgtgccc 300
ctgataaagc agttccctgt aacctgtgag actggaccag ggagcccctc tggccatgcc 360
atgggcacag caggtgtata ctacgtgatg gtcacatcta ctctttccat ctttcaggga 420
aagataaagc cgacctacag atttcggtgc ttgaatgtca ttttgtggtt gggattctgg 480
gctgtgcagc tgaatgtctg tctgtcacga atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagcttcgcc 660
atcggatttt atctgctgct caagggactg ggtgtagacc tcctgtggac tctggagaaa 720
gcccagaggt ggtgcgagca gccagaatgg gtccacattg acaccacacc ctttgccagc 780
ctcctcaaga acctgggcac gctctttggc ctggggctgg ctctcaactc cagcatgtac 840
agggagagct gcaaggggaa actcagcaag tggctcccat tccgcctcag ctctattgta 900
gcctccctcg tcctcctgca cgtctttgac tccttgaaac cccatccca agtcgagctg 960 gtcttctacg tcttgtcctt ctgcaagagt gcggtagtgc ccctggcatc cgtcagtgtc 1020

-continued atcccctact gcctcgcccg ggtcctgggc cagccgcaca agaagtcgtt gtaa 1074

<210> SEQ ID NO 28
<211> LENGTH: 1074
<212> TYPE: DNA
<213> ORGANISM: Artificial Sequence
<220> FEATURE:
<223> OTHER INFORMATION: Nucleic acid coding modified G6Pase-a (L349F)

<400> SEQUENCE: 28
atggaggaag gaatgaatgt tctccatgac tttgggatcc agtcaacaca ttacctccag 60
gtgaattacc aagactccca ggactggttc atcttggtgt ccgtgatcgc agacctcagg 120
aatgccttct acgtcctctt ccccatctgg ttccatcttc aggaagctgt gggcattaaa 180
ctcctttggg tagctgtgat tggagactgg ctcaacctcg tctttaagtg gattctcttt 240
ggacagcgtc catactggtg ggttttggat actgactact acagcaacac ttccgtgccc 300
ctgataaagc agttccctgt aacctgtgag actggaccag ggagcccctc tggccatgcc 360
atgggcacag caggtgtata ctacgtgatg gtcacatcta ctctttccat ctttcaggga 420
aagataaagc cgacctacag atttcggtgc ttgaatgtca ttttgtggtt gggattctgg 480
gctgtgcagc tgaatgtctg tctgtcacga atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagcttcgcc 660
atcggatttt atctgctgct caagggactg ggtgtagacc tcctgtggac tctggagaaa 720
gcccagaggt ggtgcgagca gccagaatgg gtccacattg acaccacacc ctttgccagc 780
ctcctcaaga acctgggcac gctctttggc ctggggctgg ctctcaactc cagcatgtac 840
agggagagct gcaaggggaa actcagcaag tggctcccat tccgcctcag ctctattgta 900
gcctccctcg tcctcctgca cgtctttgac tccttgaaac cccatcccca agtcgagctg 960
gtcttctacg tcttgtcctt ctgcaagagt gcggtagtgc ccctggcatc cgtcagtgtc 1020
atcccctact gcctcgccca ggtcttcggc cagccgcaca agaagtcgtt gtaa 1074

<210> SEQ ID NO 29
<211> LENGTH: 357
<212> TYPE: PRT
<213> ORGANISM: Artificial Sequence
<220> FEATURE:
<223> OTHER INFORMATION: Modified G6Pase-a (R3K)

<400> SEQUENCE: 29

Met Glu Lys Gly Met Asn Val Leu His Asp Phe Gly Ile Gln Ser Thr
1 5 10 15

His Tyr Leu Gln Val Asn Tyr Gln Asp Ser Gln Asp Trp Phe Ile Leu
20 25 30

Val Ser Val Ile Ala Asp Leu Arg Asn Ala Phe Tyr Val Leu Phe Pro
35 40 45

Ile Trp Phe His Leu Gln Glu Ala Val Gly Ile Lys Leu Leu Trp Val
50 55 60

Ala Val Ile Gly Asp Trp Leu Asn Leu Val Phe Lys Trp Ile Leu Phe
65 70 75 80

Gly Gln Arg Pro Tyr Trp Trp Val Leu Asp Thr Asp Tyr Tyr Ser Asn
85 90 95

Thr Ser Val Pro Leu Ile Lys Gln Phe Pro Val Thr Cys Glu Thr Gly
100 105 110

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 30
<211> LENGTH: 357
<212> TYPE: PRT
<213> ORGANISM: Artificial Sequence
<220> FEATURE:
<223> OTHER INFORMATION: Modified G6Pase-a (Q54R)

<400> SEQUENCE: 30

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Arg Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355
```

<210> SEQ ID NO 31
<211> LENGTH: 357
<212> TYPE: PRT
<213> ORGANISM: Artificial Sequence
<220> FEATURE:
<223> OTHER INFORMATION: Modified G6Pase-a (Q139R)

<400> SEQUENCE: 31

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Arg Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 32
<211> LENGTH: 357
<212> TYPE: PRT
<213> ORGANISM: Artificial Sequence
<220> FEATURE:
<223> OTHER INFORMATION: Modified G6Pase-a (I142K)

<400> SEQUENCE: 32

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Lys Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 33
<211> LENGTH: 357
<212> TYPE: PRT
<213> ORGANISM: Artificial Sequence
<220> FEATURE:
<223> OTHER INFORMATION: Modified G6Pase-a (S196R)

<400> SEQUENCE: 33

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Arg His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 34
<211> LENGTH: 357
<212> TYPE: PRT
<213> ORGANISM: Artificial Sequence
<220> FEATURE:
<223> OTHER INFORMATION: Modified G6Pase-a (H199Q)

<400> SEQUENCE: 34

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile Gln Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 35
<211> LENGTH: 357
<212> TYPE: PRT
<213> ORGANISM: Artificial Sequence
<220> FEATURE:
<223> OTHER INFORMATION: Modified G6Pase-a (Q242R)

<400> SEQUENCE: 35

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Arg Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 36
<211> LENGTH: 357
<212> TYPE: PRT
<213> ORGANISM: Artificial Sequence
<220> FEATURE:
<223> OTHER INFORMATION: Modified G6Pase-a (Q247R)

<400> SEQUENCE: 36

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Arg Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 37
<211> LENGTH: 357
<212> TYPE: PRT
<213> ORGANISM: Artificial Sequence
<220> FEATURE:
<223> OTHER INFORMATION: Modified G6Pase-a (L292F)

<400> SEQUENCE: 37

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Phe Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 38
<211> LENGTH: 357
<212> TYPE: PRT
<213> ORGANISM: Artificial Sequence
<220> FEATURE:
<223> OTHER INFORMATION: Modified G6Pase-a (S298C)

<400> SEQUENCE: 38

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Cys Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 39
<211> LENGTH: 357
<212> TYPE: PRT
<213> ORGANISM: Artificial Sequence
<220> FEATURE:
<223> OTHER INFORMATION: Modified G6Pase-a (A301V)

<400> SEQUENCE: 39

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Val Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 40
<211> LENGTH: 357
<212> TYPE: PRT
<213> ORGANISM: Artificial Sequence
<220> FEATURE:
<223> OTHER INFORMATION: Modified G6Pase-a (V318T)

<400> SEQUENCE: 40

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Thr Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 41
<211> LENGTH: 357
<212> TYPE: PRT
<213> ORGANISM: Artificial Sequence
<220> FEATURE:
<223> OTHER INFORMATION: Modified G6Pase-a (V324T)

<400> SEQUENCE: 41

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Thr Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355


<210> SEQ ID NO 42
<211> LENGTH: 357
<212> TYPE: PRT
<213> ORGANISM: Artificial Sequence
<220> FEATURE:
<223> OTHER INFORMATION: Modified G6Pase-a (V332A)

<400> SEQUENCE: 42

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Ala Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355
```

<210> SEQ ID NO 43
<211> LENGTH: 357
<212> TYPE: PRT
<213> ORGANISM: Artificial Sequence
<220> FEATURE:
<223> OTHER INFORMATION: Modified G6Pase-a (Q347R)

<400> SEQUENCE: 43

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110
```

-continued

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Arg Val Leu Gly Gln Pro
            340                 345                 350

His Lys Lys Ser Leu
        355

<210> SEQ ID NO 44
<211> LENGTH: 357
<212> TYPE: PRT
<213> ORGANISM: Artificial Sequence
<220> FEATURE:
<223> OTHER INFORMATION: Modified G6Pase-a (L349F)

<400> SEQUENCE: 44

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

```
Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Phe Gly Gln Pro
            340                 345                 350

His Lys Lys Ser Leu
        355
```

<210> SEQ ID NO 45
<211> LENGTH: 1074
<212> TYPE: DNA
<213> ORGANISM: Artificial Sequence
<220> FEATURE:
<223> OTHER INFORMATION: Codon optimised G6pc (co1) used in example 5

<400> SEQUENCE: 45

```
atggaggaag gaatgaatgt tctccatgac tttgggatcc agtcaacaca ttacctccag     60

gtgaattacc aagactccca ggactggttc atcttggtgt ctgtgattgc agacctcagg    120

aatgccttct atgtcctctt ccccatctgg ttccatcttc aggaagctgt gggcattaaa    180

ctcctttggg tagctgtgat tggagactgg ctcaacctgg tctttaagtg gattctcttt    240

ggacagaggc catactggtg ggttttggat actgactact acagcaacac ttctgtgccc    300

ctgataaagc agttccctgt aacctgtgag actggaccag ggagcccctc tggccatgcc    360

atgggcacag caggtgtata ctatgtgatg gtcacatcta ctctttccat ctttcaggga    420

aagataaagc ccacctacag atttaggtgc ttgaatgtca ttttgtggtt gggattctgg    480

gctgtgcagc tgaatgtctg tctgtcaagg atctaccttg ctgctcattt tcctcatcaa    540

gttgttgctg gagtcctgtc aggcattgct gttgcagaaa ctttcagcca catccacagc    600

atctataatg ccagcctcaa gaaatatttt ctcattacct tcttcctgtt cagctttgcc    660
```

```
attggatttt atctgctgct caagggactg ggtgtagacc tcctgtggac tctggagaaa    720
gcccagaggt ggtgtgagca gccagaatgg gtccacattg acaccacacc ctttgccagc    780
ctcctcaaga acctgggcac cctctttggc ctggggctgg ctctcaactc cagcatgtac    840
agggagagct gcaaggggaa actcagcaag tggctcccat tcaggctcag ctctattgta    900
gcctccctgg tcctcctgca tgtctttgac tccttgaaac ccccatccca agtggagctg    960
gtcttctatg tcttgtcctt ctgcaagagt gctgtagtgc ccctggcatc tgtcagtgtc   1020
atcccctact gcctggccca ggtcctgggc cagccccaca agaagtcctt gtaa         1074
```

<210> SEQ ID NO 46
<211> LENGTH: 1074
<212> TYPE: DNA
<213> ORGANISM: Artificial Sequence
<220> FEATURE:
<223> OTHER INFORMATION: Codon optimised G6pc (co2) used in example 5

<400> SEQUENCE: 46

```
atggaggagg ggatgaacgt gctgcacgac tttgggatcc agagcaccca ctacctgcag     60
gtgaactacc aggacagcca ggactggttt atcctggtgt ctgtgattgc tgacctgagg    120
aacgccttct acgtgctgtt ccctatctgg ttccacctgc aggaggctgt ggggatcaag    180
ctgctgtggg tggctgtgat tggggactgg ctgaacctgg tgttcaagtg gatcctgttt    240
ggccagaggc cctactggtg ggtgctggac acagactact acagcaacac ctctgtgccc    300
ctgatcaagc agttccctgt gacctgtgag acaggccctg gcagcccctc tggccacgct    360
atgggcacag ctggggtgta ctacgtgatg gtgaccagca ccctgtctat cttccagggc    420
aagatcaagc ccacctacag gttcaggtgc ctgaacgtga tcctgtggct gggcttctgg    480
gctgtgcagc tgaacgtgtg cctgagcagg atctacctgg ctgcccactt cccccaccag    540
gtggtggctg gggtgctgtc tgggattgct gtggctgaga ccttcagcca catccactct    600
atctacaacg ccagcctgaa gaagtacttc ctgatcacct tcttcctgtt cagctttgct    660
attggcttct acctgctgct gaagggcctg gggggtggacc tgctgtggac cctggagaag   720
gcccagaggt ggtgtgagca gcctgagtgg gtgcacattg acaccacccc ctttgccagc    780
ctgctgaaga acctgggcac cctgtttggc ctgggcctgg ccctgaacag ctctatgtac    840
agggagagct gcaagggcaa gctgagcaag tggctgccct tcaggctgag ctctattgtg    900
gccagcctgg tgctgctgca cgtgtttgac agcctgaagc cccccagcca ggtggagctg    960
gtgttctacg tgctgagctt ctgcaagtct gctgtggtgc cctggcctc tgtgtctgtg   1020
atcccctact gcctggccca ggtgctgggc cagccccaca agaagagcct gtag         1074
```

<210> SEQ ID NO 47
<211> LENGTH: 441
<212> TYPE: DNA
<213> ORGANISM: Artificial Sequence
<220> FEATURE:
<223> OTHER INFORMATION: Codon optimised intron of the -globin gene
      (HBB2 co) used in examples 4 and 5

<400> SEQUENCE: 47

```
gtacacatat tgaccaaatc agggtaattt tgcatttgta attttaaaaa atgctttctt     60
cttttaatat actttttgt ttatcttatt tctaatactt tccctaatct ctttctttca    120
gggcaataat gatacaatgt atcatgcctc tttgcaccat tctaaagaat aacagtgata    180
atttctgggt taaggcaata gcaatatttc tgcatataaa tatttctgca tataaattgt    240
```

```
aactgatgta agaggtttca tattgctaat agcagctaca atccagctac cattctgctt    300
ttattttctg gttgggataa ggctggatta ttctgagtcc aagctaggcc cttttgctaa    360
tcttgttcat acctcttatc ttcctcccac agctcctggg caacctgctg gtctctctgc    420
tggcccatca ctttggcaaa g                                              441
```

<210> SEQ ID NO 48
<211> LENGTH: 3134
<212> TYPE: DNA
<213> ORGANISM: Artificial Sequence
<220> FEATURE:
<223> OTHER INFORMATION: hAAT_HBB2Co_hG6pc wt co1 (expression cassette used in example 5)

<400> SEQUENCE: 48

```
aaggctcaga ggcacacagg agtttctggg ctcaccctgc ccccttccaa cccctcagtt     60
cccatcctcc agcagctgtt tgtgtgctgc ctctgaagtc cacactgaac aaacttcagc    120
ctactcatgt ccctaaaatg ggcaaacatt gcaagcagca aacagcaaac acacagccct    180
ccctgcctgc tgaccttgga gctggggcag aggtcagaga cctctctggg cccatgccac    240
ctccaacatc cactcgaccc cttggaattt cggtggagag gagcagaggt tgtcctggcg    300
tggtttaggt agtgtgagag gggtacccgg ggatcttgct accagtggaa cagccactaa    360
ggattctgca gtgagagcag agggccagct aagtggtact ctcccagaga ctgtctgact    420
cacgccaccc cctccacctt ggacacagga cgctgtggtt tctgagccag gtacaatgac    480
tcctttcggt aagtgcagtg gaagctgtac actgcccagg caaagcgtcc gggcagcgta    540
ggcgggcgac tcagatccca gccagtggac ttagcccctg tttgctcctc cgataactgg    600
ggtgaccttg gttaatattc accagcagcc tcccccgttg cccctctgga tccactgctt    660
aaatacggac gaggacaggg ccctgtctcc tcagcttcag gcaccaccac tgacctggga    720
cagtgaatag atcctgagaa cttcagggtg agtctatggg acccttgatg ttttctttcc    780
ccttcttttc tatggttaag ttcatgtcat aggaagggga gaagtaacag ggtacacata    840
ttgaccaaat cagggtaatt ttgcatttgt aattttaaaa aatgctttct tcttttaata    900
tacttttttg tttatcttat ttctaatact ttccctaatc tctttctttc agggcaataa    960
tgatacaatg tatcatgcct ctttgcacca ttctaaagaa taacagtgat aatttctggg   1020
ttaaggcaat agcaatattt ctgcatataa atatttctgc atataaattg taactgatgt   1080
aagaggtttc atattgctaa tagcagctac aatccagcta ccattctgct tttattttct   1140
ggttgggata aggctggatt attctgagtc caagctaggc ccttttgcta atcttgttca   1200
tacctcttat cttcctccca cagctcctgg gcaacctgct ggtctctctg ctggcccatc   1260
actttggcaa agcacgcgtg ccaccatgga ggaaggaatg aatgttctcc atgactttgg   1320
gatccagtca acacattacc tccaggtgaa ttaccaagac tcccaggact ggttcatctt   1380
ggtgtctgtg attgcagacc tcaggaatgc cttctatgtc ctcttcccca tctggttcca   1440
tcttcaggaa gctgtgggca ttaaactcct ttgggtagct gtgattggag actggctcaa   1500
cctggtcttt aagtggattc tctttggaca gaggccatac tggtgggttt tggatactga   1560
ctactacagc aacacttctg tgcccctgat aaagcagttc cctgtaacct gtgagactgg   1620
accagggagc ccctctggcc atgccatggg cacagcaggt gtatactatg tgatggtcac   1680
atctactctt tccatctttc agggaaagat aaagcccacc tacagattta ggtgcttgaa   1740
tgtcattttg tggttgggat tctgggctgt gcagctgaat gtctgtctgt caaggatcta   1800
```

ccttgctgct cattttcctc atcaagttgt tgctggagtc ctgtcaggca ttgctgttgc 1860
agaaactttc agccacatcc acagcatcta taatgccagc ctcaagaaat attttctcat 1920
taccttcttc ctgttcagct ttgccattgg attttatctg ctgctcaagg gactgggtgt 1980
agacctcctg tggactctgg agaaagccca gaggtggtgt gagcagccag aatgggtcca 2040
cattgacacc acaccctttg ccagcctcct caagaacctg ggcaccctct ttggcctggg 2100
gctggctctc aactccagca tgtacaggga gagctgcaag ggaaaactca gcaagtggct 2160
cccattcagg ctcagctcta ttgtagcctc cctggtcctc ctgcatgtct ttgactcctt 2220
gaaaccccca tcccaagtgg agctggtctt ctatgtcttg tccttctgca agagtgctgt 2280
agtgcccctg gcatctgtca gtgtcatccc ctactgcctg gcccaggtcc tgggccagcc 2340
ccacaagaag tccttgtaac tcgaggaatt caccccacca gtgcaggctg cctatcagaa 2400
agtggtggct ggtgtggcta atgccctggc ccacaagtat cactaagctc gctttcttgc 2460
tgtccaattt ctattaaagg ttcctttgtt ccctaagtcc aactactaaa ctgggggata 2520
ttatgaaggg ccttgagcat ctggattctg cctaataaaa aacatttatt ttcattgcaa 2580
tgatgtattt aaattatttc tgaatatttt actaaaaagg gaatgtggga ggtcagtgca 2640
tttaaaacat aaagaaatga agagctagtt caaaccttgg gaaaatacac tatatcttaa 2700
actccatgaa agaaggtgag gctgcaaaca gctaatgcac attggcaaca gcccctgatg 2760
cctatgcctt attcatccct cagaaaagga ttcaagtaga ggcttgattt ggaggttaaa 2820
gttttgctat gctgtatttt acattactta ttgttttagc tgtcctcatg aatgtctttt 2880
cactacccat ttgcttatcc tgcatctctc agccttgact ccactcagtt ctcttgctta 2940
gagataccac ctttcccctg aagtgttcct tccatgtttt acggcgagat ggtttctcct 3000
cgcctggcca ctcagcctta gttgtctctg ttgtcttata gaggtctact tgaagaagga 3060
aaaacagggg gcatggtttg actgtcctgt gagcccttct tccctgcctc ccccactcac 3120
agtgacccgg aatc 3134

<210> SEQ ID NO 49
<211> LENGTH: 3134
<212> TYPE: DNA
<213> ORGANISM: Artificial Sequence
<220> FEATURE:
<223> OTHER INFORMATION: hAAT_HBB2Co_hG6pc wt co2 (expression cassette used in example 5)

<400> SEQUENCE: 49
aaggctcaga ggcacacagg agtttctggg ctcaccctgc cccctccaa cccctcagtt 60 cccatcctcc agcagctgtt tgtgtgctgc ctctgaagtc cacactgaac aaacttcagc 120
ctactcatgt ccctaaaatg ggcaaacatt gcaagcagca aacagcaaac acacagccct 180
ccctgcctgc tgaccttgga gctggggcag aggtcagaga cctctctggg cccatgccac 240
ctccaacatc cactcgaccc cttggaattt cggtggagag gagcagaggt tgtcctggcg 300
tggtttaggt agtgtgagag gggtacccgg ggatcttgct accagtggaa cagccactaa 360
ggattctgca gtgagagcag agggccagct aagtggtact ctcccagaga ctgtctgact 420
cacgccaccc cctccacctt ggacacagga cgctgtggtt tctgagccag gtacaatgac 480
tcctttcggt aagtgcagtg gaagctgtac actgcccagg caaagcgtcc gggcagcgta 540
ggcgggcgac tcagatccca gccagtggac ttagcccctg tttgctcctc cgataactgg 600
ggtgaccttg gttaatattc accagcagcc tcccccgttg cccctctgga tccactgctt 660

```
aaatacggac gaggacaggg ccctgtctcc tcagcttcag gcaccaccac tgacctggga    720
cagtgaatag atcctgagaa cttcagggtg agtctatggg acccttgatg ttttctttcc    780
ccttcttttc tatggttaag ttcatgtcat aggaagggga gaagtaacag ggtacacata    840
ttgaccaaat cagggtaatt ttgcatttgt aattttaaaa aatgctttct tcttttaata    900
tacttttttg tttatcttat ttctaatact ttccctaatc tctttctttc agggcaataa    960
tgatacaatg tatcatgcct ctttgcacca ttctaaagaa taacagtgat aatttctggg   1020
ttaaggcaat agcaatattt ctgcatataa atatttctgc atataaattg taactgatgt   1080
aagaggtttc atattgctaa tagcagctac aatccagcta ccattctgct tttattttct   1140
ggttgggata aggctggatt attctgagtc caagctaggc ccttttgcta atcttgttca   1200
tacctcttat cttcctccca cagctcctgg gcaacctgct ggtctctctg ctggcccatc   1260
actttggcaa agcacgcgtg ccaccatgga ggaggggatg aacgtgctgc acgactttgg   1320
gatccagagc acccactacc tgcaggtgaa ctaccaggac agccaggact ggtttatcct   1380
ggtgtctgtg attgctgacc tgaggaacgc cttctacgtg ctgttcccta tctggttcca   1440
cctgcaggag gctgtgggga tcaagctgct gtgggtggct gtgattgggg actggctgaa   1500
cctggtgttc aagtggatcc tgtttggcca gaggccctac tggtgggtgc tggacacaga   1560
ctactacagc aacacctctg tgcccctgat caagcagttc cctgtgacct gtgagacagg   1620
ccctggcagc ccctctggcc acgctatggg cacagctggg gtgtactacg tgatggtgac   1680
cagcaccctg tctatcttcc agggcaagat caagcccacc tacaggttca ggtgcctgaa   1740
cgtgatcctg tggctgggct tctgggctgt gcagctgaac gtgtgcctga gcaggatcta   1800
cctggctgcc cacttccccc accaggtggt ggctggggtg ctgtctggga ttgctgtggc   1860
tgagaccttc agccacatcc actctatcta caacgccagc ctgaagaagt acttcctgat   1920
caccttcttc ctgttcagct ttgctattgg cttctacctg ctgctgaagg gcctgggggt   1980
ggacctgctg tggaccctgg agaaggccca gaggtggtgt gagcagcctg agtgggtgca   2040
cattgacacc accccctttg ccagcctgct gaagaacctg ggcaccctgt ttggcctggg   2100
cctggccctg aacagctcta tgtacaggga gagctgcaag ggcaagctga gcaagtggct   2160
gcccttcagg ctgagctcta ttgtggccag cctggtgctg ctgcacgtgt ttgacagcct   2220
gaagcccccc agccaggtgg agctggtgtt ctacgtgctg agcttctgca agtctgctgt   2280
ggtgcccctg gcctctgtgt ctgtgatccc ctactgcctg gcccaggtgc tgggccagcc   2340
ccacaagaag agcctgtagc tcgaggaatt caccccacca gtgcaggctg cctatcagaa   2400
agtggtggct ggtgtggcta atgccctggc ccacaagtat cactaagctc gctttcttgc   2460
tgtccaattt ctattaaagg ttcctttgtt ccctaagtcc aactactaaa ctgggggata   2520
ttatgaaggg ccttgagcat ctggattctg cctaataaaa aacatttatt ttcattgcaa   2580
tgatgtattt aaattatttc tgaatatttt actaaaaagg gaatgtggga ggtcagtgca   2640
tttaaaacat aaagaaatga agagctagtt caaaccttgg gaaaatacac tatatcttaa   2700
actccatgaa agaaggtgag gctgcaaaca gctaatgcac attggcaaca gcccctgatg   2760
cctatgcctt attcatccct cagaaaagga ttcaagtaga ggcttgattt ggaggttaaa   2820
gttttgctat gctgtatttt acattactta ttgttttagc tgtcctcatg aatgtctttt   2880
cactacccat ttgcttatcc tgcatctctc agccttgact ccactcagtt ctcttgctta   2940
gagataccac ctttcccctg aagtgttcct tccatgtttt acggcgagat ggtttctcct   3000
```

-continued

```
cgcctggcca ctcagcctta gttgtctctg ttgtcttata gaggtctact tgaagaagga   3060

aaaacagggg gcatggtttg actgtcctgt gagcccttct tccctgcctc ccccactcac   3120

agtgacccgg aatc                                                     3134


<210> SEQ ID NO 50
<211> LENGTH: 3134
<212> TYPE: DNA
<213> ORGANISM: Artificial Sequence
<220> FEATURE:
<223> OTHER INFORMATION: hAAT_HBB2Co_hG6pc wt co3 (expression cassette
      used in example 5) - comprising SEQ ID NO: 3

<400> SEQUENCE: 50

aaggctcaga ggcacacagg agtttctggg ctcaccctgc ccccttccaa cccctcagtt     60

cccatcctcc agcagctgtt tgtgtgctgc ctctgaagtc cacactgaac aaacttcagc    120

ctactcatgt ccctaaaatg ggcaaacatt gcaagcagca aacagcaaac acacagccct    180

ccctgcctgc tgaccttgga gctggggcag aggtcagaga cctctctggg cccatgccac    240

ctccaacatc cactcgaccc cttggaattt cggtggagag gagcagaggt tgtcctggcg    300

tggtttaggt agtgtgagag gggtacccgg ggatcttgct accagtggaa cagccactaa    360

ggattctgca gtgagagcag agggccagct aagtggtact ctcccagaga ctgtctgact    420

cacgccaccc cctccacctt ggacacagga cgctgtggtt tctgagccag gtacaatgac    480

tcctttcggt aagtgcagtg gaagctgtac actgcccagg caaagcgtcc gggcagcgta    540

ggcgggcgac tcagatccca gccagtggac ttagcccctg tttgctcctc cgataactgg    600

ggtgaccttg gttaatattc accagcagcc tcccccgttg cccctctgga tccactgctt    660

aaatacggac gaggacaggg ccctgtctcc tcagcttcag gcaccaccac tgacctggga    720

cagtgaatag atcctgagaa cttcagggtg agtctatggg acccttgatg ttttctttcc    780

ccttcttttc tatggttaag ttcatgtcat aggaagggga gaagtaacag ggtacacata    840

ttgaccaaat cagggtaatt ttgcatttgt aattttaaaa aatgctttct tcttttaata    900

tacttttttg tttatcttat ttctaatact ttccctaatc tctttctttc agggcaatat    960

tgatacaatg tatcttgcct ctttgcacca ttctaaagaa taacagtgat aatttctggg   1020

ttaaggcaat agcaatattt ctgcatataa atatttctgc atataaattg taactgatgt   1080

aagaggtttc atattgctaa tagcagctac aatccagcta ccattctgct tttattttct   1140

ggttgggata aggctggatt attctgagtc caagctaggc ccttttgcta atcttgttca   1200

tacctcttat cttcctccca cagctcctgg gcaacctgct ggtctctctg ctggcccatc   1260

actttggcaa agcacgcgtg ccaccatgga ggagggaatg aatgtgctgc acgacttcgg   1320

gattcagtct acccactatc tccaagtcaa ttatcaagac agtcaagatt ggttcatcct   1380

cgtctccgtt atagctgacc tcaggaatgc tttttatgta ctgttcccaa tatggtttca   1440

tctgcaagaa gcagttggaa ttaaactgct gtgggtggcc gtaatcggag actggttgaa   1500

cctggtgttc aaatggatcc tttttggtca gaggccatat tggtgggtct tggacaccga   1560

ctattatagc aacacatctg taccccctgat aaagcaattc cctgtaacgt gtgaaactgg   1620

gcctgggtca cccagtggac acgcgatggg gactgccggg gtttactacg taatggttac   1680

tagcacgctt agcattttcc agggcaagat caaaccgact tatcgcttcc gatgcctcaa   1740

tgtgatcctc tggctgggat tctgggcggt tcaactgaac gtatgcctct cacggattta   1800

tctggctgca catttcccgc atcaagtagt ggctggtgtg ttgtctggca tagcagtggc   1860
```

tgaaacattc tcacacattc attctattta caacgcttca ttgaaaaaat actttctgat 1920
tacttttttt cttttcagct ttgcaattgg cttttacttg ctgcttaaag gtcttggcgt 1980
cgacctgctc tggactcttg agaaagcgca acgctggtgc gaacaacccg agtgggtcca 2040
catagatacg accccgttcg cgtctcttct gaaaaatctc ggtaccctct tcggactggg 2100
acttgctttg aattcttcaa tgtatcggga atcctgcaag ggcaaactgt ccaagtggtt 2160
gccctttcgc ctttcaagca ttgtcgcttc ccttgtgctc ctgcacgtct tcgactcact 2220
gaagccgccg agccaagtcg agctcgtgtt ttacgtgttg tctttctgta aaagtgccgt 2280
cgtgccactc gccagtgtga gcgtgatacc ttattgcctc gcacaggtgc ttgggcagcc 2340
tcataagaag tctctgtaaa gatctgaatt caccccacca gtgcaggctg cctatcagaa 2400
agtggtggct ggtgtggcta atgccctggc ccacaagtat cactaagctc gctttcttgc 2460
tgtccaattt ctattaaagg ttcctttgtt ccctaagtcc aactactaaa ctgggggata 2520
ttatgaaggg ccttgagcat ctggattctg cctaataaaa aacatttatt ttcattgcaa 2580
tgatgtattt aaattatttc tgaatatttt actaaaaagg gaatgtggga ggtcagtgca 2640
tttaaaacat aaagaaatga agagctagtt caaaccttgg gaaaatacac tatatcttaa 2700
actccatgaa agaaggtgag gctgcaaaca gctaatgcac attggcaaca gcccctgatg 2760
cctatgcctt attcatccct cagaaaagga ttcaagtaga ggcttgattt ggaggttaaa 2820
gtttggctat gctgtatttt acattactta ttgttttagc tgtcctcatg aatgtctttt 2880
cactacccat ttgcttatcc tgcatctctc agccttgact ccactcagtt ctcttgctta 2940
gagataccac ctttcccctg aagtgttcct tccatgtttt acggcgagat ggtttctcct 3000
cgcctggcca ctcagcctta gttgtctctg ttgtcttata gaggtctact tgaagaagga 3060
aaaacagggg gcatggtttg actgtcctgt gagcccttct tccctgcctc ccccactcac 3120
agtgacccgg aatc 3134

<210> SEQ ID NO 51
<211> LENGTH: 3134
<212> TYPE: DNA
<213> ORGANISM: Artificial Sequence
<220> FEATURE:
<223> OTHER INFORMATION: hAAT_HBB2 co_hG6pc mut (expression cassette)
Comprising SEQ ID NO: 5

<400> SEQUENCE: 51
aaggctcaga ggcacacagg agtttctggg ctcaccctgc ccccttccaa cccctcagtt 60
cccatcctcc agcagctgtt tgtgtgctgc ctctgaagtc cacactgaac aaacttcagc 120
ctactcatgt ccctaaaatg ggcaaacatt gcaagcagca aacagcaaac acacagccct 180
ccctgcctgc tgaccttgga gctggggcag aggtcagaga cctctctggg cccatgccac 240
ctccaacatc cactcgaccc cttggaattt cggtggagag gagcagaggt tgtcctggcg 300
tggtttaggt agtgtgagag gggtacccgg ggatcttgct accagtggaa cagccactaa 360
ggattctgca gtgagagcag agggccagct aagtggtact ctcccagaga ctgtctgact 420
cacgccaccc cctccacctt ggacacagga cgctgtggtt tctgagccag gtacaatgac 480
tcctttcggt aagtgcagtg gaagctgtac actgcccagg caaagcgtcc gggcagcgta 540
ggcgggcgac tcagatccca gccagtggac ttagcccctg tttgctcctc cgataactgg 600
ggtgaccttg gttaatattc accagcagcc tcccccgttg cccctctgga tccactgctt 660
aaatacggac gaggacaggg ccctgtctcc tcagcttcag gcaccaccac tgacctggga 720

-continued

```
cagtgaatag atcctgagaa cttcagggtg agtctatggg acccttgatg ttttctttcc    780
ccttcttttc tatggttaag ttcatgtcat aggaagggga gaagtaacag ggtacacata    840
ttgaccaaat cagggtaatt ttgcatttgt aattttaaaa aatgctttct tcttttaata    900
tacttttttg tttatcttat ttctaatact ttccctaatc tctttctttc agggcaataa    960
tgatacaatg tatcatgcct ctttgcacca ttctaaagaa taacagtgat aatttctggg   1020
ttaaggcaat agcaatattt ctgcatataa atatttctgc atataaattg taactgatgt   1080
aagaggtttc atattgctaa tagcagctac aatccagcta ccattctgct tttattttct   1140
ggttgggata aggctggatt attctgagtc caagctaggc ccttttgcta atcttgttca   1200
tacctcttat cttcctccca cagctcctgg gcaacctgct ggtctctctg ctggcccatc   1260
actttggcaa agcacgcgtg ccaccatgga ggaaggaatg aatgttctcc atgactttgg   1320
gatccagtca acacattacc tccaggtgaa ttaccaagac tcccaggact ggttcatctt   1380
ggtgtccgtg atcgcagacc tcaggaatgc cttctacgtc ctcttcccca tctggttcca   1440
tcttcaggaa gctgtgggca ttaaactcct ttgggtagct gtgattggag actggctcaa   1500
cctcgtcttt aagtggattc tctttggaca gcgtccatac tggtgggttt tggatactga   1560
ctactacagc aacacttccg tgcccctgat aaagcagttc cctgtaacct gtgagactgg   1620
accagggagc cctctggcc atgccatggg cacagcaggt gtatactacg tgatggtcac    1680
atctactctt tccatctttc agggaaagat aaagccgacc tacagatttc ggtgcttgaa   1740
tgtcattttg tggttgggat tctgggctgt gcagctgaat gtctgtctgt cacgaatcta   1800
ccttgctgct cattttcctc atcaagttgt tgctggagtc ctgtcaggca ttgctgttgc   1860
agaaactttc agccacatcc acagcatcta taatgccagc ctcaagaaat attttctcat   1920
taccttcttc ctgttcagct tcgccatcgg attttatctg ctgctcaagg gactgggtgt   1980
agacctcctg tggactctgg agaaagccca gaggtggtgc gagcagccag aatgggtcca   2040
cattgacacc acaccctttg ccagcctcct caagaacctg ggcacgctct ttggcctggg   2100
gctggctctc aactccagca tgtacaggga gagctgcaag gggaaactca gcaagtggct   2160
cccattccgc ctcagctgta ttgtagcctc cctcgtcctc ctgcacgtct ttgactcctt   2220
gaaacccca tcccaagtcg agctggtctt ctacgtcttg tccttctgca agagtgcggt    2280
agtgcccctg gcatccgtca gtgtcatccc ctactgcctc gcccaggtcc tgggccagcc   2340
gcacaagaag tcgttgtaac tcgaggaatt caccccacca gtgcaggctg cctatcagaa   2400
agtggtggct ggtgtggcta atgccctggc ccacaagtat cactaagctc gctttcttgc   2460
tgtccaattt ctattaaagg ttcctttgtt ccctaagtcc aactactaaa ctgggggata   2520
ttatgaaggg ccttgagcat ctggattctg cctaataaaa aacatttatt ttcattgcaa   2580
tgatgtattt aaattatttc tgaatatttt actaaaaagg gaatgtggga ggtcagtgca   2640
tttaaaacat aaagaaatga agagctagtt caaaccttgg gaaaatacac tatatcttaa   2700
actccatgaa agaaggtgag gctgcaaaca gctaatgcac attggcaaca gcccctgatg   2760
cctatgcctt attcatccct cagaaaagga ttcaagtaga ggcttgattt ggaggttaaa   2820
gttttgctat gctgtatttt acattactta ttgttttagc tgtcctcatg aatgtctttt   2880
cactacccat ttgcttatcc tgcatctctc agccttgact ccactcagtt ctcttgctta   2940
gagataccac ctttcccctg aagtgttcct tccatgtttt acggcgagat ggtttctcct   3000
cgcctggcca ctcagcctta gttgtctctg ttgtcttata gaggtctact tgaagaagga   3060
aaaacagggg gcatggtttg actgtcctgt gagcccttct tccctgcctc ccccactcac   3120
```

agtgacccgg aatc 3134

<210> SEQ ID NO 52
<211> LENGTH: 1074
<212> TYPE: DNA
<213> ORGANISM: Artificial Sequence
<220> FEATURE:
<223> OTHER INFORMATION: Codon optimized hG6pc mut (co1)

<400> SEQUENCE: 52
atggaggaag gaatgaatgt tctccatgac tttgggatcc agtcaacaca ttacctccag 60
gtgaattacc aagactccca ggactggttc atcttggtgt ctgtgattgc agacctcagg 120
aatgccttct atgtcctctt ccccatctgg ttccatcttc aggaagctgt gggcattaaa 180
ctcctttggg tagctgtgat tggagactgg ctcaacctgg tctttaagtg gattctcttt 240
ggacagaggc catactggtg ggttttggat actgactact acagcaacac ttctgtgccc 300
ctgataaagc agttccctgt aacctgtgag actggaccag ggagcccctc tggccatgcc 360
atgggcacag caggtgtata ctatgtgatg gtcacatcta ctctttccat ctttcaggga 420
aagataaagc ccacctacag atttaggtgc ttgaatgtca ttttgtggtt gggattctgg 480
gctgtgcagc tgaatgtctg tctgtcaagg atctaccttg ctgctcattt tcctcatcaa 540
gttgttgctg gagtcctgtc aggcattgct gttgcagaaa ctttcagcca catccacagc 600
atctataatg ccagcctcaa gaaatatttt ctcattacct tcttcctgtt cagctttgcc 660
attggatttt atctgctgct caagggactg ggtgtagacc tcctgtggac tctggagaaa 720
gcccagaggt ggtgtgagca gccagaatgg gtccacattg acaccacacc ctttgccagc 780
ctcctcaaga acctgggcac cctctttggc ctggggctgg ctctcaactc cagcatgtac 840
agggagagct gcaaggggaa actcagcaag tggctcccat tcaggctcag ctgtattgta 900
gcctccctgg tcctcctgca tgtctttgac tccttgaaac cccatcccca agtggagctg 960
gtcttctatg tcttgtcctt ctgcaagagt gctgtagtgc ccctggcatc tgtcagtgtc 1020
atcccctact gcctggccca ggtcctgggc cagccccaca agaagtcctt gtaa 1074

<210> SEQ ID NO 53
<211> LENGTH: 3134
<212> TYPE: DNA
<213> ORGANISM: Artificial Sequence
<220> FEATURE:
<223> OTHER INFORMATION: hAAT_HBB2 co_hG6pc mut co1 (expression cassette)

<400> SEQUENCE: 53
aaggctcaga ggcacacagg agtttctggg ctcaccctgc ccccttccaa cccctcagtt 60
cccatcctcc agcagctgtt tgtgtgctgc ctctgaagtc cacactgaac aaacttcagc 120
ctactcatgt ccctaaaatg ggcaaacatt gcaagcagca aacagcaaac acacagccct 180
ccctgcctgc tgaccttgga gctggggcag aggtcagaga cctctctggg cccatgccac 240
ctccaacatc cactcgaccc cttggaattt cggtggagag gagcagaggt tgtcctggcg 300
tggtttaggt agtgtgagag gggtacccgg ggatcttgct accagtggaa cagccactaa 360
ggattctgca gtgagagcag agggccagct aagtggtact ctcccagaga ctgtctgact 420
cacgccaccc cctccacctt ggacacagga cgctgtggtt tctgagccag gtacaatgac 480
tcctttcggt aagtgcagtg gaagctgtac actgcccagg caaagcgtcc gggcagcgta 540
ggcgggcgac tcagatccca gccagtggac ttagcccctg tttgctcctc cgataactgg 600

```
ggtgaccttg gttaatattc accagcagcc tcccccgttg cccctctgga tccactgctt    660
aaatacggac gaggacaggg ccctgtctcc tcagcttcag gcaccaccac tgacctggga    720
cagtgaatag atcctgagaa cttcagggtg agtctatggg acccttgatg ttttctttcc    780
ccttcttttc tatggttaag ttcatgtcat aggaagggga gaagtaacag ggtacacata    840
ttgaccaaat cagggtaatt ttgcatttgt aattttaaaa aatgctttct tcttttaata    900
tacttttttg tttatcttat ttctaatact ttccctaatc tctttctttc agggcaataa    960
tgatacaatg tatcatgcct ctttgcacca ttctaaagaa taacagtgat aatttctggg   1020
ttaaggcaat agcaatattt ctgcatataa atatttctgc atataaattg taactgatgt   1080
aagaggtttc atattgctaa tagcagctac aatccagcta ccattctgct tttattttct   1140
ggttgggata aggctggatt attctgagtc caagctaggc ccttttgcta atcttgttca   1200
tacctcttat cttcctccca cagctcctgg gcaacctgct ggtctctctg ctggcccatc   1260
actttggcaa agcacgcgtg ccaccatgga ggaaggaatg aatgttctcc atgactttgg   1320
gatccagtca acacattacc tccaggtgaa ttaccaagac tcccaggact ggttcatctt   1380
ggtgtctgtg attgcagacc tcaggaatgc cttctatgtc ctcttcccca tctggttcca   1440
tcttcaggaa gctgtgggca ttaaactcct ttgggtagct gtgattggag actggctcaa   1500
cctggtcttt aagtggattc tctttggaca gaggccatac tggtgggttt tggatactga   1560
ctactacagc aacacttctg tgcccctgat aaagcagttc cctgtaacct gtgagactgg   1620
accagggagc ccctctggcc atgccatggg cacagcaggt gtatactatg tgatggtcac   1680
atctactctt tccatctttc agggaaagat aaagcccacc tacagattta ggtgcttgaa   1740
tgtcattttg tggttgggat tctgggctgt gcagctgaat gtctgtctgt caaggatcta   1800
ccttgctgct cattttcctc atcaagttgt tgctggagtc ctgtcaggca ttgctgttgc   1860
agaaactttc agccacatcc acagcatcta taatgccagc ctcaagaaat attttctcat   1920
taccttcttc ctgttcagct ttgccattgg attttatctg ctgctcaagg gactgggtgt   1980
agacctcctg tggactctgg agaaagccca gaggtggtgt gagcagccag aatgggtcca   2040
cattgacacc acaccctttg ccagcctcct caagaacctg ggcaccctct ttggcctggg   2100
gctggctctc aactccagca tgtacaggga gagctgcaag gggaaactca gcaagtggct   2160
cccattcagg ctcagctgta ttgtagcctc cctggtcctc ctgcatgtct ttgactcctt   2220
gaaaccccca tcccaagtgg agctggtctt ctatgtcttg tccttctgca agagtgctgt   2280
agtgcccctg gcatctgtca gtgtcatccc ctactgcctg gcccaggtcc tgggccagcc   2340
ccacaagaag tccttgtaac tcgaggaatt caccccacca gtgcaggctg cctatcagaa   2400
agtggtggct ggtgtggcta atgccctggc ccacaagtat cactaagctc gctttcttgc   2460
tgtccaattt ctattaaagg ttcctttgtt ccctaagtcc aactactaaa ctgggggata   2520
ttatgaaggg ccttgagcat ctggattctg cctaataaaa aacatttatt ttcattgcaa   2580
tgatgtattt aaattatttc tgaatatttt actaaaaagg gaatgtggga ggtcagtgca   2640
tttaaaacat aaagaaatga agagctagtt caaaccttgg gaaaatacac tatatcttaa   2700
actccatgaa agaaggtgag gctgcaaaca gctaatgcac attggcaaca gcccctgatg   2760
cctatgcctt attcatccct cagaaaagga ttcaagtaga ggcttgattt ggaggttaaa   2820
gttttgctat gctgtatttt acattactta ttgttttagc tgtcctcatg aatgtctttt   2880
cactacccat ttgcttatcc tgcatctctc agccttgact ccactcagtt ctcttgctta   2940
```

gagataccac ctttcccctg aagtgttcct tccatgtttt acggcgagat ggtttctcct 3000
cgcctggcca ctcagcctta gttgtctctg ttgtcttata gaggtctact tgaagaagga 3060
aaaacagggg gcatggtttg actgtcctgt gagcccttct tccctgcctc ccccactcac 3120
agtgacccgg aatc 3134

<210> SEQ ID NO 54
<211> LENGTH: 1074
<212> TYPE: DNA
<213> ORGANISM: Artificial Sequence
<220> FEATURE:
<223> OTHER INFORMATION: Codon optimized hG6pc mut (co2)

<400> SEQUENCE: 54
atggaggagg ggatgaacgt gctgcacgac tttgggatcc agagcaccca ctacctgcag 60
gtgaactacc aggacagcca ggactggttt atcctggtgt ctgtgattgc tgacctgagg 120
aacgccttct acgtgctgtt ccctatctgg ttccacctgc aggaggctgt ggggatcaag 180
ctgctgtggg tggctgtgat tggggactgg ctgaacctgg tgttcaagtg gatcctgttt 240
ggccagaggc cctactggtg ggtgctggac acagactact acagcaacac ctctgtgccc 300
ctgatcaagc agttccctgt gacctgtgag acaggccctg gcagcccctc tggccacgct 360
atgggcacag ctggggtgta ctacgtgatg gtgaccagca ccctgtctat cttccagggc 420
aagatcaagc ccacctacag gttcaggtgc ctgaacgtga tcctgtggct gggcttctgg 480
gctgtgcagc tgaacgtgtg cctgagcagg atctacctgg ctgcccactt cccccaccag 540
gtggtggctg gggtgctgtc tgggattgct gtggctgaga ccttcagcca catccactct 600
atctacaacg ccagcctgaa gaagtacttc ctgatcacct tcttcctgtt cagctttgct 660
attggcttct acctgctgct gaagggcctg gggtggacc tgctgtggac cctggagaag 720
gcccagaggt ggtgtgagca gcctgagtgg gtgcacattg acaccacccc ctttgccagc 780
ctgctgaaga acctgggcac cctgtttggc ctgggcctgg ccctgaacag ctctatgtac 840
agggagagct gcaagggcaa gctgagcaag tggctgccct tcaggctgag ctgtattgtg 900
gccagcctgg tgctgctgca cgtgtttgac agcctgaagc cccccagcca ggtggagctg 960
gtgttctacg tgctgagctt ctgcaagtct gctgtggtgc cctggcctc tgtgtctgtg 1020 atcccctact gcctggccca ggtgctgggc cagccccaca agaagagcct gtag 1074

<210> SEQ ID NO 55
<211> LENGTH: 3134
<212> TYPE: DNA
<213> ORGANISM: Artificial Sequence
<220> FEATURE:
<223> OTHER INFORMATION: hAAT_HBB2 co_hG6pc mut co2 (expression cassette)

<400> SEQUENCE: 55
aaggctcaga ggcacacagg agtttctggg ctcaccctgc ccccttccaa cccctcagtt 60
cccatcctcc agcagctgtt tgtgtgctgc ctctgaagtc cacactgaac aaacttcagc 120
ctactcatgt ccctaaaatg ggcaaacatt gcaagcagca aacagcaaac acacagccct 180
ccctgcctgc tgaccttgga gctggggcag aggtcagaga cctctctggg cccatgccac 240
ctccaacatc cactcgaccc cttggaattt cggtggagag gagcagaggt tgtcctggcg 300
tggtttaggt agtgtgagag gggtacccgg ggatcttgct accagtggaa cagccactaa 360
ggattctgca gtgagagcag agggccagct aagtggtact ctcccagaga ctgtctgact 420

-continued

```
cacgccaccc cctccacctt ggacacagga cgctgtggtt tctgagccag gtacaatgac    480
tcctttcggt aagtgcagtg gaagctgtac actgcccagg caaagcgtcc gggcagcgta    540
ggcgggcgac tcagatccca gccagtggac ttagcccctg tttgctcctc cgataactgg    600
ggtgaccttg gttaatattc accagcagcc tcccccgttg cccctctgga tccactgctt    660
aaatacggac gaggacaggg ccctgtctcc tcagcttcag gcaccaccac tgacctggga    720
cagtgaatag atcctgagaa cttcagggtg agtctatggg acccttgatg ttttctttcc    780
ccttcttttc tatggttaag ttcatgtcat aggaagggga gaagtaacag ggtacacata    840
ttgaccaaat cagggtaatt ttgcatttgt aattttaaaa aatgctttct tcttttaata    900
tactttttttg tttatcttat ttctaatact ttccctaatc tctttctttc agggcaataa    960
tgatacaatg tatcatgcct ctttgcacca ttctaaagaa taacagtgat aatttctggg   1020
ttaaggcaat agcaatattt ctgcatataa atatttctgc atataaattg taactgatgt   1080
aagaggtttc atattgctaa tagcagctac aatccagcta ccattctgct tttattttct   1140
ggttgggata aggctggatt attctgagtc caagctaggc ccttttgcta atcttgttca   1200
tacctcttat cttcctccca cagctcctgg gcaacctgct ggtctctctg ctggcccatc   1260
actttggcaa agcacgcgtg ccaccatgga ggaggggatg aacgtgctgc acgactttgg   1320
gatccagagc acccactacc tgcaggtgaa ctaccaggac agccaggact ggtttatcct   1380
ggtgtctgtg attgctgacc tgaggaacgc cttctacgtg ctgttcccta tctggttcca   1440
cctgcaggag gctgtgggga tcaagctgct gtgggtggct gtgattgggg actggctgaa   1500
cctggtgttc aagtggatcc tgtttggcca gaggccctac tggtgggtgc tggacacaga   1560
ctactacagc aacacctctg tgcccctgat caagcagttc cctgtgacct gtgagacagg   1620
ccctggcagc ccctctggcc acgctatggg cacagctggg gtgtactacg tgatggtgac   1680
cagcaccctg tctatcttcc agggcaagat caagcccacc tacaggttca ggtgcctgaa   1740
cgtgatcctg tggctgggct tctgggctgt gcagctgaac gtgtgcctga gcaggatcta   1800
cctggctgcc cacttccccc accaggtggt ggctggggtg ctgtctggga ttgctgtggc   1860
tgagaccttc agccacatcc actctatcta caacgccagc ctgaagaagt acttcctgat   1920
caccttcttc ctgttcagct ttgctattgg cttctacctg ctgctgaagg gcctgggggt   1980
ggacctgctg tggaccctgg agaaggccca gaggtggtgt gagcagcctg agtgggtgca   2040
cattgacacc acccccttttg ccagcctgct gaagaacctg ggcaccctgt ttggcctggg   2100
cctggccctg aacagctcta tgtacaggga gagctgcaag ggcaagctga gcaagtggct   2160
gcccttcagg ctgagctgta ttgtggccag cctggtgctg ctgcacgtgt ttgacagcct   2220
gaagcccccc agccaggtgg agctggtgtt ctacgtgctg agcttctgca agtctgctgt   2280
ggtgcccctg gcctctgtgt ctgtgatccc ctactgcctg gcccaggtgc tgggccagcc   2340
ccacaagaag agcctgtagc tcgaggaatt caccccacca gtgcaggctg cctatcagaa   2400
agtggtggct ggtgtggcta atgccctggc ccacaagtat cactaagctc gctttcttgc   2460
tgtccaattt ctattaaagg ttcctttgtt ccctaagtcc aactactaaa ctgggggata   2520
ttatgaaggg ccttgagcat ctggattctg cctaataaaa aacatttatt ttcattgcaa   2580
tgatgtattt aaattatttc tgaatatttt actaaaaagg gaatgtggga ggtcagtgca   2640
tttaaaacat aaagaaatga agagctagtt caaaccttgg gaaaatacac tatatcttaa   2700
actccatgaa agaaggtgag gctgcaaaca gctaatgcac attggcaaca gcccctgatg   2760
cctatgcctt attcatccct cagaaaagga ttcaagtaga ggcttgattt ggaggttaaa   2820
```

-continued gttttgctat gctgtatttt acattactta ttgttttagc tgtcctcatg aatgtctttt 2880
cactacccat ttgcttatcc tgcatctctc agccttgact ccactcagtt ctcttgctta 2940
gagataccac ctttcccctg aagtgttcct tccatgtttt acggcgagat ggtttctcct 3000
cgcctggcca ctcagcctta gttgtctctg ttgtcttata gaggtctact tgaagaagga 3060
aaaacagggg gcatggtttg actgtcctgt gagcccttct tccctgcctc ccccactcac 3120
agtgacccgg aatc 3134

<210> SEQ ID NO 56
<211> LENGTH: 3134
<212> TYPE: DNA
<213> ORGANISM: Artificial Sequence
<220> FEATURE:
<223> OTHER INFORMATION: hAAT_HBB2 co_hG6pc wt (expression cassette used in example 4 and 5) - comprising SEQ ID NO: 2

<400> SEQUENCE: 56
aaggctcaga ggcacacagg agtttctggg ctcaccctgc cccttccaa cccctcagtt 60 cccatcctcc agcagctgtt tgtgtgctgc ctctgaagtc cacactgaac aaacttcagc 120
ctactcatgt ccctaaaatg ggcaaacatt gcaagcagca aacagcaaac acacagccct 180
ccctgcctgc tgaccttgga gctggggcag aggtcagaga cctctctggg cccatgccac 240
ctccaacatc cactcgaccc cttggaattt cggtggagag gagcagaggt tgtcctggcg 300
tggtttaggt agtgtgagag gggtacccgg ggatcttgct accagtggaa cagccactaa 360
ggattctgca gtgagagcag agggccagct aagtggtact ctcccagaga ctgtctgact 420
cacgccaccc cctccacctt ggacacagga cgctgtggtt tctgagccag gtacaatgac 480
tcctttcggt aagtgcagtg gaagctgtac actgcccagg caaagcgtcc gggcagcgta 540
ggcgggcgac tcagatccca gccagtggac ttagcccctg tttgctcctc cgataactgg 600
ggtgaccttg gttaatattc accagcagcc tcccccgttg cccctctgga tccactgctt 660
aaatacggac gaggacaggg ccctgtctcc tcagcttcag gcaccaccac tgacctggga 720
cagtgaatag atcctgagaa cttcagggtg agtctatggg acccttgatg ttttctttcc 780
ccttcttttc tatggttaag ttcatgtcat aggaagggga gaagtaacag ggtacacata 840
ttgaccaaat cagggtaatt ttgcatttgt aattttaaaa aatgctttct tcttttaata 900 tactttttttg tttatcttat ttctaatact ttccctaatc tctttctttc agggcaataa 960
tgatacaatg tatcatgcct ctttgcacca ttctaaagaa taacagtgat aatttctggg 1020
ttaaggcaat agcaatattt ctgcatataa atatttctgc atataaattg taactgatgt 1080
aagaggtttc atattgctaa tagcagctac aatccagcta ccattctgct tttattttct 1140
ggttgggata aggctggatt attctgagtc caagctaggc ccttttgcta atcttgttca 1200
tacctcttat cttcctccca cagctcctgg gcaacctgct ggtctctctg ctggcccatc 1260
actttggcaa agcacgcgtg ccaccatgga ggaaggaatg aatgttctcc atgactttgg 1320
gatccagtca acacattacc tccaggtgaa ttaccaagac tcccaggact ggttcatctt 1380
ggtgtccgtg atcgcagacc tcaggaatgc cttctacgtc ctcttcccca tctggttcca 1440
tcttcaggaa gctgtgggca ttaaactcct ttgggtagct gtgattggag actggctcaa 1500
cctcgtcttt aagtggattc tctttggaca gcgtccatac tggtgggttt tggatactga 1560
ctactacagc aacacttccg tgcccctgat aaagcagttc cctgtaacct gtgagactgg 1620
accagggagc cctctggcc atgccatggg cacagcaggt gtatactacg tgatggtcac 1680
atctactctt tccatctttc agggaaagat aaagccgacc tacagatttc ggtgcttgaa 1740
tgtcattttg tggttgggat tctgggctgt gcagctgaat gtctgtctgt cacgaatcta 1800
ccttgctgct cattttcctc atcaagttgt tgctggagtc ctgtcaggca ttgctgttgc 1860
agaaactttc agccacatcc acagcatcta taatgccagc ctcaagaaat attttctcat 1920
taccttcttc ctgttcagct tcgccatcgg attttatctg ctgctcaagg gactgggtgt 1980
agacctcctg tggactctgg agaaagccca gaggtggtgc gagcagccag aatgggtcca 2040
cattgacacc acaccctttg ccagcctcct caagaacctg ggcacgctct ttggcctggg 2100
gctggctctc aactccagca tgtacaggga gagctgcaag ggaaaactca gcaagtggct 2160
cccattccgc ctcagctcta ttgtagcctc cctcgtcctc ctgcacgtct ttgactcctt 2220 gaaacccca tcccaagtcg agctggtctt ctacgtcttg tccttctgca agagtgcggt 2280
agtgcccctg gcatccgtca gtgtcatccc ctactgcctc gcccaggtcc tgggccagcc 2340
gcacaagaag tcgttgtaaa gatctgaatt caccccacca gtgcaggctg cctatcagaa 2400
agtggtggct ggtgtggcta atgccctggc ccacaagtat cactaagctc gctttcttgc 2460
tgtccaattt ctattaaagg ttcctttgtt ccctaagtcc aactactaaa ctgggggata 2520
ttatgaaggg ccttgagcat ctggattctg cctaataaaa aacatttatt ttcattgcaa 2580
tgatgtattt aaattatttc tgaatatttt actaaaaagg gaatgtggga ggtcagtgca 2640
tttaaaacat aaagaaatga agagctagtt caaaccttgg gaaaatacac tatatcttaa 2700
actccatgaa agaaggtgag gctgcaaaca gctaatgcac attggcaaca gcccctgatg 2760
cctatgcctt attcatccct cagaaaagga ttcaagtaga ggcttgattt ggaggttaaa 2820
gttttgctat gctgtatttt acattactta ttgttttagc tgtcctcatg aatgtctttt 2880
cactacccat ttgcttatcc tgcatctctc agccttgact ccactcagtt ctcttgctta 2940
gagataccac ctttcccctg aagtgttcct tccatgtttt acggcgagat ggtttctcct 3000
cgcctggcca ctcagcctta gttgtctctg ttgtcttata gaggtctact tgaagaagga 3060
aaaacagggg gcatggtttg actgtcctgt gagcccttct tccctgcctc ccccactcac 3120
agtgacccgg aatc 3134

<210> SEQ ID NO 57
<211> LENGTH: 2217
<212> TYPE: DNA
<213> ORGANISM: Artificial Sequence
<220> FEATURE:
<223> OTHER INFORMATION: Synthetic polynucleotide coding for AAVMut5

<400> SEQUENCE: 57
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540

-continued

```
gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900

cgactcatca acaacaactg gggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta tctgaacaag acacaatcaa atagtggaac tcttcagcag   1380

tctcggctac tgtttagtca agctggaccc accagcatgt ctcttcaagc taaaaactgg   1440

ctgcctggac cttgctaccg ccaacaacgc gtctcaacga caaccgggca aaacaacaat   1500

agcaactttg cctggactgc tggaccaaa taccatctga atggaagaaa ttcattggct    1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtggcag ataacttgca gcagcaaaac acggctcctc aaattggaac tgtcaacagc   1800

caggggggcct tacccggtat ggtctggcag aaccgggacg tgtacctgca gggtcccatc  1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

<210> SEQ ID NO 58
<211> LENGTH: 738
<212> TYPE: PRT
<213> ORGANISM: Artificial Sequence
<220> FEATURE:
<223> OTHER INFORMATION: AAVmut5 (amino acid)

<400> SEQUENCE: 58

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
```

-continued

```
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Asn Lys Thr Gln Ser Asn Ser Gly Thr Leu Gln Gln Ser Arg Leu Leu
    450                 455                 460

Phe Ser Gln Ala Gly Pro Thr Ser Met Ser Leu Gln Ala Lys Asn Trp
465                 470                 475                 480

Leu Pro Gly Pro Cys Tyr Arg Gln Gln Arg Val Ser Thr Thr Thr Gly
                485                 490                 495
```

-continued

```
Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

VECTORS ENCODING A GLUCOSE-6-PHOSPHATASE (G6PASE-A) FOR GENE THERAPY

CROSS REFERENCE TO RELATED APPLICATIONS

This application is a U.S. National Stage Application of PCT/EP2021/063728 filed 21 May 2021, which claims priority to European Patent Application No. 20305540.5 filed on 22 May 2020, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 21 Nov. 2022, is named 0177_0196_ST25.txt and is 148 kilobytes in size.

FIELD OF THE INVENTION

The invention relates to an adeno-associated virus (AAV) comprising a nucleic acid construct for the expression of a glucose-6-phosphatase-a (G6Pase-a) in a cell, useful in the treatment of glycogen storage disease Ia (GSD-Ia), wherein the nucleic acid sequence encoding the G6Pase-a is operably linked to a human alpha-1 antitrypsin (hAAT) promoter.

BACKGROUND OF THE INVENTION

Glycogen storage disease type Ia (GSD-Ia or von Gierke disease) is caused by a deficiency in glucose-6-phosphatase-a (G6Pase-a), an enzyme that is expressed primarily in the liver, kidney, and intestine. G6Pase-a, encoded by the G6PC gene, is a hydrophobic protein anchored in the endoplasmic reticulum (ER) by nine transmembrane helices. This enzyme catalyzes the hydrolysis of glucose-6-phosphate (G6P) to glucose and inorganic phosphate in the terminal step of glycogenolysis and gluconeogenesis. Patients affected by GSD-Ia are unable to maintain glucose homeostasis and present with fasting hypoglycemia, growth retardation, hepatomegaly, nephromegaly, hyperlipidemia, hyperuricemia, and lactic academia.

Most of the time, hypoglycemia can be managed using dietary therapies that enable patients to attain near normal growth and pubertal development. However, the long-term clinical complications, and their underlying pathological processes, remain uncorrected. One of the most significant chronic risks is hepatocellular adenoma (HCA), that develops in 70-80% of GSD-I patients over 25 year-old. HCAs in GSD-Ia patients are multiple and non-encapsulated, with complications including local compression and intratumoral hemorrhage. In 10% of GSD-Ia patients, HCAs undergo malignant transformation to hepatocellular carcinoma (HCC).

Thus, a need exists for an improved therapy vector for the treatment of GSD-Ia and its associated complications.

Gene therapy studies using recombinant adeno-associated virus (AAV) carrying G6Pase-a have previously been performed in animal models of GSD-Ia. In particular, the prior art discloses the use of nucleic acid constructs comprising a nucleic acid sequence encoding the G6Pase-a which is operably linked to a G6PC promoter/enhancer (GPE).

Complications of treatment related to immune responses against the vector represent serious obstacles for the use of AAV vectors in gene therapy. The administration of lower doses of AAV vectors is, in general, associated to a lower activation of the immune response and a better stability of transgene expression [15]. In order to decrease the appearance of side effects associated with the use of AAV vectors, it is therefore preferable to administer the lowest amount of AAV vector that is sufficient to obtain a therapeutically effective effect in a subject.

Thus, there is a need for improved nucleic acid constructs that increases G6Pase-a expression and activity in gene therapy, allowing to decrease the amount of AAV vector that is necessary to achieve a therapeutic effect in a subject.

SUMMARY OF THE INVENTION

The inventors have surprisingly shown that, in particular in an AAV gene therapy setting, a nucleic acid encoding G6Pase-a under the control of a hAAT promoter leads to increased G6Pase-a expression and G6Pase-a activity that permits phenotypical rescue in GSDIa mice compared to hGPE promoter. This was particularly unexpected in view of the prior art that used different forms of G6Pase native promoter (GPE) derived from different species to treat GSDIa.

In addition, the inventors have also shown that the same nucleic acid encoding G6Pase-a under the control of a hAAT promoter decreases the risk of tumor formation, such as HCA and HCC, when compared to hGPE promoter in gene therapy. This was also particularly unexpected in view of the prior art that predicts that promoters with higher activity are more likely to increase the risk of HCA and HCC after gene therapy [1].

Thus, in a first aspect, the invention relates to an adeno-associated virus (AAV) vector comprising a nucleic acid construct for the expression of a glucose-6-phosphatase-a (G6Pase-a) in a cell, the construct comprising a nucleic acid sequence encoding the G6Pase-a, wherein the nucleic acid sequence encoding the G6Pase-a is operably linked to a human alpha-1 antitrypsin (hAAT) promoter.

In a second aspect, the invention relates to a cell transformed with the vector of the invention.

In a third aspect, the invention relates to a composition comprising the vector of the invention, or the cell of the invention.

In a fourth aspect, the invention relates to the vector, the cell or the composition of the invention, for use as a medicament, in particular for use in the treatment of glycogen storage disease Ia (GSD-Ia).

LEGENDS TO THE FIGURES

FIG. 1 shows the correction of the liver phenotype in GSD-Ia mice and WT mice after 15 days of treatment with AAV vectors or PBS. A. is the scheme of the protocol. B. shows the glycemia measured after 6 h of fasting at the end of the protocol. C. shows G6Pase activity measured in liver tissues. D. shows glycogen content of liver tissues. E. shows hepatomegaly reported as the percentage of liver/body weight. F. shows the vector genome copy number per diploid genome measured in liver of AAV-treated mice. Statistical analyses were performed by ANOVA in A-E (#$P<0.05$ vs. PBS-injected L.G6pc$^{+/+}$ mice; * $P<0.05$ vs. PBS-injected L.G6pc$^{-/-}$ mice) and by t-test in F (ns, not significant).

Figure 2:
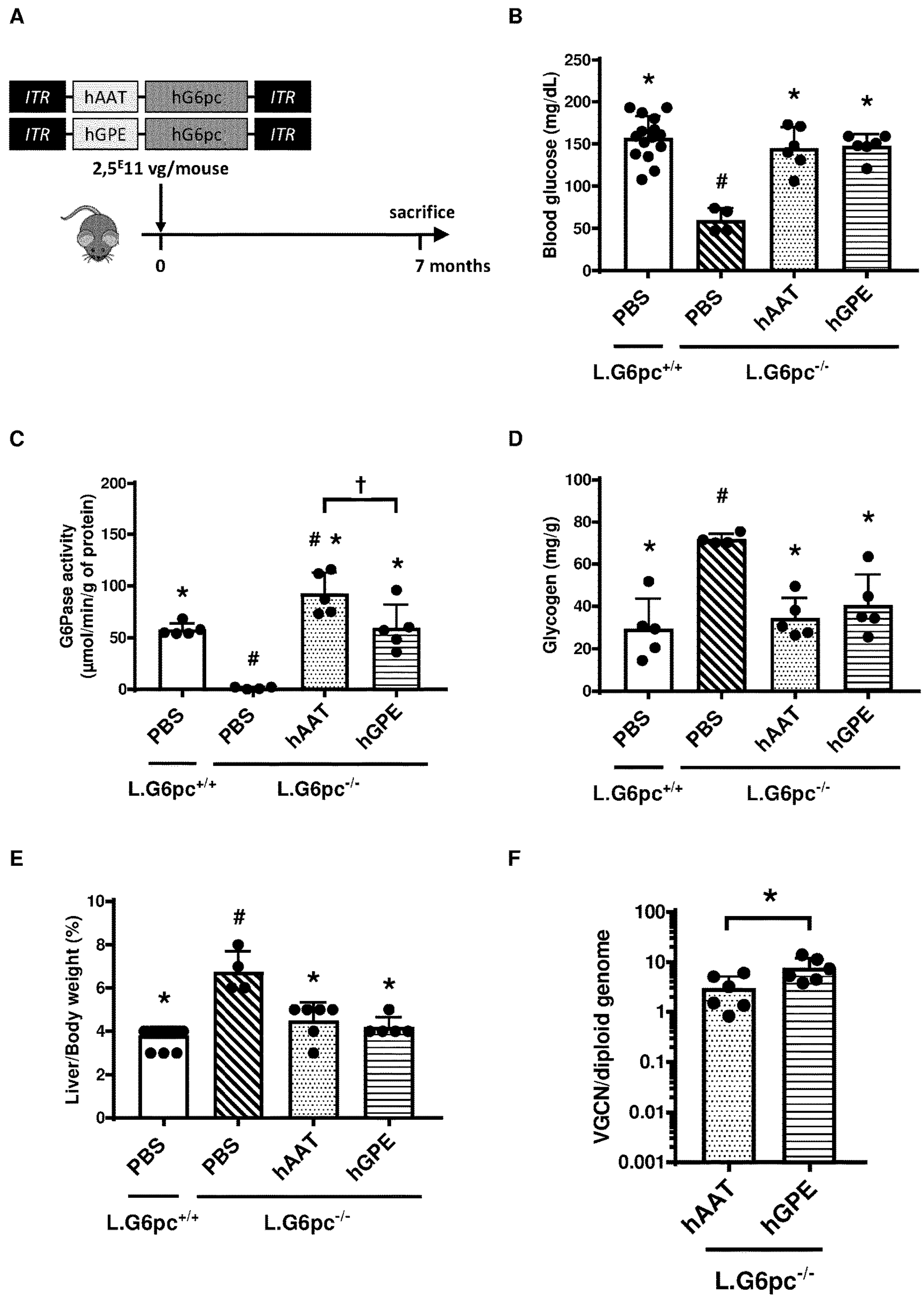

FIG. 2 shows the long-term correction of the liver phenotype in GSD-Ia mice. A. represents the scheme of the protocol. B. shows the glycemia measured after 6 h of fasting at the end of the protocol, i.e. 7 months after vector injection. C. shows the G6Pase activity measured in liver tissues collected at sacrifice. D. shows the glycogen content measured on liver tissues. E. shows the hepatomegaly reported as the percentage of liver/body weight at sacrifice. F. shows the vector genome copy number per diploid genome measured in liver of AAV-treated mice. Statistical analyses were performed by ANOVA (#P<0.05 vs. PBS-injected L.G6pc$^{+/+}$ mice; * P<0.05 vs. PBS-injected L.G6pc$^{-/-}$ mice; † P<0.05 as indicated) and by t-test in F (* P<0.05).

Figure 3:
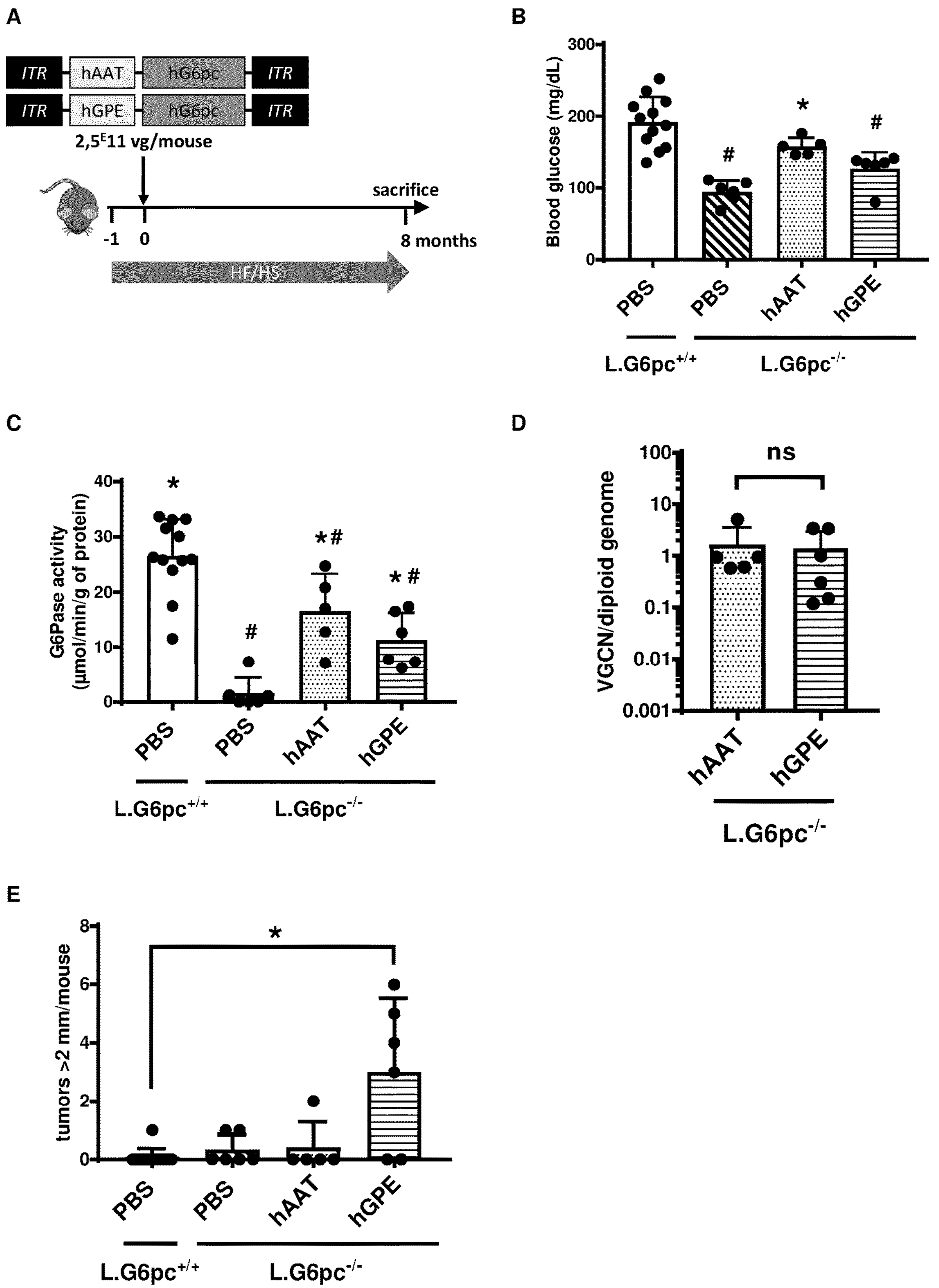

FIG. 3 shows that hGPE-directed gene therapy promotes hepatic tumor formation in L.G6pc$^{-/-}$ mice fed a high fat high sucrose diet. A. represents the scheme of the protocol. B. shows the glycemia measured after 6 h of fasting at the end of the protocol i.e. 8 months after vectors injection. C. shows the G6Pase-a activity assay performed on liver tissues collected at sacrifice. D. shows the vector genome copy number per diploid genome measured in liver. E. shows the number of tumors larger than 2 mm observed in PBS or AAV vector-treated L.G6pc$^{-/-}$ mice 8 months after the start of the HF/HS regimen. Statistical analyses were performed by ANOVA in B and C (#P<0.05 vs. PBS-injected L.G6pc$^{+/+}$ mice; * P<0.05 vs. PBS-injected L.G6pc$^{-/-}$ mice), by t-test in D (ns, not significant) and by non-parametric ANOVA in E (* P<0.05 vs. PBS-injected L.G6pc$^{+/+}$ mice).

Figure 4:
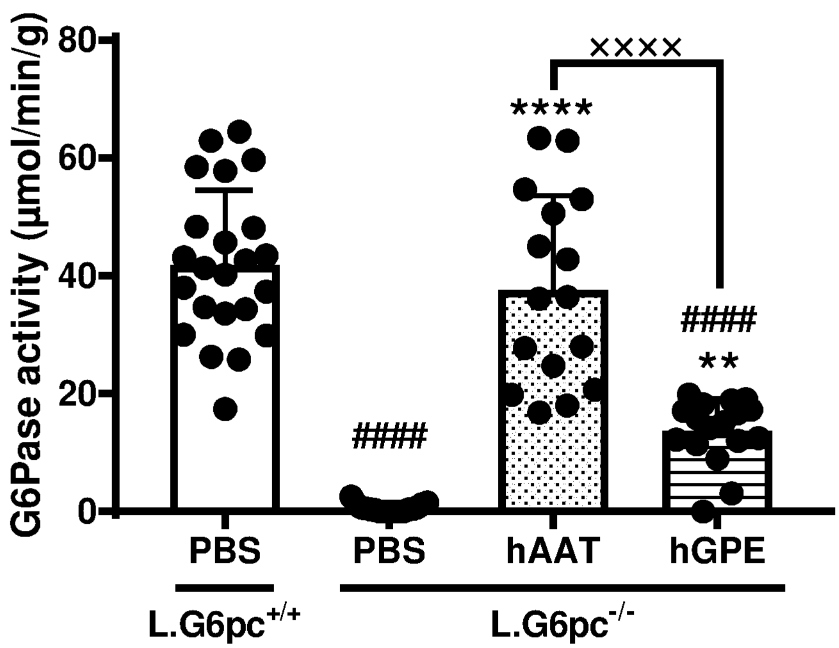

FIG. 4 shows the higher G6Pase-a activity achieved by the AAV9 vector bearing the hAAT promoter compared to the AAV9 vector expressing wild-type G6pc in a larger cohort of L.G6pc$^{-/-}$ animals injected at $2.5\times10^{11}$ vg/mouse. The activity assay was performed on liver tissues collected at sacrifice. Statistical analyses were performed by ANOVA (#P<0.05 vs. PBS-injected L.G6pc$^{+/+}$ mice; * P<0.05 vs. PBS-injected L.G6pc$^{-/-}$ mice, X P<0.05 as indicated).

Figure 5:
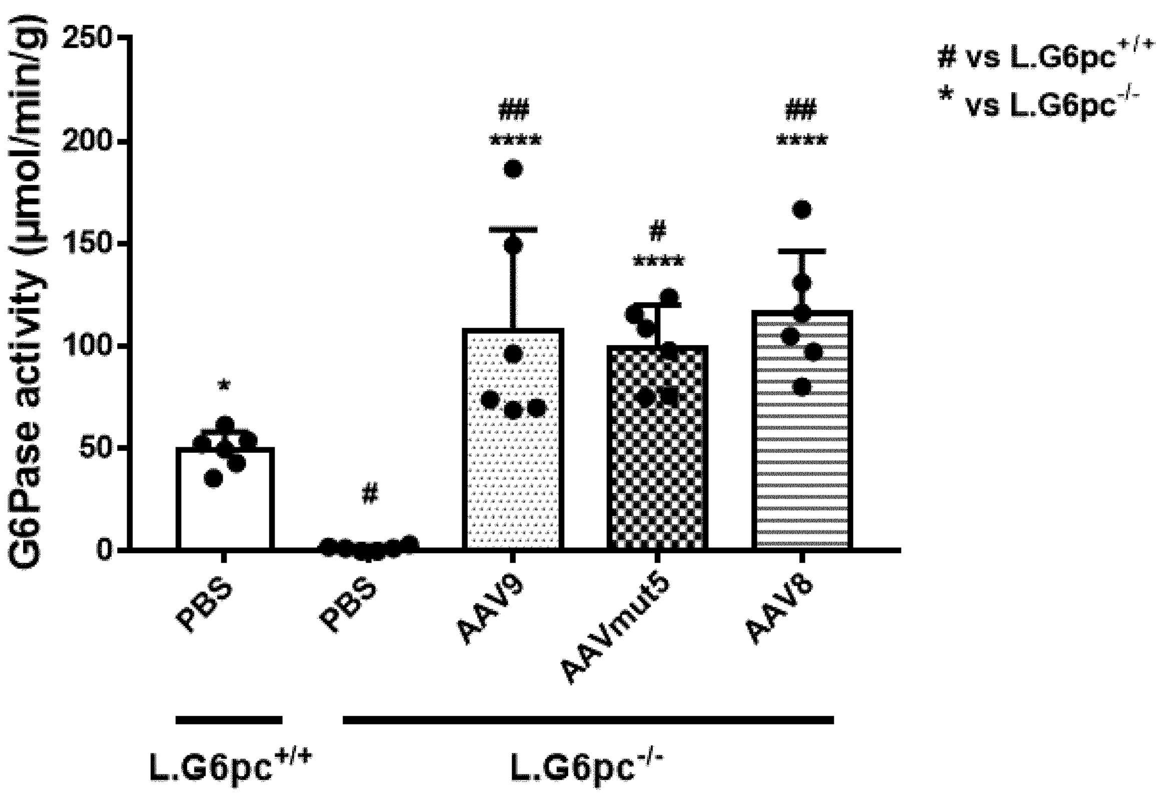

FIG. 5 shows the G6Pase-a activity obtained with different AAV vectors encoding the human G6pc gene injected in L.G6pc$^{-/-}$ mice. PBS-injected L.G6pc$^{+/+}$ and L.G6pc$^{-/-}$ mice were used as controls. The activity assay was performed on liver tissues collected 15 days after vector injection. Statistical analyses were performed by ANOVA (#P<0.05 vs. PBS-injected L.G6pc$^{+/+}$ mice; * P<0.05 vs. PBS-injected L.G6pc$^{-/-}$ mice, +P<0.05 as indicated).

Figure 6:
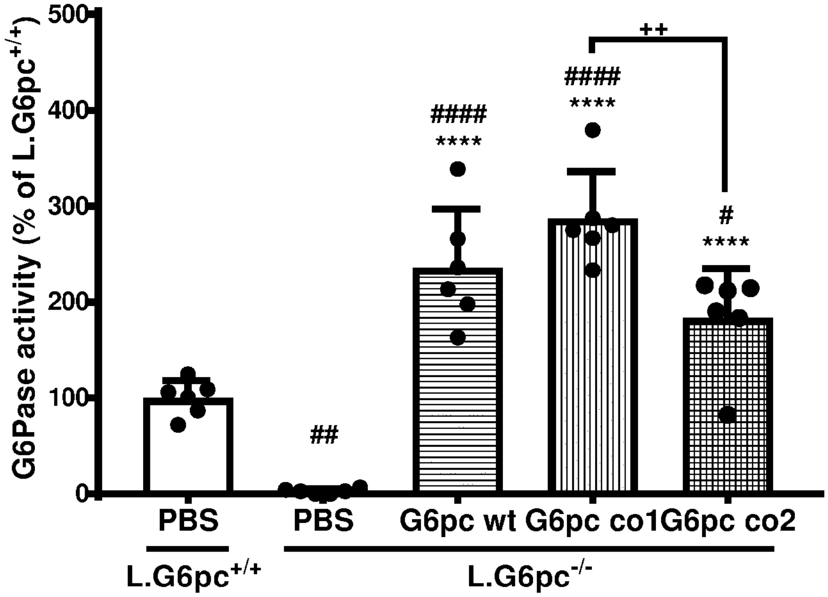
Figure 6:
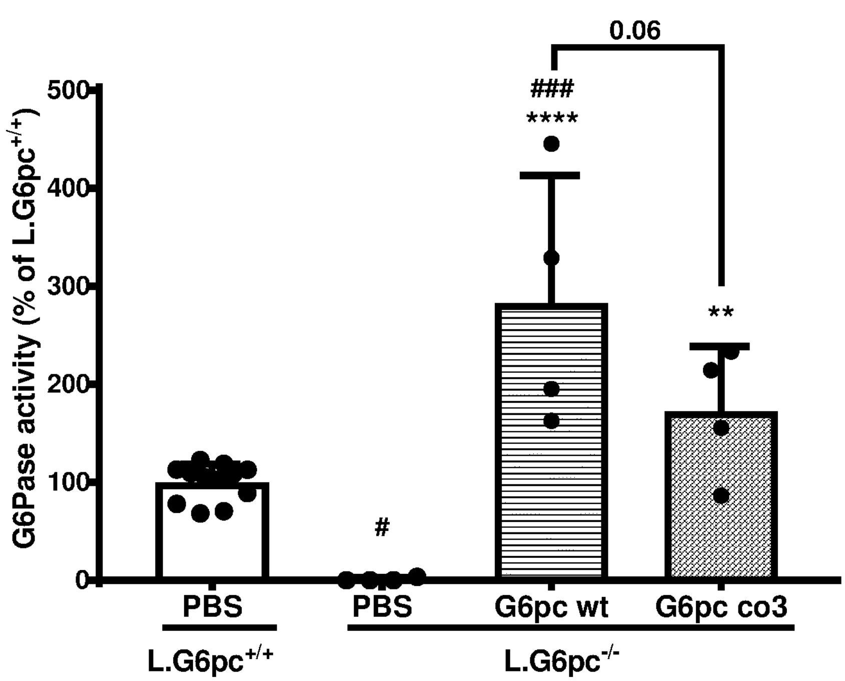

FIG. 6 shows the comparison of the efficacy of three different codon-optimized sequences. A. shows the G6Pase-a activity assay, expressed as percent of L.G6pc$^{+/+}$ G6Pase-a activity, of the wild-type (G6pc wt), codon-optimized 1 and 2 (G6pc co1 and G6pc co2) G6pc sequences expressed with AAV8 in L.G6pc$^{-/-}$ mice injected at a dose of $1\times10^{12}$ vg/kg and followed-up for 15 days. B. shows the G6Pase-a activity assay, expressed as percent of L.G6pc$^{+/+}$ G6Pase-a activity, of the wild-type (G6pc wt) and codon-optimized 3 (G6pc co3) G6pc sequences in L.G6pc$^{-/-}$ mice injected with AAV9 at a dose of $1\times10^{11}$ vg/mouse and followed-up for 15 days. Statistical analyses were performed by ANOVA (#P<0.05 vs. PBS-injected L.G6pc$^{+/+}$ mice; * P<0.05 vs. PBS-injected L.G6pc$^{-/-}$ mice; +P<0.05 as indicated).

DETAILED DESCRIPTION OF THE INVENTION

Definitions

The terms "glucose-6-phosphatase alpha" or "G6Pase-a" relates to an enzyme encoded by the G6pc gene. This enzyme catalyzes the hydrolysis of glucose-6-phosphate (G6P) to glucose and inorganic phosphate in the terminal step of glycogenolysis and gluconeogenesis. According to the invention, G6Pase-a may be a wild-type G6Pase-a or a modified G6Pase-a, in particular a modified G6Pase-a having increased phosphohydrolase activity. Modified G6Pase-a are disclosed in WO2016106303 and [16]. For example, G6Pase-a may be SEQ ID NO: 1, SEQ ID NO: 12, or any the modified G6Pase-a having an amino acid sequence selected from SEQ ID NO: 29 to SEQ ID NO: 44.

According to the present invention, the "identity" is calculated by comparing two aligned sequences in a comparison window. The alignment of the sequences makes it possible to determine the number of positions (nucleotides or amino acids) in common for the two sequences in the comparison window. The number of positions in common is therefore divided by the total number of positions in the comparison window and multiplied by 100 to obtain the percentage of identity. The determination of the percentage of sequence identity can be carried out manually or by means of well-known computer programs. In a particular embodiment of the invention, the identity or the homology corresponds to at least one substitution, for example 1, 2, 3, 4, 5 substitutions, of an amino acid residue, without appreciable loss of interactive binding capacity. Preferably, the at least one substitution is a conservative amino acid substitution. By "conservative amino acid substitution", it is meant that an amino acid can be replaced with another amino acid having a similar side chain. Families of amino acid having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

According to the invention, the term "nucleic acid sequence" refers to a DNA or RNA molecule in single or double stranded form, particularly a DNA.

According to the invention, the term "nucleic acid sequence encoding a G6Pase-a" refers to a nucleic acid sequence encoding a G6Pase-a, either a wild-type G6Pase-a or a modified G6Pase-a. Modified nucleic acid sequence encoding a modified G6Pase-a are disclosed in reference [16] and WO2016106303. For example, a nucleic acid sequence encoding a wild-type G6Pase-a have the nucleotide sequence SEQ ID NO: 2, SEQ ID NO: 3, SEQ ID NO: 45, or SEQ ID NO: 46. For example, a nucleic acid sequence encoding a modified G6Pase-a have the nucleotide sequence SEQ ID NO: 4 or SEQ ID NO: 5. For example, a nucleic acid sequence encoding a G6Pase-a may therefore be SEQ ID NO: 2, SEQ ID NO: 3, SEQ ID NO: 4, SEQ ID NO: 5, SEQ ID NO: 45, SEQ ID NO: 46, or any of the nucleic acid sequences encoding a modified G6Pase-a selected from SEQ ID NO: 13 to SEQ ID NO: 28.

The term "nucleic acid construct" refers to an artificially constructed segment of nucleic acid that is to be transplanted into a target cell for expressing a transgene, e.g. for the expression of a G6Pase-a in a cell. The nucleic acid construct may comprise one or more expression control nucleic acid sequences and/or other nucleic acid sequences improving the expression of G6Pase-a and/or nucleic acid sequences enhancing the secretion of G6Pase-a and/or nucleic acid sequences enhancing the tissue uptake of G6Pase-a, said nucleic acid sequences may be operably linked to the sequence encoding the transgene (e.g. G6Pase-a). As used herein, the term "operably linked" refers to a linkage of polynucleotide elements in a functional relationship. A nucleic acid sequence is "operably linked" when it is placed into a functional relationship with another nucleic acid sequence. For instance, a promoter, or another transcription regulatory nucleic acid sequence, is operably linked to a nucleic acid sequence encoding a transgene (e.g. G6Pase-a) if it affects the transcription of the nucleic acid sequence. Such expression control nucleic acid sequences are known in the art, such as promoters, enhancers (such as cis-regulatory modules (CRMs)), introns, polyA signals, etc.

The term "alpha-1 antitrypsin" or "AAT" relates to a protein belonging to the serpin superfamily. It is encoded in humans by the SERPINA1 gene. The term "hAAT" relates to the human AAT.

The term "promoter" refers to a region of DNA that directs/initiates transcription of a nucleic acid sequence (e.g. a gene). A promoter includes necessary nucleic acid sequences near the start site of transcription. Typically, promoters are located near the genes they transcribe.

The term "hAAT promoter" relates to the promoter of hAAT, either a wild-type hAAT promoter or a modified hAAT promoter.

The term "vector" according to the invention means a vector suitable for a transgene expression in gene therapy, e.g. for G6Pase-a expression in gene therapy.

In the context of the present invention, the term "gene therapy" refers to treatment of a subject which involves delivery of a gene/nucleic acid into an individual's cells for the purpose of treating a disease.

The term "subject", "patient" or "individual", as used herein, refers to a human or non-human mammal (such as a rodent (mouse, rat), a feline, a canine, or a primate) affected or likely to be affected with a glycogen storage disease Ia (GSD-Ia). Preferably, the subject is a human, man or woman.

The term "glycogen storage disease" or "GSD" refers to a metabolic disorder caused by enzyme deficiencies affecting glycogen synthesis, glycogen breakdown or glycolysis, typically within muscles and/or liver cells. GSD is classified in different types, from GSD type 0 to GSD type XV. GSD-I consists of two autosomal recessive disorders, GSD-Ia and GSD-Ib. GSD-Ia results from a deficiency in glucose-6-phosphatase-a. Deficiencies in the glucose-6-phosphate transporter (G6PT) are responsible for GSD-Ib. According to the invention, the GSD is GSD-Ia (von Gierke's disease; OMIM #232240).

The term "treating" or "treatment" means reversing, alleviating, inhibiting the progress of, or preventing the disorder or condition to which such term applies, or one or more symptoms of such disorder or condition. In particular, the treatment of the disorder may consist in treating dysfunctions in GSD, preferably improving the glycaemia control in a subject.

The term "pharmaceutically acceptable" means approved by a regulatory agency of the Federal or a state government or listed in the U.S. or European Pharmacopeia or other generally recognized pharmacopeia for use in animals and Humans.

A "pharmaceutical composition" means a composition comprising pharmaceutically acceptable carrier. For example, a carrier can be a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like. When the pharmaceutical composition is adapted for oral administration, the tablets or capsules can be prepared by conventional means with pharmaceutically acceptable excipients such as binding agents (e.g. pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. The composition according to the invention is preferably a pharmaceutical composition.

Nucleic Acid Construct

The description relates to a nucleic acid construct for the expression of a glucose-6-phosphatase (G6Pase-a) in a cell, the construct comprising a nucleic acid sequence encoding the G6Pase-a, wherein the nucleic acid sequence encoding the G6Pase-a is operably linked to a human alpha-1 antitrypsin (hAAT) promoter.

According to the description, the nucleic acid sequence may encode a wild-type G6Pase-a, e.g. the G6Pase-a having the amino acid sequence SEQ ID NO: 1, or a modified G6Pase-a, preferably a modified G6Pase-a having increased phosphohydrolase activity, e.g. a G6Pase-a comprising or having an amino acid sequence at least 90% identical to SEQ ID NO: 1. The modified G6Pase-a can include one or more amino acid modification(s), such as substitution or deletion, so long as the protein retains enzymatic activity. In some embodiments, the modified G6Pase-a comprises a serine to cysteine substitution at amino acid 298 of human G6Pase-a (the amino acid sequence of wild type human G6Pase-a is set forth herein as SEQ ID NO: 1). The modified G6Pase-a can include modifications at other residues so long as the protein retains enzymatic activity. For example, the modified G6Pase-a can include substitutions at other residues, such residues include positions 3, 54, 139, 196, 199, 242, 247, 292, 301, 318, 324, 332, 347, 349, 350 and/or 353 of the human G6Pase-a (set forth as SEQ ID NO: 1). Modified G6Pase-a are disclosed in WO2016/106303 and [16]. For example, G6Pase-a may be SEQ ID NO: 1, SEQ ID NO: 12, or any modified G6Pase-a having an amino acid sequence selected from SEQ ID NO: 29 to SEQ ID NO: 44.

The G6Pase-a may comprise or may have an amino acid sequence at least 90%, at least 91%, at least 92%, at least 93%, at least 94%, at least 95%, at least 96%, at least 97%, at least 98%, at least 99%, or 100% identical to SEQ ID NO: 1.

The nucleic acid sequence encoding the G6Pase-a may therefore encode either a wild-type G6Pase-a (SEQ ID NO: 2, SEQ ID NO: 3, SEQ ID NO: 45, or SEQ ID NO: 46, preferably SEQ ID NO: 45) or a modified G6Pase-a. Nucleic acid sequence encoding a modified G6Pase-a may be any of the nucleic acid sequences selected from SEQ ID NO: 4, SEQ ID NO: 5, any of SEQ ID NO: 13 to SEQ ID NO: 28, SEQ ID NO: 52, or SEQ ID NO: 54.

The nucleic acid sequence encoding the G6Pase-a may comprise a nucleotide sequence having at least 90%, at least 91%, at least 92%, at least 93%, at least 94%, at least 95%, at least 96%, at least 97%, at least 98%, at least 99%, or 100% identity with SEQ ID NO: 2.

For example, a nucleic acid sequence encoding a G6Pase-a may therefore be SEQ ID NO: 2, SEQ ID NO: 3, SEQ ID NO: 4, or any of nucleic acid sequences n°6-7 of WO2016106303.

The nucleic acid sequence encoding the G6Pase-a may comprise a nucleotide sequence having at least 90%, at least 91%, at least 92%, at least 93%, at least 94%, at least 95%, at least 96%, at least 97%, at least 98%, at least 99%, or 100% identity with SEQ ID NO: 45.

The nucleic acid sequence encoding the G6Pase-a may comprise a nucleotide sequence having at least 90%, at least 91%, at least 92%, at least 93%, at least 94%, at least 95%, at least 96%, at least 97%, at least 98%, at least 99%, or 100% identity with SEQ ID NO: 46.

The nucleic acid sequence encoding a G6Pase-a is operably linked to a human alpha-1 antitrypsin (hAAT) promoter.

The hAAT promoter may be a wild-type hAAT promoter, e.g. the hAAT promoter having the nucleic acid sequence SEQ ID NO: 8, or a modified hAAT promoter, e.g. a hAAT promoter comprising or having a nucleic acid sequence at least 90% identical to SEQ ID NO: 8. The modified hAAT promoter can include one or more nucleic acid modification(s), such as substitution or deletion, so long as the promoter still directs/initiates transcription of the G6Pase-a.

The hAAT promoter may comprise or may have a nucleotide sequence having at least 90%, at least 91%, at least 92%, at least 93%, at least 94%, at least 95%, at least 96%, at least 97%, at least 98%, at least 99%, or 100% identity with SEQ ID NO: 8.

The hAAT promoter is preferably preceded by an enhancer, such as ApoE enhancer (e.g. SEQ ID NO: 9). For example, the nucleic acid construct comprises SEQ ID NO: 7.

The nucleic acid construct may comprise an intron, in particular an intron placed between the hAAT promoter and the nucleic acid sequence encoding a G6Pase-a. An intron may be introduced to increase mRNA stability and the production of G6Pase-a. Advantageously, the nucleic acid construct comprises an intron derived from the human β globin gene (e.g. HBB2) placed between the hAAT promoter and the nucleic acid sequence encoding a G6Pase-a, preferably the intron comprised in the nucleic acid construct has the sequence shown in SEQ ID NO: 47. The intron having the sequence SEQ ID NO: 47 is disclosed in WO2015/162302. Alternatively, the intron is placed after the 3'-end of the nucleic acid sequence encoding a G6Pase-a.

The nucleic acid construct of the description may comprise, in the 5' to 3' orientation, the hAAT promoter optionally preceded by an enhancer, such as ApoE enhancer (e.g. SEQ ID NO: 9), optionally an intron, such as an intron of the human β globin gene (e.g. SEQ ID NO: 47), the nucleic acid sequence encoding the G6Pase-a and a polyadenylation signal (such as the bovine growth hormone polyadenylation signal, the HBB2 polyadenylation signal, the SV40 polyadenylation signal, or another naturally occurring or artificial polyadenylation signal). Advantageously, the nucleic acid construct of the invention comprises, in the 5' to 3' orientation, the hAAT promoter optionally preceded by an enhancer, such as ApoE enhancer (e.g. SEQ ID NO: 9), an intron (in particular an intron as defined above), a nucleic acid molecule encoding the G6Pase-a, and a polyadenylation signal.

The nucleic acid construct may comprise or may have a nucleotide sequence having at least 90%, at least 91%, at least 92%, at least 93%, at least 94%, at least 95%, at least 96%, at least 97%, at least 98%, at least 99%, or 100% identity with SEQ ID NO: 11, with SEQ ID NO: 48, with SEQ ID NO: 49, with SEQ ID NO: 50, with SEQ ID NO: 51, with SEQ ID NO: 53, or with SEQ ID NO: 55, or with SEQ ID NO: 56. In a preferred embodiment, the nucleic acid construct may comprise or may have a nucleotide sequence having at least 90%, at least 91%, at least 92%, at least 93%, at least 94%, at least 95%, at least 96%, at least 97%, at least 98%, at least 99%, or 100% identity with SEQ ID NO: 48.

The term nucleic acid construct is to be transferred into a target cell for the expression of a G6Pase-a in said cell. Preferably, said target cell is a liver cell, a kidney cell or an intestinal cell.

Vector

The terms "nucleic acid construct of the description" or "nucleic acid construct according to the description" means the nucleic acid construct disclosed in the present description, particularly the nucleic acid construct disclosed above.

The description also relates to a vector comprising the nucleic acid construct of the description.

The vector may be a plasmid vector. The vector may also be a nanoparticle containing the nucleic acid construct of the invention. The vector may also be a system based on transposons, allowing integration of the nucleic acid construct of the invention in the genome of the target cell, such as the hyperactive Sleeping Beauty (SB100X) transposon system [2]. The vector may be a viral vector suitable for gene therapy. The vector may target any cell of interest such as liver cells, kidney cells or intestinal cells.

The vector may be a viral vector, such as lentiviral vector or adeno-associated virus (AAV) vector.

The invention relates to an AAV vector comprising the nucleic acid construct of the description. In a particularly preferred embodiment, the AAV vector implemented in the practice of the present invention is AAV8 or AAV9, preferably AAV8.

Thus, the nucleic acid construct of the description may also contain sequences suitable for producing an efficient viral vector, as it is well disclosed in the art.

The nucleic acid construct may be inserted in the vector, such as a lentiviral vector according to the description, or an AAV vector according to the invention, such as a single-stranded or double-stranded self-complementary AAV vector. In a much preferred embodiment of the present invention, the AAV vector is an AAV vector suitable for transducing liver cells, more particularly an AAV-1, AAV-2 and AAV-2 variants (such as the quadruple-mutant capsid optimized AAV-2 comprising an engineered capsid with Y44+500+730F+T491V changes, disclosed in [3]), AAV-3 and AAV-3 variants (such as the AAV3-ST variant comprising an engineered AAV-3 capsid with two amino acid changes, S663V+T492V, disclosed in Vercauteren et al. [4], AAV-3B and AAV-3B variants, AAV-4, AAV-5, AAV-6 and AAV-6 variants (such as the AAV-6 variant comprising the triply mutated AAV-6 capsid Y731F/Y705F/T492V form disclosed in [5], AAV-7, AAV-8, AAV-9, AAV-10 such as AAV-cy10 and AAV-rh10, AAV-rh74, AAV-dj, Anc80, LK03, AAV-2i8, porcine AAV serotypes such as AAV-po4 and AAV-po6, etc., As it is known in the art, depending on the specific viral vector considered for use, additional suitable sequences will be introduced in the nucleic acid construct of the description for obtaining a functional viral vector. Suitable sequences include AAV ITRs for an AAV vector, or LTRs for lentiviral vectors. As such, the description also relates to a nucleic acid construct as described above, flanked by an ITR or an LTR on each side.

In addition, other non-natural engineered variants and chimeric AAV can also be useful. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus. Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. AAV-based recombinant vectors lacking the Rep protein integrate with low efficacy into the host's genome and are mainly present as stable circular episomes that can persist for years in the target cells. Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

In the context of the present invention, the AAV vector comprises an AAV capsid able to transduce the target cells of interest, in particular hepatocytes. In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype.

According to a particular embodiment, the AAV capsid is selected from AAV-1, -2, AAV-2 variants (such as the quadruple-mutant capsid optimized AAV-2 comprising an engineered capsid with Y44+500+730F+T491V changes, disclosed in Ling et al., 2016, -3 and AAV-3 variants (such as the AAV3-ST variant comprising an engineered AAV3 capsid with two amino acid changes, S663V+T492V, disclosed in Vercauteren et al., 2016, -3B and AAV-3B variants, -4, -5, -6 and AAV-6 variants (such as the AAV6 variant comprising the triply mutated AAV6 capsid Y731F/Y705F/T492V form disclosed in Rosario et al., 2016), -7, -8, -9 and AAV-9 variants (such as AAVhu68), -2G9, -10 such as -cy10 and -rh10, -rh39, -rh43, -rh74, -dj, Anc80, LK03, AAV.PHP, AAV2i8, porcine AAV such as AAVpo4 and AAVpo6, and tyrosine, lysine and serine capsid mutants of AAV serotypes. In addition, the AAV capsid is selected from other non-natural engineered variants (such as AAV-spark100), chimeric AAV or AAV serotypes obtained by shuffling, rationale design, error prone PCR, and machine learning technologies. In a particular embodiment, the Cap gene encodes VP capsid proteins derived from at least two different AAV serotypes, or encodes at least one chimeric VP protein combining VP protein regions or domains derived from at least two AAV serotypes. For example a chimeric AAV capsid can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants. In a particular embodiment, the capsid of the AAV vector is a hybrid between AAV serotype 9 (AAV9) and AAV serotype 74 (AAVrh74) capsid proteins. For example, the AAV serotype may be a -rh74-9 serotype as disclosed in WO2019/193119 (such as the Hybrid Cap rh74-9 serotype described in examples of WO2019/193119; a rh74-9 serotype being also referred to herein as "-rh74-9", "AAVrh74-9" or "AAV-rh74-9") or a -9-rh74 serotype as disclosed in WO2019/193119 (such as the Hybrid Cap 9-rh74 serotype described in the examples of WO2019/193119; a -9-rh74 serotype being also referred to herein as "–9-rh74", "AAV9-rh74", "AAV-9-rh74", or "rh74-AAV9"). For example, the capsid of the AAV vector is a peptide-modified hybrid between AAV serotype 9 (AAV9) and AAV serotype 74 (AAVrh74) capsid proteins, as described in PCT/EP2019/076958, such as an AAV9-rh74 hybrid capsid or AAVrh74-9 hybrid capsid modified with the P1 peptide described in the examples of PCT/EP2019/076958For another example, the AAV serotype may be a hybrids AAV2/13 as disclosed in PCT/EP2020/061380.

For example, the genome of the pseudotyped vector may have a capsid derived from the AAV8, AAV9, AAVrh74 or AAV2i8 serotype, and its genome may be derived from and different serotype. In a particular embodiment, the AAV vector has a capsid of the AAV8, AAV9 or AAVrh74 serotype, in particular of the AAV8 or AAV9 serotype, more particularly of the AAV8 serotype.

In a specific embodiment, the vector is the vector referred to "AAV8mut5". AAV8mut5 vector has the amino acid sequence SEQ ID NO: 57 and is encoded by the polynucleotide of SEQ ID NO: 58.

In a specific embodiment, wherein the vector is for use in delivering the transgene to muscle cells, the AAV vector may be selected, among others, in the group consisting of AAV8, AAV9 and AAVrh74.

In another specific embodiment, wherein the vector is for use in delivering the transgene to liver cells, the AAV vector may be selected, among others, in the group consisting of AAV5, AAV8, AAV9, AAV-LK03, AAV-Anc80 and AAV3B.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in [6] and in [7]. For example a chimeric AAV vector can derive from the combination of an AAV8 or AAV9 capsid sequence with a sequence of an AAV serotype different from the AAV8 or AAV9 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in [8], or in [9]. In addition, capsid variants may include single amino acid changes such as tyrosine mutants (e.g. as described in [10]). Another example is the fusion of Anthopleurin-B to the N-terminus of AAV VP2 capsid protein described in [11].

In addition, the genome of the AAV vector may either be a single stranded or self-complementary double-stranded genome [12]. Self-complementary double-stranded AAV vectors are generated by deleting the terminal resolution site (trs) from one of the AAV terminal repeats. These modified vectors, whose replicating genome is half the length of the wild type AAV genome, have the tendency to package DNA dimers.

In a preferred embodiment, the AAV vector implemented in the practice of the present invention has a single stranded genome, and further preferably comprises an AAV8, AAV9, AAVmut5, AAVrh74 or AAV2i8 capsid, in particular an AAV8, AAV9 or AAVrh74 capsid, such as an AAV8 or AAV9 capsid, more particularly an AAV8 capsid.

Cell

The terms "vector of the description" or "vector according to the description" means the vector disclosed in the present description, particularly the vector disclosed above.

The description relates to a cell transformed with the nucleic acid molecule of the description or the vector according to the description.

The invention relates to a cell transformed with the AAV vector of the invention.

For example, the host cell can be a cell (or cell line) appropriate for production of the vector, e.g. for production of AAV. In some examples, the host cell is a mammalian cell, such as a HEK-293, BHK, Vero, RD, HT-1080, A549, Cos-7, ARPE-19, or MRC-5 cell.

The host cell can also be a cell which is the target for a gene therapy, such as a liver cell, a kidney cell or an intestinal cell.

In some embodiments, the cell is an isolated cell.

Composition

The terms "cell of the description" or "cell according to the description" means the cell disclosed in the present description, particularly the cell disclosed above.

The description relates to a composition comprising the nucleic acid construct of the description, the vector of the description, or the cell of the description. The composition of the description is preferably a pharmaceutical composition.

The invention relates to a composition comprising the vector of the invention or the cell of the invention. The composition of the invention is preferably a pharmaceutical composition.

The composition can take the form of solutions, suspensions, emulsions, tablets, pills, capsules, powders, sustained-release formulations and the like.

Such composition will contain a therapeutically effective amount of the nucleic acid construct of the invention, of the vector of the invention, or of the cell of the invention, preferably in purified form, together with a suitable amount of carrier so as to provide the form for proper administration to the subject. In a particular embodiment, the nucleic acid construct, vector or cell of the invention is formulated in a composition comprising phosphate-buffered saline and supplemented with 0.25% human serum albumin. In another particular embodiment, the nucleic acid construct, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792.

In a preferred embodiment, the composition is formulated in accordance with routine procedures as a pharmaceutical composition adapted for intravenous or intrathecal administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

Method of Treatment

The terms "composition of the description" or "composition according to the description" means the composition disclosed in the present description, particularly the composition disclosed above.

The description relates to the nucleic acid construct of the description, the vector of the description, the cell of the description or the composition of the description, for use as a medicament.

The description also relates to the nucleic acid construct of the description, the vector of the description, the cell of the description or the composition of the description, for use in the treatment of glycogen storage disease Ia (GSD-Ia).

The invention relates to the vector of the invention, the cell of the invention or the composition of the invention, for use as a medicament.

The invention also relates to the vector of the invention, the cell of the invention or the composition of the invention, for use in the treatment of glycogen storage disease Ia (GSD-Ia).

The nucleic acid construct, the vector, the cell or the composition of the invention may be administered to a subject by any effective route. Exemplary routes of administration include, but are not limited to, injection (such as subcutaneous, intramuscular, intradermal, intraperitoneal, intrathecal, and intravenous), oral, intraductal, sublingual, rectal, transdermal, intranasal, vaginal and inhalation routes.

The nucleic acid construct, the vector, the cell or the composition may be administered to a subject in a therapeutically effective amount, i.e. in an amount sufficient to achieve the desired effect in a subject, or in the cell, being treated. The effective amount of the nucleic acid construct, the vector, the cell or the composition will be dependent on several factors, including, but not limited to the subject or cells being treated, and the manner of administration.

The amount of the therapeutic (i.e. a nucleic acid construct, vector or cell) which will be effective in the treatment of a disease, such as GSD-Ia, can be determined by standard clinical techniques. In addition, in vivo and/or in vitro assays may optionally be employed to help predict optimal dosage ranges. The precise dose to be employed in the composition will also depend on the route of administration, and the seriousness of the disease, and should be decided according to the judgment of the practitioner and each patient's circumstances. The dosage of the nucleic acid, the vector or the cell administered to the subject in need thereof will vary based on several factors including, without limitation, the route of administration, the specific disease treated, the subject's age or the level of expression necessary to require the therapeutic effect. One skilled in the art can readily determine, based on its knowledge in this field, the dosage range required based on these factors and others. In case of a treatment comprising administering a viral vector, such as an AAV vector, to the subject, typical doses of the vector are of at least $1\times10^{8}$ vector genomes per kilogram body weight (vg/kg), such as at least $1\times10^{9}$ vg/kg, at least $1\times10^{10}$ vg/kg, at least $1\times10^{11}$ vg/kg, at least $1\times10^{12}$ vg/kg, at least $1\times10^{13}$ vg/kg, or at least $1\times10^{14}$ vg/kg.

The therapeutic (i.e. a nucleic acid construct, vector or cell) of the invention can be administered in a single dose, or in multiple doses (such as 2, 3, 4, 5, 6, 7, 8, 9 or 10 doses) as needed for the desired therapeutic results.

G6Pase-a Codon Optimized

The nucleic acid sequence encoding a G6Pase-a may be optimized for expression of the G6Pase-a in vivo. Sequence optimization may include a number of changes in a nucleic acid sequence, including codon optimization, increase of GC content, decrease of CG dimers, decrease of the number of CpG islands, decrease of the number of alternative open reading frames (ARFs) and/or decrease of the number of splice donor and splice acceptor sites. Because of the degeneracy of the genetic code, different nucleic acid molecules may encode the same protein. It is also well known that the genetic codes of different organisms are often biased towards using one of the several codons that encode the same amino acid over the others. Through codon optimization, changes are introduced in a nucleotide sequence that take advantage of the codon bias existing in a given cellular context so that the resulting codon optimized nucleotide sequence is more likely to be expressed in such given cellular context at a relatively high level compared to the non-codon optimized sequence. Of course, as is well known to those skilled in the art, sequence optimization is a balance between all these parameters, meaning that a sequence may be considered optimized if at least one of the above parameters is improved while one or more of the other parameters is not, as long as the optimized sequence leads to an improvement of the transgene, such as an improved expression and/or a decreased immune response to the transgene in vivo.

The nucleic acid sequence encoding a G6Pase-a may be codon-optimized to improve its expression in human cells compared to non-codon optimized nucleotide sequences coding for the same G6Pase-a. A wild type nucleic acid sequence encoding a wild type G6Pase-a is as shown in SEQ ID NO: 2. Examples of codon optimized sequences encoding the same G6Pase-a are as shown in SEQ ID NO: 3, SEQ ID NO: 45 or SEQ ID NO: 46. Other examples of sequence optimized nucleic acid encoding a modified G6Pase-a are SEQ ID NO: 5, SEQ ID NO: 52 and SEQ ID NO: 54 encoding the modified G6Pase of SEQ ID NO: 12, all optimized with respect to one of the above parameters compared to the nucleic acid sequence of SEQ ID NO: 4.

The nucleic acid sequence of the invention encoding a G6Pase may be codon optimized and/or may have a decreased GC content and/or has a decreased number of CG dimers as compared to the wild type nucleotide sequence encoding the same G6Pase-a amino acid sequence such as the G6Pase-a of SEQ ID NO: 1. The nucleic acid sequence encoding a G6Pase may also be codon optimized and/or may have a decreased GC content and/or has a decreased number of CG dimers compared to the nucleotide sequence of SEQ ID NO: 2. Alternatively, such nucleic acid sequence encoding a G6Pase may have the sequence of SEQ ID NO: 45 or SEQ ID NO: 46, preferably SEQ ID NO: 45.

The present description also discloses a nucleic acid sequence encoding a G6Pase-a comprising a nucleotide sequence having at least 90%, at least 91%, at least 92%, at least 93%, at least 94%, at least 95%, at least 96%, at least 97%, at least 98%, at least 99%, or 100% identity with SEQ ID NO: 45.

The present description also discloses a nucleic acid construct for the expression of a G6Pase-a in a cell, the construct comprising a nucleic acid sequence encoding the G6Pase-a, wherein the nucleic acid sequence encoding a G6Pase-a comprises a nucleotide sequence having at least 90%, at least 91%, at least 92%, at least 93%, at least 94%, at least 95%, at least 96%, at least 97%, at least 98%, at least 99%, or 100% identity with SEQ ID NO: 45. The nucleic acid sequence encoding the G6Pase-a is preferably operably linked to a promoter.

The present description also discloses a vector comprising the nucleic acid construct disclosed in this section (i.e. in section "G6Pase-a codon optimized"). The vector may be a lentiviral vector or an adeno-associated virus (AAV) vector, such as AAV8, AAV9 or AAVmut5, preferably AAV8.

The present description also discloses a cell transformed with the nucleic acid molecule disclosed in this section or the vector disclosed in this section. The cell may be a liver cell, an intestinal cell or a kidney cell.

The present description also discloses a composition comprising the nucleic acid construct, the vector, or the cell disclosed in this section.

The present description also discloses the nucleic acid construct, the vector, the cell or the composition disclosed in this section, for use as a medicament.

The present description also discloses the nucleic acid construct, the vector, the cell or the composition disclosed in this section, for use in the treatment of glycogen storage disease Ia (GSD-Ia).

EXAMPLES

Materials and Methods

In Examples 1, 2 and 3, we have prepared two nucleic acid constructs (hereafter "transgene expression cassettes") comprising the human G6pc gene wt (SEQ ID NO: 2) encoding G6Pase-a, under the control of different promoters:

- The alpha-1-anti-trypsin (hAAT) promoter. The nucleic acid sequence of the expression cassette is SEQ ID NO: 11.
- The endogenous promoter of the human G6pc gene (hGPE). The nucleic acid sequence of the expression cassette is SEQ ID NO: 10.

The transgene expression cassettes are represented in FIG. 1A.

The two transgene expression cassettes were pseudotyped in AAV9 to obtain two different AAV vectors, namely AAV9-hAAT-hG6PC and AAV9-hGPE-hG6PC.

The two vectors or PBS (negative control) were independently tested in a liver-specific G6pc knockout mouse model (L.G6pc−/−, [13]), i.e. GSD-Ia mice. As a positive control, WT mice (L.G6pc+/+) were infused with PBS.

In Example 4, we have prepared a nucleic acid construct (hereafter "transgene expression cassettes") comprising the human G6pc gene wt (SEQ ID NO: 2) encoding G6Pase-a, under the control of the alpha-1-anti-trypsin (hAAT) promoter. The nucleic acid sequence of the expression cassette was SEQ ID NO: 56.

The expression cassette for human G6pc gene wt was pseudotyped in AAV9, AAV8 and AAVmut5.

The three vectors or PBS (negative control) were independently tested in a liver-specific G6pc knockout mouse model (L.G6pc−/−, [13]), i.e. GSD-Ia mice. As a positive control, WT mice (L.G6pc+/+) were infused with PBS.

In Example 5, we have prepared four nucleic acid constructs (hereafter "transgene expression cassettes") comprising the human G6pc gene wt (SEQ ID NO: 2) and two codon optimized human G6pc gene (co1, co2 and co3, respectively SEQ ID NO: 45, SEQ ID NO: 46 and SEQ ID NO: 3), each encoding G6Pase-a, under the control of the alpha-1-anti-trypsin (hAAT) promoter.

The nucleic acid sequence of the expression cassette for human G6pc gene wt was SEQ ID NO: 11 or SEQ ID NO: 56. The nucleic acid sequence of the expression cassettes for human G6pc gene co1, human G6pc gene co2 and human G6pc gene co3 were respectively SEQ ID NO: 48, SEQ ID NO: 49 and SEQ ID NO: 50.

The expression cassette for human G6pc gene wt was pseudotyped in AAV8 (SEQ ID NO: 56) and AAV9 (SEQ ID NO: 11).

The expression cassettes for human G6pc gene co1 and G6pc gene co2 were pseudotyped in AAV8.

The expression cassette for human G6pc gene co3 was pseudotyped in AAV9.

The five vectors or PBS (negative control) were independently tested in a liver-specific G6pc knockout mouse model (L.G6pc−/−, [13]), i.e. GSD-Ia mice. As a positive control, WT mice (L.G6pc+/+) were infused with PBS.

In Vivo Studies

Mice were fed either a standard chow diet (A04 diet, Safe) or a high fat/high sucrose diet (made by INRAE, Jouy en Josas), known to accelerate hepatic tumor development in L.G6pc−/− mice. Proneness to tumor formation was induced in mice by feeding them with a modified chow diet composed of 36% fat (INRA) [14].

AAV vectors were administered intravenously via the tail vein of L.G6pc−/− mice. Wild type mice (C57Bl/6J mice, Charles Rivers) were injected with PBS via the tail vein. Glycemia was measured on peripheral blood after a 6-hour fasting using a glucometer (Roche Diagnostic). At sacrifice, livers were harvested and weighed to measure the liver/body weight ratio and snap-frozen for further evaluations.

Tumors were evaluated in GSDIa mice at sacrifice by visual inspection. Only tumors larger than 2 mm were considered in the count.

AAV Production

HEK293T cells were grown in suspension in 250 ml of serum-free medium. The cells were transfected with 3 plasmids: i) a transgene plasmid, containing AAV2 ITRs flanking an expression cassette ii) the helper plasmid pXX6, containing adenoviral sequences necessary for AAV production, and iii) a plasmid containing AAV Rep and Cap genes, defining the serotype of AAV. Two days after transfection, the cells were lysed to release the AAV particles.

The viral lysate was purified by affinity chromatography. Viral genomes were quantified by a TaqMan real-time PCR assay using primers and probes corresponding to the ITRs of the AAV vector genome [17].

G6Pase Enzyme Activity Measurement

G6Pase enzyme activity was measured in homogenates from freeze-clamped livers as already reported in [13]. Briefly, tissues homogenates were incubated with glucose-6-phosphate (Sigma) for fifteen minutes at 37° C. The reaction was stopped by adding trichloroacetic acid and the released phosphate was measured by complexation with ammonium molybdate and citrate arsenite. The resulting absorbance was measured on at 700 nm.

Measurement of Glycogen Content

Glycogen content was measured indirectly in tissue homogenates as the glucose released after total digestion with *Aspergillus Niger* amyloglucosidase (Sigma). Samples were incubated for 20 min at 95° C. in the presence of 0.3 M NaOH and then cooled at 4° C. Samples were then added with amyloglucosidase and incubated at 37° C. for 90 minutes. The glucose released was determined with a commercial glucose assay kit.

Vector Genome Copy Number (VGCN) Quantification

For vector genome copy number (VGCN) quantification in samples, DNA was extracted from samples using KingFisher (Thermo Fisher Scientific). Real-time PCR was performed on 1 μL of DNA, using the protocol for AAV vectors titration described above. Exon Mex5 of titin gene was used as genomic DNA loading control.

Example 1: Correction of the Liver Phenotype in GSD-Ia Mice 15 Days after Intravenous Injection of AAV Vectors Expressing Human G6Pase-a The two AAV9 vectors were independently injected in L.G6pc$^{-/-}$ mice fed a standard diet at the dose of $1\times10^{11}$ vg/mouse (FIG. 1A).

Fifteen days after vectors injection, the concentration of glucose in the blood was measured after 6 hours of fasting. Glycaemia was completely normalized in mice injected with the two vectors (FIG. 1B).

G6PC activity was then measured in liver. The AAV9-hAAT-hG6PC vector achieved supraphysiological activity and showed the highest activity when compared to AAV9-hGPE-hG6PC vector (FIG. 1C).

Glycogen concentration was also measured. Complete correction of glycogen accumulation and hepatomegaly was obtained with the AAV9-hAAT-hG6PC but not with the vector bearing the hGPE promoter (FIG. 1D, E respectively), reflecting the higher G6Pase activity achieved in mice treated with the AAV9 vector bearing hAAT promoter. The similar vector genome copy numbers per diploid genome measured in mice injected with the two AAV vectors (FIG. 1F) indicates a similar transduction efficacy in liver.

Example 2: Long-Term Correction of the Liver Phenotype in GSD-Ia Mice after

Intravenous Injection of AAV Vectors Expressing Human G6Pase-a

To assess the long-term efficacy of the two vectors, we performed a 7-months study. Vectors were injected in L.G6pc$^{-/-}$ mice fed a standard diet at a dose of $2.5\times10^{11}$ vg/mouse (FIG. 2A). Seven months after vectors injection, the concentration of glucose in the blood was measured after 6 hours of fasting. Glycemia was corrected in all the animals who received the G6PC-expressing vectors (FIG. 2B). Importantly, L.G6pc$^{-/-}$ mice treated with AAV9-hAAT-hG6PC showed supraphysiological liver G6Pase-a activity that was significantly higher of the activity measured in AAV9-hGPE-hG6PC-treated L.G6pc$^{-/-}$ mice (FIG. 2C).

Glycogen accumulation and hepatomegaly were completely rescued in animals injected with the two vectors (FIG. 2D, E). Higher vector genome copy numbers per diploid genome were measured in mice injected with the AAV9-hGPE-hG6PC vector (FIG. 2F) possibly reflecting a slightly lower liver transduction achieved with the AAV9-hAAT-hG6PC vector.

Taken together, these results indicate that G6Pase-a expression is increased with the hAAT promoter. Thus, hAAT promoter is suitable for AAV gene therapy for GSD-Ia with a potency superior to the hGPE promoter.

Example 3: HGPE-Directed Gene Therapy Promotes Hepatic Tumor Formation in L.G6pc−/− Mice Fed a High Fat/High Sucrose Diet Adenoma formation is one of the hallmarks of GSD-Ia in humans, reported in most of the affected individuals in the second and third decades of life. In L.G6pc$^{-/-}$ mice, almost all the mice fed a standard diet developed liver adenomas by 18 months of age [13]. This slow process can be accelerated by high fat/high sucrose (HF/HS) diet. Approximately 85% of L.G6pc$^{-/-}$ mice fed a HF/HS diet developed multiple hepatic tumors at nine months of age [14]. Thus, L.G6pc$^{-/-}$ mice fed with HF/HS diet represent a robust model to evaluate the efficacy and the safety of gene replacement strategies in the prevention of tumors formation in GSDIa.

We therefore tested the AAV9-hAAT-hG6PC and the AAV9-hGPE-hG6PC vectors in L.G6pc−/− mice fed a HF/HS diet (FIG. 3A). Eight months after treatment, only the vector bearing the hAAT promoter completely rescued glycemia (FIG. 3B). Under HF/HS diet, the levels of G6Pase activity in AAV-treated animals were significantly lower than those measured in L.G6pc$^{+/+}$ animals. Although AAV9-hAAT-hG6PC-treated animals showed higher G6Pase activity levels, statistical significance was not reached when compared to L.G6pc$^{-/-}$ mice treated with AAV9-hGPE-hG6PC vector (FIG. 3C). Similar vector genome copies per diploid genome were measured in AAV-treated mice (FIG. 3D).

Interestingly, necropsy of the mice revealed a higher number of tumors in the livers of mice treated with the hGPE-bearing AAV vectors compared to those that received the AAV9-hAAT-hG6PC (FIG. 3E). These results suggest that the use of AAV9-hAAT-hG6PC may decrease the transformation rate of hepatocytes thus resulting in a decreased frequency of adenomas compared to AAV9-hGPE-hG6PC.

The data obtained for FIG. 3A were completed to increase the number of mice per group (FIG. 4 and Table 1). FIG. 4 shows that, in a larger cohort, the hAAT driven vector achieved a significatively higher G6Pase activity. The data presented in Table 1 confirm that the use of AAV9-hAAT-hG6PC resulted in a decreased frequency of adenomas compared to AAV9-hGPE-hG6PC.

TABLE 1 frequency of adenomas

| | L. G6pc$^{+/+}$ PBS | L. G6pc$^{-/-}$ PBS | hAAT | hGPE |
|---|---|---|---|---|
| Total number of mice | 24 | 17 | 17 | 18 |
| Number of mice that developped macroscopic tumors (%) | 2 (8%) | 5 (29%) | 2 (12%) | 5 (28%) |

Example 4: Expression of G6Pase Wt in Murine Liver with Different AAV Serotypes We produced three different AAV vectors, namely AAV9, AAV8, AAVmut5 expressing wild-type human G6pc gene wt (SEQ ID NO: 2) under the control of the hAAT promoter.

The three vectors or PBS (negative control) were independently tested in a liver-specific G6pc knockout mouse model (L.G6pc$^{-/-}$, [13]), i.e. GSD-Ia mice at the dose of $1\times10^{12}$ vg/kg. As a positive control, WT mice (L.G6pc$^{+/+}$) were infused with PBS. Fifteen days after vector infusion, G6Pase activity was assessed for each vector in liver. The three AAV vector-injected groups showed a similar G6Pase activity with levels higher than those measured in wild-type animals (FIG. 5) thus confirming the possibility to express the transgene in the mouse liver through different AAV vectors.

Example 5: Expression of G6Pase in Murine Liver with Different Codon-Optimized G6pc Sequences We performed two independent experiments to evaluate the efficacy of codon optimization with CG dimers reduction in the expression of G6Pase in mouse liver.

The G6pc wt sequence (SEQ ID NO: 2) was codon optimized using different methods. The G6pc co1 has the highest similarity with the wt sequence, and the lower CG dimers content. The G6pc co2 has the highest GC content and an increased CG dimers content compared to the G6pc co1. The G6pc co3 was less similar to the wt sequence, and has the highest CG dimers content (Table 2).

TABLE 2

Comparative analysis of the codon-optimized sequences.

| G6pc sequence | % vs wt | % vs co1 | % vs co2 | SD (score > 0.8)[a] | SA (score > 0.8)[a] | GC content (%)[b] | CG dimers | CpG islands[c] |
|---|---|---|---|---|---|---|---|---|
| wt | — | — | — | 0 | 4 | 52.16 | 24 | 0 |
| co1 | 97.49 | — | — | 1 | 3 | 50.74 | 0 | 0 |
| co2 | 81.88 | 83.41 | — | 1 | 3 | 59.22 | 11 | 0 |
| co3 | 75.02 | 74.84 | 76.49 | 0 | 1 | 48.46 | 48 | 0 |

Sequence analysis has been performed on the wild-type hG6pc sequence (wt) and on the three codon optimized (co1, co2 and co3).

[a] Splicing donor (SD) and splicing acceptor (SA) were predicted using an online tool (www.fruitfly.org) with a minimum score of 0.8.

[b] GC content was calculated using the online molecular biology tool (www.genscript.com).

[c] CpG islands smaller than 100 bp and with a GC content threshold of 60% were predicted with the online tool MethPrimerDB (www.urogene.org).

In the first experiment we produced three AAV8 vectors, expressing the following transgenes under the control of the hAAT promoter:

hG6pc: human G6pc gene wt (SEQ ID NO: 2), hG6pc Co1: human G6pc gene codon optimized (SEQ ID NO: 45), and hG6pc Co2: human G6pc gene codon optimized (SEQ ID NO: 46).

We then tested the three AAV8 vectors in a liver-specific G6pc knockout mouse model (L.G6pc$^{-/-}$, [13]), i.e. GSD-Ia mice at the dose of $1\times10^{12}$ vg/kg. As a positive control, WT mice (L.G6pc$^{+/+}$) were infused with PBS. Fifteen days after vector infusion, G6Pase activity was assessed in liver. The three AAV8 vector-injected groups showed supra-physiological G6Pase activity with levels higher than those measured in wild-type animals (FIG. 6A). Importantly, the AAV8 vector expressing hG6pc Co1 showed significantly increased levels of G6Pase activity when compared to the same vector expressing hG6pc Co2 (FIG. 6A).

For the second experiment we produced two AAV9 vectors, expressing the following transgenes under the control of the hAAT promoter:

hG6pc: human G6pc gene wt (SEQ ID NO: 2), hG6pc Co3: human G6pc gene codon optimized (SEQ ID NO: 3).

We then tested the two AAV9 vectors in a liver-specific G6pc knockout mouse model (L.G6pc$^{-/-}$, [13]), i.e. GSD-Ia mice at the dose of $1\times10^{11}$ vg/mouse. As a positive control, WT mice (L.G6pc$^{+/+}$) were infused with PBS. Fifteen days after vector infusion, G6Pase activity was assessed in liver. Importantly, only the group of animals injected with the AAV9 vector bearing the hG6pc wild-type sequence showed supra-physiological G6Pase activity with levels higher than those measured in wild-type animals (FIG. 6B). Animals injected with the AAV9 vector expressing hG6pc Co3 showed a tendency to a decreased G6Pase activity when compared to animals injected with the AAV9 vector expressing the wild-type version of hG6pc (p=0.06, FIG. 6B).

References Cited Under the Form "[Reference Number]"

[1] Chandler et al., Vector design influences hepatic genotoxicity after, The Journal of Clinical Investigation, 2015

[2] Mates et al. Nat Genet. 2009 June; 41(6):753-61. doi: 10.1038/ng.343

[3] Ling et al., 2016 Jul. 18, Hum Gene Ther Methods.

[4] Vercauteren et al., 2016, Mol. Ther. Vol. 24(6), p. 1042

[5] Rosario et al., 2016, Mol Ther Methods Clin Dev. 3, p.16026

[6] Shen et al., 2007 Molecular Therapy, volume 15, issue 11, pages 1955-1962

[7] Tenney et al., Virology, volumes 454-455, April 2014, pages 227-236

[8] Bartel et al., Front. Microbiol., 4 Oct. 2011 https://doi.org/10.3389/fmicb.2011.00204

[9] Michelfelder et al. (PLoS ONE, 2009, 4, e5122

[10] Zhong et al., PNAS Jun. 3, 2008 105 (22) 7827-7832; https://doi.org/10.1073/pnas.0802866105

[11] Finet et al., Virology, 2018, 513, 43-51.

[12] McCarty et al., 2003 Gene Therapy Dec; 10(26):2112-8.

[13] Mutel et al., *Targeted deletion of liver glucose-6 phosphatase mimics glycogen storage disease type 1a including development of multiple adenomas*, Journal of Hepatology, 2011 March; 54(3):529-37. doi: 10.1016/j.jhep.2010.08.014. Epub 2010 Oct. 1.

[14] Gjorgjieva M. et al, *Dietary exacerbation of metabolic stress leads to accelerated hepatic carcinogenesis in glycogen storage disease type Ia*, J. Hepatol. 2018; November; 69(5):1074-1087. doi: 10.1016/j.jhep.2018.07.017. Epub 2018 Sep. 5.

[15] George L. et al, *Hemophilia B Gene Therapy with a High-Specific-Activity Factor IX Variant*. N Engl J Med. 2017 Dec. 7; 377(23):2215-2227. doi: 10.1056/NEJMoa1708538.

[16] Zhang L. et al, *An evolutionary approach to optimizing glucose-6-phosphatase-a enzymatic activity for gene therapy of glycogen storage disease type Ia*. J Inherit Metab Dis. 2019 May; 42(3):470-479. doi: 10.1002/jimd.12069. Epub 2019 Feb. 22

[17] Rohr et al., J. Virol. Methods, 2002, 106, 81-88)

Sequence listing

| SEQ ID NO: | Description | Sequence |
|---|---|---|
| 1 | hG6Pase-a wt (amino acid) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQVELVFYVLSFCKSAVVPLASVSVIPYCL<br>AQVLGQPHKKSL |
| 2 | hG6pc wt (nucleic acid) (Encoding SEQ ID NO: 1) | atggaggaaggaatgaatgttctccatgactttgggatccagtcaacacattacctccaggt<br>gaattaccaagactcccaggactggttcatcttggtgtccgtgatcgcagacctcaggaatg<br>ccttctacgtcctcttccccatctggttccatcttcaggaagctgtgggcattaaactcctttgg<br>gtagctgtgattggagactggctcaacctcgtctttaagtggattctctttggacagcgtcca<br>tactggtgggttttggatactgactactacagcaacacttccgtgcccctgataaagcagttc<br>cctgtaacctgtgagactggaccagggagcccctctggccatgccatgggcacagcaggt<br>gtatactacgtgatggtcacatctactctttccatctttcagggaaagataaagccgacctac<br>agatttcggtgcttgaatgtcattttgtggttgggattctgggctgtgcagctgaatgtctgtc<br>tgtcacgaatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg |

-continued

Sequence listing

| SEQ ID NO: | Description | Sequence |
|---|---|---|
| | | ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 3 | hG6pc co3 (nucleic acid) (Codon optimized - encoding SEQ ID NO: 1) - used in Example 5 | atggaggagggaatgaatgtgctgcacgacttcgggattcagtctacccactatctccaag<br>tcaattatcaagacagtcaagattggttcatcctcgtctccgttatagctgacctcaggaatg<br>ctttttatgtactgttcccaatatggtttcatctgcaagaagcagttggaattaaactgctgtg<br>ggtggccgtaatcggagactggttgaacctggtgttcaaatggatcctttttggtcagaggc<br>catattggtgggtcttggacaccgactattatagcaacacatctgtaccccctgataaagcaa<br>ttccctgtaacgtgtgaaactgggcctgggtcacccagtggacacgcgatggggactgcc<br>ggggtttactacgtaatggttactagcacgcttagcattttccagggcaagatcaaaccgac<br>ttatcgcttccgatgcctcaatgtgatcctctggctgggattctgggcggttcaactgaacgt<br>atgcctctcacggatttatctggctgcacatttcccgcatcaagtagtggctggtgtgttgtct<br>ggcatagcagtggctgaaacattctcacacattcattctatttacaacgcttcattgaaaaaa<br>tactttctgattacttttttttttcagctttgcaattggcttttacttgctgcttaaaggtcttggc<br>gtcgacctgctctggactcttgagaaagcgcaacgctggtgcgaacaacccgagtgggtc<br>cacatagatacgaccccgttcgcgtctcttctgaaaaatctcggtaccctcttcggactggga<br>cttgctttgaattcttcaatgtatcgggaatcctgcaagggcaaactgtccaagtggttgccc<br>tttcgcctttcaagcattgtcgcttcccttgtgctcctgcacgtcttcgactcactgaagccgcc<br>gagccaagtcgagctcgtgttttacgtgttgtctttctgtaaaagtgccgtcgtgccactcgc<br>cagtgtgagcgtgataccttattgcctcgcacaggtgcttgggcagcctcataagaagtctc<br>tgtaa |
| 4 | hG6pc mut (nucleic acid) (identical to SEQ ID NO: 2 except for a c > g mutation at position 893) (Encoding SEQ ID NO: 12) | atggaggaaggaatgaatgttctccatgactttgggatccagtcaacacattacctccaggt<br>gaattaccaagactcccaggactggttcatcttggtgtccgtgatcgcagacctcaggaatg<br>ccttctacgtcctcttccccatctggttccatcttcaggaagctgtgggcattaaactcctttgg<br>gtagctgtgattggagactggctcaacctcgtctttaagtggattctctttggacagcgtcca<br>tactggtgggttttggatactgactactacagcaacacttccgtgcccctgataaagcagttc<br>cctgtaacctgtgagactggaccagggagcccctctggccatgccatgggcacagcaggt<br>gtatactacgtgatggtcacatctactctttccatctttcagggaaagataaagccgacctac<br>agatttcggtgcttgaatgtcattttgtggttgggattctgggctgtgcagctgaatgtctgtc<br>tgtcacgaatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctgtattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 5 | hG6pc mut co (Nucleic acid) (Codon optimized - encoding SEQ ID NO: 12) | atggaggaaggaatgaatgttctccatgactttgggatccagtcaacacattacctccaggt<br>gaattaccaagactcccaggactggttcatcttggtgtccgtgatcgcagacctcaggaatg<br>ccttctacgtcctcttccccatctggttccatcttcaggaagctgtgggcattaaactcctttgg<br>gtagctgtgattggagactggctcaacctcgtctttaagtggattctctttggacagcgtcca<br>tactggtgggttttggatactgactactacagcaacacttccgtgcccctgataaagcagttc<br>cctgtaacctgtgagactggaccagggagcccctctggccatgccatgggcacagcaggt<br>gtatactacgtgatggtcacatctactctttccatctttcagggaaagataaagccgacctac<br>agatttcggtgcttgaatgtcattttgtggttgggattctgggctgtgcagctgaatgtctgtc<br>tgtcacgaatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctgtattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 6 | hGPE promoter (4 nucleotides difference to hGPE promoter in NG011808.1) | tggaggaagcagaaaggggctggcaggtggaaagatgaggaccagctcatcgtctcat<br>gactatgaggttgctctgatccagaggtgccccctgcctggtggcccaccgccaggaaga<br>ctcccactgtccctggatgcccagagtgggatgtcaactccatcacttatcaactccttatcc<br>ataggggtattcttcctgaggcgtctcagaaaacagggccctccccatatgctgaccacata<br>atagaacccctcccaactcagagaccctggctgctagctgccctggcatgacccagacagt<br>ggcctttgtatatgtttttagactcaccttgactcacctctgaccatagaaactctcatcccag<br>aggtcactgcaatagttactccacaacagaggcttatctgggtagagggaggctccctacc<br>tatggcccagcagccctgacagtgcagatcacatataccccacgccccagcactgcctgcc<br>acgcatgggcttactttacacccacccacagtcaccaacacattacctgctctccaaggtta<br>ggcgtggcaggagaagtttgcttggaccagcagaaaccatgcagtcaaggacaactgga<br>gtcagcatgggctgggtgcgagcccttggtggggtggggaggagactccaggtcatacct |

-continued

Sequence listing

| SEQ ID NO: | Description | Sequence |
|---|---|---|
| | | cctggaggatgttttaatcatttccagcatggaatgctgtcaacttttgccacagattcattag<br>ctctgagtttctttttctgtccccagctaccccttacatgtcaatatggacttaatgatgggaa<br>attcaggcaagtttttaaacattttattccccctggctcttatcctcaaaaaatgcatgaatttg<br>gaggcagtggctcatgcctgtaatcccaatgctttgctaggttgaggcgggaggatcactt<br>gaagccaggaatttgagaccagcctgggccgcatagtgagaccccgtttctacaaaaata<br>aataaataaataataaataatagtgatatgaagcatgattaaatagccctatttttaaaatg<br>catgagttcgttacctgattcattccctggttcctttcacagtcctccgtgacccaagtgttagg<br>gttttggtctctctactatttgtaggctgatatatagtatacacacacacacacacacacatat<br>acacacacacagtgtatcttgagctttcttttgtatatctacacacatatgtataagaaagctc<br>aagatatagaagcccttttttcaaaaataactgaaagtttcaaactctttaagtctccagttac<br>cattttgctggtattcttatttggaaccatacattcatcatattgttgcacagtaagactataca<br>ttcattattttgcttaaacgtatgagttaaaacacttggccaggcatggtggttcacacctgta<br>atcccagagctttgggaagccaagactggcagtactcttgagctcaggaattcaagacca<br>gcctgggcaacatggaaaaaccccatctctacaaaagatagaaaaattagccaggcatg<br>gtggcgtgtgcctgtggtcccagctactcaggaggctgaggtgggaggatcacattagcc<br>caggaggttgaggctgcagtgagccgtgattatgccactgcactccagcctgggagacag<br>agtgagaccctgtttcaaaaaaaagagagagaaaatttaaaaaagaaaacaacaccaa<br>gggctgtaactttaaggtcattaaatgaattaatcactgcattcaaaaacgattactttctgg<br>ccctaagagacatgaggccaataccaggaaggggttgatctcccaaaccagaggcag<br>accctagactctaatacagttaaggaaagaccagcaagatgatagtccccaatacaatag<br>aagttactatattttatttgttgtttttcttttgttttgttttgttttgttttgttttagagactgg<br>ggtcttgctcgattgcccaggctgtagtgcagcggtgggacaatagctcactgcagactcc<br>aactcctgggctcaagcaatcctcctgcctcagcctcctgaatagctgggactacaagggt<br>acaccatcacacacaccaaaacaatttttttaaatttttgtgtagaaacgagggtcttgctttgt<br>tgcccaggctggtctccaactcctggcttcaagggatcctcccacctcagcctcccaaattgc<br>tgggattacaggtgtgagccaccacaaccagccagaactttactaattttaaaattaagaa<br>cttaaaacttgaatagctagagcaccaagatttttctttgtccccaaataagtgcagttgcag<br>gcatagaaaatctgacatctttgcaagaatcatcgtggatgtagactctgtcctgtgtctctg<br>gcctggtttcggggaccaggagggcagacccttgcactgccaagaagcatgccaaagtta<br>atcattggccctgctgagtacatggccgatcaggctgtttttgtgtgcctgtttttctattttacg<br>taaatcaccctgaacatgtttgcatcaacctactggtgatgcacctttgatcaatacattttag<br>acaaacgtggtttttgagtccaaagatcagggctgggttgacctgaatactggatacaggg<br>catataaaacaggggcaaggcacagactc |
| 7 | hAAT promoter + ApoE enhancer | aggctcagaggcacacaggagtttctgggctcaccctgcccccttccaacccctcagttccc<br>atcctccagcagctgtttgtgtgctgcctctgaagtccacactgaacaaacttcagcctactc<br>atgtccctaaaatgggcaaacattgcaagcagcaaacagcaaacacacagccctccctgc<br>ctgctgaccttggagctggggcagaggtcagagacctctctgggcccatgccacctccaac<br>atccactcgaccccttggaatttcggtggagaggagcagaggttgtcctggcgtggtttag<br>gtagtgtgagaggggtacccggggatcttgctaccagtggaacagccactaaggattctg<br>cagtgagagcagagggccagctaagtggtactctcccagagactgtctgactcacgccac<br>cccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaat |
| 8 | hAAT promoter | gtacccggggatcttgctaccagtggaacagccactaaggattctgcagtgagagcagag<br>ggccagctaagtggtactctcccagagactgtctgactcacgccacccccctccaccttggac<br>acaggacgctgtggtttctgagccaggtacaatgactcctttcggtaagtgcagtggaagc<br>tgtacactgcccaggcaaagcgtccgggcagcgtaggcgggcgactcagatcccagcca<br>gtggacttagcccctgtttgctcctccgataactggggtgaccttggttaatattcaccagca<br>gcctcccccgttgcccctctggatccactgcttaaatacggacgaggacagggccctgtctc<br>ctcagcttcaggcaccaccactgacctgggacagtgaat |
| 9 | ApoE enhancer | aggctcagaggcacacaggagtttctgggctcaccctgcccccttccaacccctcagttccc<br>atcctccagcagctgtttgtgtgctgcctctgaagtccacactgaacaaacttcagcctactc<br>atgtccctaaaatgggcaaacattgcaagcagcaaacagcaaacacacagccctccctgc<br>ctgctgaccttggagctggggcagaggtcagagacctctctgggcccatgccacctccaac<br>atccactcgaccccttggaatttcggtggagaggagcagaggttgtcctggcgtggtttag<br>gtagtgtgagaggg |
| 10 | hGPE_HBB2_ hG6pc wt_bGH (expression cassette used in examples 1, 2 and 3) | tggaggaagcagaaaggggctggcaggtggaaagatgaggaccagctcatcgtctcat<br>gactatgaggttgctctgatccagaggtgcccccctgcctggtggcccaccgccaggaaga<br>ctcccactgtccctggatgcccagagtgggatgtcaactccatcacttatcaactccttatcc<br>ataggggtattcttcctgaggcgtctcagaaaacagggccctccccatatgctgaccacata<br>atagaacccctcccaactcagagaccctggctgctagctgccctggcatgacccagacagt<br>ggcctttgtatatgtttttagactcaccttgactcacctctgaccatagaaactctcatcccag<br>aggtcactgcaatagttactccacaacagaggcttatctgggtagagggaggctccctacc<br>tatggcccagcagccctgacagtgcagatcacatataccccacgccccagcactgcctgcc<br>acgcatgggcttactttacacccacccacagtcaccaacacattacctgctctccaaggtta<br>ggcgtggcaggagaagtttgcttggaccagcagaaaccatgcagtcaaggacaactgga<br>gtcagcatgggctgggtgcgagcccttggtgggggggaggagactccaggtcatacct<br>cctggaggatgttttaatcatttccagcatggaatgctgtcaacttttgccacagattcattag |

-continued

Sequence listing

| SEQ ID NO: | Description | Sequence |
| --- | --- | --- |
| | | ctctgagtttctttttctgtccccagctaccccttacatgtcaatatggacttaatgatgggaa<br>attcaggcaagtttttaaacattttattccccctggctcttatcctcaaaaaatgcatgaatttg<br>gaggcagtggctcatgcctgtaatcccaatgctttgctaggttgaggcgggaggatcactt<br>gaagccaggaatttgagaccagcctgggccgcatagtgagaccccgtttctacaaaaata<br>aataaataaataataaataatagtgatatgaagcatgattaaatagccctatttttaaaatg<br>catgagttcgttacctgattcattccctggttcctttcacagtcctccgtgacccaagtgttagg<br>gttttggtctctctactatttgtaggctgatatatagtatacacacacacacacacacacatat<br>acacacacacagtgtatcttgagctttcttttgtatatctacacacatatgtataagaaagctc<br>aagatatagaagcccttttttcaaaaataactgaaagtttcaaactctttaagtctccagttac<br>cattttgctggtattcttatttggaaccatacattcatcatattgttgcacagtaagactataca<br>ttcattattttgcttaaacgtatgagttaaaacacttggccaggcatggtggttcacacctgta<br>atcccagagctttgggaagccaagactggcagtactcttgagctcaggaattcaagacca<br>gcctgggcaacatggaaaaaccccatctctacaaaagatagaaaaattagccaggcatg<br>gtggcgtgtgcctgtggtcccagctactcaggaggctgaggtgggaggatcacattagcc<br>caggaggttgaggctgcagtgagccgtgattatgccactgcactccagcctgggagacag<br>agtgagaccctgtttcaaaaaaaagagagagaaaatttaaaaaagaaaacaacaccaa<br>gggctgtaactttaaggtcattaaatgaattaatcactgcattcaaaaacgattactttctgg<br>ccctaagagacatgaggccaataccaggaaggggggttgatctcccaaaccagaggcag<br>accctagactctaatacagttaaggaaagaccagcaagatgatagtccccaatacaatag<br>aagttactatatttatttgttgtttttcttttgttttgttttgttttgttttgttttagagactgg<br>ggtcttgctcgattgcccaggctgtagtgcagcggtgggacaatagctcactgcagactcc<br>aactcctgggctcaagcaatcctcctgcctcagcctcctgaatagctgggactacaagggt<br>acaccatcacacacaccaaaacaatttttttaaatttttgtgtagaaacgagggtcttgctttgt<br>tgcccaggctggtctccaactcctggcttcaagggatcctcccacctcagcctcccaaattgc<br>tgggattacaggtgtgagccaccacaaccagccagaactttactaattttaaaattaagaa<br>cttaaaacttgaatagctagagcaccaagatttttctttgtccccaaataagtgcagttgcag<br>gcatagaaaatctgacatctttgcaagaatcatcgtggatgtagactctgtcctgtgtctctg<br>gcctggtttcggggaccaggagggcagacccttgcactgccaagaagcatgccaaagtta<br>atcattggccctgctgagtacatggccgatcaggctgtttttgtgtgcctgtttttctattttacg<br>taaatcaccctgaacatgtttgcatcaacctactggtgatgcacctttgatcaatacattttag<br>acaaacgtggtttttgagtccaaagatcagggctgggttgacctgaatactggatacaggg<br>catataaaacaggggcaaggcacagactcgggacccttgatgttttctttccccttcttttcta<br>tggttaagttcatgtcataggaaggggagaagtaacagggtacacatattgaccaaatca<br>gggtaattttgcatttgtaattttaaaaaatgctttcttcttttaatatactttttttgtttatcttattt<br>ctaatactttccctaatctctttctttcagggcaatattgatacaatgtatcttgcctctttgcacc<br>attctaaagaataacagtgataatttctgggttaaggcaatagcaatatttctgcatataaat<br>atttctgcatataaattgtaactgatgtaagaggtttcatattgctaatagcagctacaatcca<br>gctaccattctgcttttattttctggttgggataaggctggattattctgagtccaagctaggc<br>ccttttgctaatcttgttcatacctcttatcttcctcccacagctcctgggcaacctgctggtctct<br>ctgctggcccatcactttggcaaagcacgcgtgccaccatggaggaaggaatgaatgttct<br>ccatgactttgggatccagtcaacacattacctccaggtgaattaccaagactcccaggact<br>ggttcatcttggtgtccgtgatcgcagacctcaggaatgccttctacgtcctcttccccatctg<br>gttccatcttcaggaagctgtgggcattaaactcctttgggtagctgtgattggagactggct<br>caacctcgtctttaagtggattctctttggacagcgtccatactggtgggttttggatactgac<br>tactacagcaacacttccgtgcccctgataaagcagttccctgtaacctgtgagactggacc<br>agggagcccctctggccatgccatgggcacagcaggtgtatactacgtgatggtcacatct<br>actctttccatctttcagggaaagataaagccgacctacagatttcggtgcttgaatgtcattt<br>tgtggttgggattctgggctgtgcagctgaatgtctgtctgtcacgaatctaccttgctgctca<br>ttttcctcatcaagttgttgctggagtcctgtcaggcattgctgttgcagaaactttcagccac<br>atccacagcatctataatgccagcctcaagaaatattttctcattaccttcttcctgttcagctt<br>cgccatcggattttatctgctgctcaagggactgggtgtagacctcctgtggactctggaga<br>aagcccagaggtggtgcgagcagccagaatgggtccacattgacaccacaccctttgcca<br>gcctcctcaagaacctgggcacgctctttggcctggggctggctctcaactccagcatgtac<br>agggagagctgcaaggggaaactcagcaagtggctcccattccgcctcagctctattgta<br>gcctccctcgtcctcctgcacgtctttgactccttgaaaccccccatcccaagtcgagctggtct<br>tctacgtcttgtccttctgcaagagtgcggtagtgcccctggcatccgtcagtgtcatcccta<br>ctgcctcgcccaggtcctgggccagccgcacaagaagtcgttgtaaagatctgaattcacc<br>gcgggtttaaactgtgccttctagttgccagccatctgttgtttgcccctcccccgtgccttcct<br>tgaccctggaaggtgccactcccactgtcctttcctaataaaatgaggaaattgcatcgcatt<br>gtctgagtaggtgtcattctattctggggggtggggtggggctagc |
| 11 | hAAT_HBB2_<br>hG6pc wt<br>(expression<br>cassette used<br>in examples<br>1, 2, 3 and 5) | ggatcaaggctcagaggcacacaggagtttctgggctcaccctgcccccttccaacccctc<br>agttcccatcctccagcagctgtttgtgtgctgcctctgaagtccacactgaacaaacttcag<br>cctactcatgtccctaaaatgggcaaacattgcaagcagcaaacagcaaacacacagccc<br>tccctgcctgctgaccttggagctggggcagaggtcagagacctctctgggcccatgccac<br>ctccaacatccactcgaccccttggaatttcggtggagaggagcagaggttgtcctggcgt<br>ggtttaggtagtgtgagaggggtacccggggatcttgctaccagtggaacagccactaag<br>gattctgcagtgagagcagagggccagctaagtggtactctcccagagactgtctgactca<br>cgccaccccctccaccttggacacaggacgctgtggtttctgagccaggtacaatgactcct<br>ttcggtaagtgcagtggaagctgtacactgcccaggcaaagcgtccgggcagcgtaggc<br>gggcgactcagatcccagccagtggacttagcccctgtttgctcctccgataactggggtg<br>accttggttaatattcaccagcagcctcccccgttgcccctctggatccactgcttaaatacg<br>gacgaggacagggccctgtctcctcagcttcaggcaccaccactgacctgggacagtgaa<br>tagatcctgagaacttcagggtgagtctatgggacccttgatgttttctttccccttcttttctat |

-continued

Sequence listing

| SEQ ID NO: | Description | Sequence |
|---|---|---|
| | | ggttaagttcatgtcataggaaggggagaagtaacagggtacacatattgaccaaatcag<br>ggtaattttgcatttgtaattttaaaaaatgctttcttcttttaatatactttttttgtttatcttatttc<br>taatactttccctaatctctttctttcagggcaatattgatacaatgtatcttgcctctttgcacca<br>ttctaaagaataacagtgataatttctgggttaaggcaatagcaatatttctgcatataaata<br>tttctgcatataaattgtaactgatgtaagaggtttcatattgctaatagcagctacaatccag<br>ctaccattctgcttttattttctggttgggataaggctggattattctgagtccaagctaggccc<br>ttttgctaatcttgttcatacctcttatcttcctcccacagctcctgggcaacctgctggtctctct<br>gctggcccatcactttggcaaagcacgcgtgccaccatggaggaaggaatgaatgttctcc<br>atgactttgggatccagtcaacacattacctccaggtgaattaccaagactcccaggactg<br>gttcatcttggtgtccgtgatcgcagacctcaggaatgccttctacgtcctcttccccatctgg<br>ttccatcttcaggaagctgtgggcattaaactcctttgggtagctgtgattggagactggctc<br>aacctcgtctttaagtggattctctttggacagcgtccatactggtgggttttggatactgact<br>actacagcaacacttccgtgcccctgataaagcagttccctgtaacctgtgagactggacca<br>gggagcccctctggccatgccatgggcacagcaggtgtatactacgtgatggtcacatcta<br>ctctttccatctttcagggaaagataaagccgacctacagatttcggtgcttgaatgtcatttt<br>gtggttgggattctgggctgtgcagctgaatgtctgtctgtcacgaatctaccttgctgctcat<br>tttcctcatcaagttgttgctggagtcctgtcaggcattgctgttgcagaaactttcagccaca<br>tccacagcatctataatgccagcctcaagaaatatttctcattaccttcttcctgttcagcttc<br>gccatcggattttatctgctgctcaagggactgggtgtagacctcctgtggactctggagaa<br>agcccagaggtggtgcgagcagccagaatgggtccacattgacaccacaccctttgccag<br>cctcctcaagaacctgggcacgctctttggcctggggctggctctcaactccagcatgtaca<br>gggagagctgcaaggggaaactcagcaagtggctcccattccgcctcagctctattgtag<br>cctccctcgtcctcctgcacgtctttgactccttgaaaccccccatcccaagtcgagctggtctt<br>ctacgtcttgtccttctgcaagagtgcggtagtgcccctggcatccgtcagtgtcatcccta<br>ctgcctcgcccaggtcctgggccagccgcacaagaagtcgttgtaaagatctgaattcacc<br>ccaccagtgcaggctgcctatcagaaagtggtggctggtgtggctaatgccctggcccaca<br>agtatcactaagctcgctttcttgctgtccaatttctattaaaggttcctttgttccctaagtcca<br>actactaaactgggggatattatgaagggccttgagcatctggattctgcctaataaaaaa<br>catttattttcattgcaatgatgtatttaaattatttctgaatattttactaaaaagggaatgtgg<br>gaggtcagtgcatttaaaacataaagaaatgaagagctagttcaaaccttgggaaaatac<br>actatatcttaaactccatgaaagaaggtgaggctgcaaacagctaatgcacattggcaac<br>agcccctgatgcctatgccttattcatccctcagaaaaggattcaagtagaggcttgatttgg<br>aggttaaagtttggctatgctgtattttacattacttattgttttagctgtcctcatgaatgtcttt<br>tcactacccatttgcttatcctgcatctctcagccttgactccactcagttctcttgcttagagat<br>accacctttccccctgaagtgttccttccatgttttacggcgagatggtttctcctcgcctggcca<br>ctcagccttagttgtctctgttgtcttatagaggtctacttgaagaaggaaaaacagggggc<br>atggtttgactgtcctgtgagcccttcttccctgcctcccccactcacagtgacccggaatccc<br>tcgacatggcag |
| 12 | hG6PC mut<br>(amino acid) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSCIVASLVLLHVFDSLKPPSQVELVFYVLSFCKSAVVPLASVSVIPYCL<br>AQVLGQPHKKSL |
| 13 | Nucleic acid<br>coding<br>modified<br>G6Pase-a<br>(R3K) | Atggagaaaggaatgaatgttctccatgactttgggatccagtcaacacattacctccaggt<br>gaattaccaagactcccaggactggttcatcttggtgtccgtgatcgcagacctcaggaatg<br>ccttctacgtcctcttccccatctggttccatcttcaggaagctgtgggcattaaactcctttgg<br>gtagctgtgattggagactggctcaacctcgtctttaagtggattctctttggacagcgtcca<br>tactggtgggttttggatactgactactacagcaacacttccgtgcccctgataaagcagttc<br>cctgtaacctgtgagactggaccagggagcccctctggccatgccatgggcacagcaggt<br>gtatactacgtgatggtcacatctactctttccatctttcagggaaagataaagccgacctac<br>agatttcggtgcttgaatgtcattttgtggttgggattctgggctgtgcagctgaatgtctgtc<br>tgtcacgaatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 14 | Nucleic acid<br>coding<br>modified<br>G6Pase-a<br>(Q54R) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcgtgaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta |

-continued

Sequence listing

| SEQ ID NO: | Description | Sequence |
| --- | --- | --- |
| | | cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 15 | Nucleic acid coding modified G6Pase-a (Q139R) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcggggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 16 | Nucleic acid coding modified G6Pase-a (I142K) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagaaaaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 17 | Nucleic acid coding modified G6Pase-a (S196R) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttccgccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |

-continued

| Sequence listing | | |
|---|---|---|
| SEQ ID NO: | Description | Sequence |
| 18 | Nucleic acid coding modified G6Pase-a (H199Q) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccagagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 19 | Nucleic acid coding modified G6Pase-a (Q242R) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagccaggaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 20 | Nucleic acid coding modified G6Pase-a (Q247R) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcggccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 21 | Nucleic acid coding modified G6Pase-a (L292F) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggttc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct |

-continued

Sequence listing

| SEQ ID NO: | Description | Sequence |
|---|---|---|
| | | ggcatccgtcagtgtcatcccctactgcctcgcccaggtcctgggccagccgcacaagaag<br>tcgttgtaa |
| 22 | Nucleic acid coding modified G6Pase-a (S298C) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctgtattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 23 | Nucleic acid coding modified G6Pase-a (A301V) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagtgtccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 24 | Nucleic acid coding modified G6Pase-a (V318T) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaaactgagctggtcttctacgtcttgtccttctgcaagagtgcggtagtgcccct<br>ggcatccgtcagtgtcatcccctactgcctcgcccaggtcctgggccagccgcacaagaag<br>tcgttgtaa |
| 25 | Nucleic acid coding modified G6Pase-a (V324T) | atggaggaaggaatgaatgttctccatgactttgggatccagtcaacacattacctccaggt<br>gaattaccaagactcccaggactggttcatcttggtgtccgtgatcgcagacctcaggaatg<br>ccttctacgtcctcttccccatctggttccatcttcaggaagctgtgggcattaaactcctttgg<br>gtagctgtgattggagactggctcaacctcgtctttaagtggattctctttggacagcgtcca<br>tactggtgggttttggatactgactactacagcaacacttccgtgcccctgataaagcagttc<br>cctgtaacctgtgagactggaccagggagcccctctggccatgccatgggcacagcaggt<br>gtatactacgtgatggtcacatctactctttccatctttcagggaaagataaagccgacctac<br>agatttcggtgcttgaatgtcattttgtggttgggattctgggctgtgcagctgaatgtctgtc<br>tgtcacgaatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc |

-continued

Sequence listing

| SEQ ID NO: | Description | Sequence |
|---|---|---|
| | | ccattccgcctcagctctattgtagcctccctcgtcctcctgcacgtctttgactccttgaaacc<br>cccatcccaagtcgagctggtcttctacaccttgtccttctgcaagagtgcggtagtgcccct<br>ggcatccgtcagtgtcatcccctactgcctcgcccaggtcctgggccagccgcacaagaag<br>tcgttgtaa |
| 26 | Nucleic acid coding modified G6Pase-a (V332A) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggcagtgcccct<br>ggcatccgtcagtgtcatcccctactgcctcgcccaggtcctgggccagccgcacaagaag<br>tcgttgtaa |
| 27 | Nucleic acid coding modified G6Pase-a (Q347R) | Atggaggaaggaatgaatgttctccatgactttgggatccagtcaacacattacctccagg<br>tgaattaccaagactcccaggactggttcatcttggtgtccgtgatcgcagacctcaggaat<br>gccttctacgtcctcttccccatctggttccatcttcaggaagctgtgggcattaaactcctttg<br>ggtagctgtgattggagactggctcaacctcgtctttaagtggattctctttggacagcgtcc<br>atactggtgggttttggatactgactactacagcaacacttccgtgcccctgataaagcagtt<br>ccctgtaacctgtgagactggaccagggagcccctctggccatgccatgggcacagcagg<br>tgtatactacgtgatggtcacatctactctttccatctttcagggaaagataaagccgaccta<br>cagatttcggtgcttgaatgtcattttgtggttgggattctgggctgtgcagctgaatgtctgt<br>ctgtcacgaatctaccttgctgctcattttcctcatcaagttgttgctggagtcctgtcaggcat<br>tgctgttgcagaaactttcagccacatccacagcatctataatgccagcctcaagaaatattt<br>tctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccgggtcctgggccagccgcacaagaag<br>tcgttgtaa |
| 28 | Nucleic acid coding modified G6Pase-a (L349F) | atggaggaaggaatgaatgttctccatgactttgggatccagtcaacacattacctccaggt<br>gaattaccaagactcccaggactggttcatcttggtgtccgtgatcgcagacctcaggaatg<br>ccttctacgtcctcttccccatctggttccatcttcaggaagctgtgggcattaaactcctttgg<br>gtagctgtgattggagactggctcaacctcgtctttaagtggattctctttggacagcgtcca<br>tactggtgggttttggatactgactactacagcaacacttccgtgcccctgataaagcagttc<br>cctgtaacctgtgagactggaccagggagcccctctggccatgccatgggcacagcaggt<br>gtatactacgtgatggtcacatctactctttccatctttcagggaaagataaagccgacctac<br>agatttcggtgcttgaatgtcattttgtggttgggattctgggctgtgcagctgaatgtctgtc<br>tgtcacgaatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagcttcgccatcggattttatctgctgctcaagggactgggtgt<br>agacctcctgtggactctggagaaagcccagaggtggtgcgagcagccagaatgggtcc<br>acattgacaccacaccctttgccagcctcctcaagaacctgggcacgctctttggcctgggg<br>ctggctctcaactccagcatgtacagggagagctgcaaggggaaactcagcaagtggctc<br>ccattccgcctcagctctattgtagcctccctcgtcctcctgcacgtctttgactccttgaaacc<br>cccatcccaagtcgagctggtcttctacgtcttgtccttctgcaagagtgcggtagtgcccct<br>ggcatccgtcagtgtcatcccctactgcctcgcccaggtcttcggccagccgcacaagaag<br>tcgttgtaa |
| 29 | Modified G6Pase-a (R3K) | MEKGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQVELVFYVLSFCKSAVVPLASVSVIPYCL<br>AQVLGQPHKKSL |

-continued

Sequence listing

| SEQ ID NO: | Description | Sequence |
|---|---|---|
| 30 | Modified G6Pase-a (Q54R) | MEEGMNVLHDFGIQSTHYLQVNYQDSQDWFILVSVIADLRNAFYVLFP IWFHLREAVGIKLLWVAVIGDWLNLVFKWILFGQRPYWWVLDTDYYS NTSVPLIKQFPVTCETGPGSPSGHAMGTAGVYYVMVTSTLSIFQGKIKP TYRFRCLNVILWLGFWAVQLNVCLSRIYLAAHFPHQVVAGVLSGIAVAE TFSHIHSIYNASLKKYFLITFFLFSFAIGFYLLLKGLGVDLLWTLEKAQRW CEQPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 31 | Modified G6Pase-a (Q139R) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFRGKIKP TYRFRCLNVILWLGFWAVQLNVCLSRIYLAAHFPHQVVAGVLSGIAVAE TFSHIHSIYNASLKKYFLITFFLFSFAIGFYLLLKGLGVDLLWTLEKAQRW CEQPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 32 | Modified G6Pase-a (I142K) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFQGKKKP TYRFRCLNVILWLGFWAVQLNVCLSRIYLAAHFPHQVVAGVLSGIAVAE TFSHIHSIYNASLKKYFLITFFLFSFAIGFYLLLKGLGVDLLWTLEKAQRW CEQPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 33 | Modified G6Pase-a (S196R) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFQGKIKP TYRFRCLNVILWLGFWAVQLNVCLSRIYLAAHFPHQVVAGVLSGIAVAE TFRHIHSIYNASLKKYFLITFFLFSFAIGFYLLLKGLGVDLLWTLEKAQRW CEQPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 34 | Modified G6Pase-a (H199Q) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFQGKIKP TYRFRCLNVILWLGFWAVQLNVCLSRIYLAAHFPHQVVAGVLSGIAVAE TFSHIQSIYNASLKKYFLITFFLFSFAIGFYLLLKGLGVDLLWTLEKAQRW CEQPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 35 | Modified G6Pase-a (Q242R) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFQGKIKP TYRFRCLNVILWLGFWAVQLNVCLSRIYLAAHFPHQVVAGVLSGIAVAE TFSHIHSIYNASLKKYFLITFFLFSFAIGFYLLLKGLGVDLLWTLEKARRW CEQPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 36 | Modified G6Pase-a (Q247R) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFQGKIKP TYRFRCLNVILWLGFWAVQLNVCLSRIYLAAHFPHQVVAGVLSGIAVAE TFSHIHSIYNASLKKYFLITFFLFSFAIGFYLLLKGLGVDLLWTLEKAQRW CERPEWVHIDTTPFASLLKNLGTLFGLGLALNSSMYRESCKGKLSKWLP FRLSSIVASLVLLHVFDSLKPPSQVELVFYVLSFCKSAVVPLASVSVIPYCL AQVLGQPHKKSL |
| 37 | Modified G6Pase-a (L292F) | MEEGMNVLHDFGIQSTHYLQVNYQDSQDWFILVSVIADLRNAFYVLFP IWFHLQEAVGIKLLWVAVIGDWLNLVFKWILFGQRPYWWVLDTDYYS NTSVPLIKQFPVTCETGPGSPSGHAMGTAGVYYVMVTSTLSIFQGKIKP TYRFRCLNVILWLGFWAVQLNVCLSRIYLAAHFPHQVVAGVLSGIAVAE TFSHIHSIYNASLKKYFLITFFLFSFAIGFYLLLKGLGVDLLWTLEKAQRW CEQPEWVHIDTTPFASLLKNLGTLFGLGLALNSSMYRESCKGKLSKWFP FRLSSIVASLVLLHVFDSLKPPSQVELVFYVLSFCKSAVVPLASVSVIPYCL AQVLGQPHKKSL |

-continued

Sequence listing

| SEQ ID NO: | Description | Sequence |
|---|---|---|
| 38 | Modified G6Pase-a (S298C) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSCIVASLVLLHVFDSLKPPSQVELVFYVLSFCKSAVVPLASVSVIPYCL<br>AQVLGQPHKKSL |
| 39 | Modified G6Pase-a (A301V) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVVSLVLLHVFDSLKPPSQVELVFYVLSFCKSAVVPLASVSVIPYCL<br>AQVLGQPHKKSL |
| 40 | Modified G6Pase-a (V318T) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQTELVFYVLSFCKSAVVPLASVSVIPYCL<br>AQVLGQPHKKSL |
| 41 | Modified G6Pase-a (V324T) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQVELVFYTLSFCKSAVVPLASVSVIPYCL<br>AQVLGQPHKKSL |
| 42 | Modified G6Pase-a (V332A) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQVELVFYVLSFCKSAAVPLASVSVIPYCL<br>AQVLGQPHKKSL |
| 43 | Modified G6Pase-a (Q347R) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQVELVFYVLSFCKSAVVPLASVSVIPYCL<br>ARVLGQPHKKSL |
| 44 | Modified G6Pase-a (L349F) | MEEGMNVLHDFGIQSTHYLQVNYQDSQDWFILVSVIADLRNAFYVLFP<br>IWFHLQEAVGIKLLWVAVIGDWLNLVFKWILFGQRPYWWVLDTDYYS<br>NTSVPLIKQFPVTCETGPGSPSGHAMGTAGVYYVMVTSTLSIFQGKIKP<br>TYRFRCLNVILWLGFWAVQLNVCLSRIYLAAHFPHQVVAGVLSGIAVAE<br>TFSHIHSIYNASLKKYFLITFFLFSFAIGFYLLLKGLGVDLLWTLEKAQRW<br>CEQPEWVHIDTTPFASLLKNLGTLFGLGLALNSSMYRESCKGKLSKWLP<br>FRLSSIVASLVLLHVFDSLKPPSQVELVFYVLSFCKSAVVPLASVSVIPYCL<br>AQVFGQPHKKSL |
| 45 | Codon optimised G6pc (co1) - used in example 5 | atggaggaaggaatgaatgttctccatgactttgggatccagtcaacacattacctccaggt<br>gaattaccaagactcccaggactggttcatcttggtgtctgtgattgcagacctcaggaatg<br>ccttctatgtcctcttccccatctggttccatcttcaggaagctgtgggcattaaactcctttgg<br>gtagctgtgattggagactggctcaacctggtctttaagtggattctctttggacagaggcc<br>atactggtgggttttggatactgactactacagcaacacttctgtgcccctgataaagcagtt<br>ccctgtaacctgtgagactggaccagggagcccctctggccatgccatgggcacagcagg<br>tgtatactatgtgatggtcacatctactctttccatctttcagggaaagataaagcccacctac<br>agatttaggtgcttgaatgtcattttgtggttgggattctgggctgtgcagctgaatgtctgtc<br>tgtcaaggatctaccttgctgctcattttcctcatcaagttgttgctggagtcctgtcaggcatt<br>gctgttgcagaaactttcagccacatccacagcatctataatgccagcctcaagaatatttt |

-continued

Sequence listing

| SEQ ID NO: | Description | Sequence |
|---|---|---|
| | | ctcattaccttcttcctgttcagctttgccattggattttatctgctgctcaagggactgggtgta<br>gacctcctgtggactctggagaaagcccagaggtggtgtgagcagccagaatgggtcca<br>cattgacaccacaccctttgccagcctcctcaagaacctgggcaccctctttggcctggggc<br>tggctctcaactccagcatgtacagggagagctgcaaggggaaactcagcaagtggctcc<br>cattcaggctcagctctattgtagcctccctggtcctcctgcatgtctttgactccttgaaaccc<br>ccatcccaagtggagctggtcttctatgtcttgtccttctgcaagagtgctgtagtgcccctgg<br>catctgtcagtgtcatcccctactgcctggcccaggtcctgggccagccccacaagaagtcc<br>ttgtaa |
| 46 | Codon optimised G6pc (co2) - used in example 5 | atggaggaggggatgaacgtgctgcacgactttgggatccagagcacccactacctgca<br>ggtgaactaccaggacagccaggactggtttatcctggtgtctgtgattgctgacctgagg<br>aacgccttctacgtgctgttccctatctggttccacctgcaggaggctgtggggatcaagct<br>gctgtgggtggctgtgattggggactggctgaacctggtgttcaagtggatcctgtttggcc<br>agaggccctactggtgggtgctggacacagactactacagcaacacctctgtgcccctgat<br>caagcagttccctgtgacctgtgagacaggccctggcagcccctctggccacgctatgggc<br>acagctggggtgtactacgtgatggtgaccagcaccctgtctatcttccagggcaagatca<br>agcccacctacaggttcaggtgcctgaacgtgatcctgtggctgggcttctgggctgtgca<br>gctgaacgtgtgcctgagcaggatctacctggctgcccacttcccccaccaggtggtggct<br>ggggtgctgtctgggattgctgtggctgagaccttcagccacatccactctatctacaacgc<br>cagcctgaagaagtacttcctgatcaccttcttcctgttcagctttgctattggcttctacctgct<br>gctgaagggcctggggggtggacctgctgtggaccctggagaaggcccagaggtggtgtg<br>agcagcctgagtgggtgcacattgacaccacccccttttgccagcctgctgaagaacctggg<br>caccctgtttggcctgggcctggccctgaacagctctatgtacagggagagctgcaaggg<br>caagctgagcaagtggctgcccttcaggctgagctctattgtggccagcctggtgctgctgc<br>acgtgtttgacagcctgaagcccccccagccaggtggagctggtgttctacgtgctgagcttc<br>tgcaagtctgctgtggtgcccctggcctctgtgtctgtgatcccctactgcctggcccaggtg<br>ctgggccagccccacaagaagagcctgtag |
| 47 | Codon optimised intron of the β-globin gene (HBB2 co) - used in examples 4 and 5 | gtacacatattgaccaaatcagggtaattttgcatttgtaattttaaaaaatgctttcttcttttta<br>atatactttttttgtttatcttatttctaatactttccctaatctctttctttcagggcaataatgatac<br>aatgtatcatgcctctttgcaccattctaaagaataacagtgataatttctgggttaaggcaa<br>tagcaatatttctgcatataaatatttctgcatataaattgtaactgatgtaagaggtttcatat<br>tgctaatagcagctacaatccagctaccattctgcttttattttctggttgggataaggctgga<br>ttattctgagtccaagctaggcccttttgctaatcttgttcatacctcttatcttcctcccacagct<br>cctgggcaacctgctggtctctctgctggcccatcactttggcaaag |
| 48 | hAAT_HBB2Co_ hG6pc wt co1 (expression cassette used in example 5) | aaggctcagaggcacacaggagtttctgggctcaccctgccccttccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>ccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatactttttttgtttatcttatttctaatact<br>ttccctaatctctttctttcagggcaataatgatacaatgtatcatgcctctttgcaccattctaa<br>agaataacagtgataatttctgggttaaggcaatagcaatatttctgcatataaatatttctg<br>catataaattgtaactgatgtaagaggtttcatattgctaatagcagctacaatccagctacc<br>attctgcttttattttctggttgggataaggctggattattctgagtccaagctaggcccttttg<br>ctaatcttgttcatacctcttatcttcctcccacagctcctgggcaacctgctggtctctctgctg<br>gcccatcactttggcaaagcacgcgtgccaccatggaggaaggaatgaatgttctccatg<br>actttgggatccagtcaacacattacctccaggtgaattaccaagactcccaggactggttc<br>atcttggtgtctgtgattgcagacctcaggaatgccttctatgtcctcttccccatctggttcca<br>tcttcaggaagctgtgggcattaaactcctttgggtagctgtgattggagactggctcaacct<br>ggtctttaagtggattctctttggacagaggccatactggtgggttttggatactgactacta<br>cagcaacacttctgtgcccctgataaagcagttccctgtaacctgtgagactggaccaggg<br>agcccctctggccatgccatgggcacagcaggtgtatactatgtgatggtcacatctactctt<br>tccatctttcagggaaagataaagcccacctacagatttaggtgcttgaatgtcattttgtgg<br>ttgggattctgggctgtgcagctgaatgtctgtctgtcaaggatctaccttgctgctcattttcc<br>tcatcaagttgttgctggagtcctgtcaggcattgctgttgcagaaactttcagccacatcca<br>cagcatctataatgccagcctcaagaaatatttctcattaccttcttcctgttcagctttgccat<br>tggattttatctgctgctcaagggactgggtgtagacctcctgtggactctggagaaagccc<br>agaggtggtgtgagcagccagaatgggtccacattgacaccacaccctttgccagcctcct<br>caagaacctgggcaccctctttggcctggggctggctctcaactccagcatgtacagggag<br>agctgcaaggggaaactcagcaagtggctcccattcaggctcagctctattgtagcctccct<br>ggtcctcctgcatgtctttgactccttgaaaccccatcccaagtggagctggtcttctatgtc<br>ttgtccttctgcaagagtgctgtagtgcccctggcatctgtcagtgtcatcccctactgcctgg |

-continued

Sequence listing

| SEQ ID NO: | Description | Sequence |
|---|---|---|
| | | cccaggtcctgggccagccccacaagaagtccttgtaactcgaggaattcaccccaccagt<br>gcaggctgcctatcagaaagtggtggctggtgtggctaatgccctggcccacaagtatcac<br>taagctcgctttcttgctgtccaatttctattaaaggttcctttgttccctaagtccaactactaa<br>actgggggatattatgaagggccttgagcatctggattctgcctaataaaaaacatttatttt<br>cattgcaatgatgtatttaaattatttctgaatattttactaaaaagggaatgtgggaggtca<br>gtgcatttaaaacataaagaaatgaagagctagttcaaaccttgggaaaatacactatatc<br>ttaaactccatgaaagaaggtgaggctgcaaacagctaatgcacattggcaacagcccct<br>gatgcctatgccttattcatccctcagaaaaggattcaagtagaggcttgatttggaggtta<br>aagttttgctatgctgtattttacattacttattgttttagctgtcctcatgaatgtcttttcactac<br>ccatttgcttatcctgcatctctcagccttgactccactcagttctcttgcttagagataccacct<br>ttcccctgaagtgttccttccatgttttacggcgagatggtttctcctcgcctggccactcagcc<br>ttagttgtctctgttgtcttatagaggtctacttgaagaaggaaaaacagggggcatggttt<br>gactgtcctgtgagcccttcttccctgcctcccccactcacagtgacccggaatc |
| 49 | hAAT_HBB2Co_<br>hG6pc wt<br>co2<br>(expression<br>cassette used<br>in example 5) | aaggctcagaggcacacaggagtttctgggctcaccctgccccttccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>ccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatacttttttgtttatcttatttctaatact<br>ttccctaatctctttctttcagggcaataatgatacaatgtatcatgcctctttgcaccattctaa<br>agaataacagtgataatttctgggttaaggcaatagcaatatttctgcatataaatatttctg<br>catataaattgtaactgatgtaagaggtttcatattgctaatagcagctacaatccagctacc<br>attctgcttttattttctggttgggataaggctggattattctgagtccaagctaggcccttttg<br>ctaatcttgttcatacctcttatcttcctcccacagctcctgggcaacctgctggtctctctgctg<br>gcccatcactttggcaaagcacgcgtgccaccatggaggaggggatgaacgtgctgcac<br>gactttgggatccagagcacccactacctgcaggtgaactaccaggacagccaggactgg<br>tttatcctggtgtctgtgattgctgacctgaggaacgccttctacgtgctgttccctatctggtt<br>ccacctgcaggaggctgtggggatcaagctgctgtgggtggctgtgattggggactggct<br>gaacctggtgttcaagtggatcctgtttggccagaggccctactggtgggtgctggacaca<br>gactactacagcaacacctctgtgcccctgatcaagcagttccctgtgacctgtgagacag<br>gccctggcagcccctctggccacgctatgggcacagctggggtgtactacgtgatggtgac<br>cagcaccctgtctatcttccagggcaagatcaagcccacctacaggttcaggtgcctgaac<br>gtgatcctgtggctgggcttctgggctgtgcagctgaacgtgtgcctgagcaggatctacct<br>ggctgcccacttcccccaccaggtggtggctggggtgctgtctgggattgctgtggctgag<br>accttcagccacatccactctatctacaacgccagcctgaagaagtacttcctgatcaccttc<br>ttcctgttcagctttgctattggcttctacctgctgctgaagggcctgggggtggacctgctgt<br>ggaccctggagaaggcccagaggtggtgtgagcagcctgagtgggtgcacattgacacc<br>acccccttgccagcctgctgaagaacctgggcaccctgtttggcctgggcctggccctgaa<br>cagctctatgtacagggagagctgcaagggcaagctgagcaagtggctgcccttcaggct<br>gagctctattgtggccagcctggtgctgctgcacgtgtttgacagcctgaagcccccagcc<br>aggtggagctggtgttctacgtgctgagcttctgcaagtctgctgtggtgcccctggcctctg<br>tgtctgtgatcccctactgcctggcccaggtgctgggccagccccacaagaagagcctgta<br>gctcgaggaattcaccccaccagtgcaggctgcctatcagaaagtggtggctggtgtggct<br>aatgccctggcccacaagtatcactaagctcgctttcttgctgtccaatttctattaaaggttc<br>ctttgttccctaagtccaactactaaactgggggatattatgaagggccttgagcatctggat<br>tctgcctaataaaaaacatttattttcattgcaatgatgtatttaaattatttctgaatattttact<br>aaaaagggaatgtgggaggtcagtgcatttaaaacataaagaaatgaagagctagttca<br>aaccttgggaaaatacactatatcttaaactccatgaaagaaggtgaggctgcaaacagct<br>aatgcacattggcaacagcccctgatgcctatgccttattcatccctcagaaaaggattcaa<br>gtagaggcttgatttggaggttaaagttttgctatgctgtattttacattacttattgttttagct<br>gtcctcatgaatgtcttttcactacccatttgcttatcctgcatctctcagccttgactccactca<br>gttctcttgcttagagataccacctttcccctgaagtgttccttccatgttttacggcgagatgg<br>tttctcctcgcctggccactcagccttagttgtctctgttgtcttatagaggtctacttgaagaa<br>ggaaaaacagggggcatggtttgactgtcctgtgagcccttcttccctgcctcccccactca<br>cagtgacccggaatc |

-continued

Sequence listing

| SEQ ID NO: | Description | Sequence |
|---|---|---|
| 50 | hAAT_HBB2Co_<br>hG6pc wt<br>co3<br>(expression<br>cassette used<br>in example 5)<br>Comprising<br>SEQ ID NO: 3 | aaggctcagaggcacacaggagtttctgggctcaccctgccccttccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>cccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatacttttttgtttatcttatttctaatact<br>ttccctaatctctttctttcagggcaatattgatacaatgtatcttgcctctttgcaccattctaaa<br>gaataacagtgataatttctgggttaaggcaatagcaatatttctgcatataaatatttctgc<br>atataaattgtaactgatgtaagaggtttcatattgctaatagcagctacaatccagctacca<br>ttctgcttttattttctggttgggataaggctggattattctgagtccaagctaggcccttttgct<br>aatcttgttcatacctcttatcttcctcccacagctcctgggcaacctgctggtctctctgctgg<br>cccatcactttggcaaagcacgcgtgccaccatggaggagggaatgaatgtgctgcacga<br>cttcgggattcagtctacccactatctccaagtcaattatcaagacagtcaagattggttcat<br>cctcgtctccgttatagctgacctcaggaatgcttttatgtactgttcccaatatggtttcatct<br>gcaagaagcagttggaattaaactgctgtgggtggccgtaatcggagactggttgaacct<br>ggtgttcaaatggatcctttttggtcagaggccatattggtgggtcttggacaccgactatta<br>tagcaacacatctgtacccctgataaagcaattccctgtaacgtgtgaaactgggcctgggt<br>cacccagtggacacgcgatggggactgccggggtttactacgtaatggttactagcacgct<br>tagcattttccagggcaagatcaaaccgacttatcgcttccgatgcctcaatgtgatcctctg<br>gctgggattctgggcggttcaactgaacgtatgcctctcacggatttatctggctgcacattt<br>cccgcatcaagtagtggctggtgtgttgtctggcatagcagtggctgaaacattctcacaca<br>ttcattctatttacaacgcttcattgaaaaaatactttctgattactttttttcttttcagctttgca<br>attggcttttacttgctgcttaaaggtcttggcgtcgacctgctctggactcttgagaaagcgc<br>aacgctggtgcgaacaacccgagtgggtccacatagatacgaccccgttcgcgtctcttct<br>gaaaaatctcggtaccctcttcggactgggacttgctttgaattcttcaatgtatcgggaatc<br>ctgcaagggcaaactgtccaagtggttgccctttcgcctttcaagcattgtcgcttcccttgtg<br>ctcctgcacgtcttcgactcactgaagccgccgagccaagtcgagctcgtgttttacgtgttg<br>tctttctgtaaaagtgccgtcgtgccactcgccagtgtgagcgtgataccttattgcctcgca<br>caggtgcttgggcagcctcataagaagtctctgtaaagatctgaattcaccccaccagtgc<br>aggctgcctatcagaaagtggtggctggtgtggctaatgccctggcccacaagtatcacta<br>agctcgctttcttgctgtccaatttctattaaaggttcctttgttccctaagtccaactactaaac<br>tgggggatattatgaagggccttgagcatctggattctgcctaataaaaaacatttattttca<br>ttgcaatgatgtatttaaattatttctgaatattttactaaaaagggaatgtgggaggtcagt<br>gcatttaaaacataaagaaatgaagagctagttcaaaccttgggaaaatacactatatctt<br>aaactccatgaaagaaggtgaggctgcaaacagctaatgcacattggcaacagcccctg<br>atgcctatgccttattcatccctcagaaaaggattcaagtagaggcttgatttggaggttaaa<br>gtttggctatgctgtattttacattacttattgttttagctgtcctcatgaatgtcttttcactaccc<br>atttgcttatcctgcatctctcagccttgactccactcagttctcttgcttagagataccacctttt<br>cccctgaagtgttccttccatgttttacggcgagatggtttctcctcgcctggccactcagcctt<br>agttgtctctgttgtcttatagaggtctacttgaagaaggaaaaacagggggcatggtttga<br>ctgtcctgtgagcccttcttccctgcctcccccactcacagtgacccggaatc |
| 51 | hAAT_HBB2co_<br>hG6pc<br>mut<br>(expression<br>cassette)<br>Comprising<br>SEQ ID NO: 5 | aaggctcagaggcacacaggagtttctgggctcaccctgccccttccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>cccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatacttttttgtttatcttatttctaatact<br>ttccctaatctctttctttcagggcaataatgatacaatgtatcatgcctctttgcaccattctaa<br>agaataacagtgataatttctgggttaaggcaatagcaatatttctgcatataaatatttctg<br>catataaattgtaactgatgtaagaggtttcatattgctaatagcagctacaatccagctacc<br>attctgcttttattttctggttgggataaggctggattattctgagtccaagctaggcccttttg<br>ctaatcttgttcatacctcttatcttcctcccacagctcctgggcaacctgctggtctctctgctg<br>gcccatcactttggcaaagcacgcgtgccaccatggaggaaggaatgaatgttctccatg<br>actttgggatccagtcaacacattacctccaggtgaattaccaagactcccaggactggttc |

-continued

Sequence listing

| SEQ ID NO: | Description | Sequence |
| --- | --- | --- |
| | | atcttggtgtccgtgatcgcagacctcaggaatgccttctacgtcctcttccccatctggttcc<br>atcttcaggaagctgtgggcattaaactcctttgggtagctgtgattggagactggctcaac<br>ctcgtctttaagtggattctctttggacagcgtccatactggtgggttttggatactgactact<br>acagcaacacttccgtgcccctgataaagcagttccctgtaacctgtgagactggaccagg<br>gagcccctctggccatgccatgggcacagcaggtgtatactacgtgatggtcacatctactc<br>tttccatctttcagggaaagataaagccgacctacagatttcggtgcttgaatgtcattttgtg<br>gttgggattctgggctgtgcagctgaatgtctgtctgtcacgaatctaccttgctgctcattttc<br>ctcatcaagttgttgctggagtcctgtcaggcattgctgttgcagaaactttcagccacatcc<br>acagcatctataatgccagcctcaagaaatatttctcattaccttcttcctgttcagcttcgcc<br>atcggattttatctgctgctcaagggactgggtgtagacctcctgtggactctggagaaagc<br>ccagaggtggtgcgagcagccagaatgggtccacattgacaccacaccctttgccagcct<br>cctcaagaacctgggcacgctctttggcctggggctggctctcaactccagcatgtacagg<br>gagagctgcaaggggaaactcagcaagtggctcccattccgcctcagctGtattgtagcct<br>ccctcgtcctcctgcacgtctttgactccttgaaaccccccatcccaagtcgagctggtcttcta<br>cgtcttgtccttctgcaagagtgcggtagtgcccctggcatccgtcagtgtcatcccctactg<br>cctcgcccaggtcctgggccagccgcacaagaagtcgttgtaaCTCGAGgaattcaccc<br>caccagtgcaggctgcctatcagaaagtggtggctggtgtggctaatgccctggcccaca<br>agtatcactaagctcgctttcttgctgtccaatttctattaaaggttcctttgttccctaagtcca<br>actactaaactgggggatattatgaagggccttgagcatctggattctgcctaataaaaaa<br>catttattttcattgcaatgatgtatttaaattatttctgaatattttactaaaaagggaatgtgg<br>gaggtcagtgcatttaaaacataaagaaatgaagagctagttcaaaccttgggaaaatac<br>actatatcttaaactccatgaaagaaggtgaggctgcaaacagctaatgcacattggcaac<br>agcccctgatgcctatgccttattcatccctcagaaaaggattcaagtagaggcttgatttgg<br>aggttaaagttttgctatgctgtattttacattacttattgttttagctgtcctcatgaatgtctttt<br>cactacccatttgcttatcctgcatctctcagccttgactccactcagttctcttgcttagagata<br>ccacctttcccctgaagtgttccttccatgttttacggcgagatggtttctcctcgcctggccac<br>tcagccttagttgtctctgttgtcttatagaggtctacttgaagaaggaaaaacagggggca<br>tggtttgactgtcctgtgagcccttcttccctgcctcccccactcacagtgacccggaatc |
| 52 | Codon optimized hG6pc mut (co1) | atggaggaaggaatgaatgttctccatgactttgggatccagtcaacacattacctccaggt<br>gaattaccaagactcccaggactggttcatcttggtgtctgtgattgcagacctcaggaatg<br>ccttctatgtcctcttccccatctggttccatcttcaggaagctgtgggcattaaactcctttgg<br>gtagctgtgattggagactggctcaacctggtctttaagtggattctctttggacagaggcc<br>atactggtgggttttggatactgactactacagcaacacttctgtgcccctgataaagcagtt<br>ccctgtaacctgtgagactggaccagggagcccctctggccatgccatgggcacagcagg<br>tgtatactatgtgatggtcacatctactctttccatctttcagggaaagataaagcccacctac<br>agatttaggtgcttgaatgtcattttgtggttgggattctgggctgtgcagctgaatgtctgtc<br>tgtcaaggatctaccttgctgctcattttcctcatcaagttgttgctggagtcctgtcaggcatt<br>gctgttgcagaaactttcagccacatccacagcatctataatgccagcctcaagaaatatttt<br>ctcattaccttcttcctgttcagctttgccattggattttatctgctgctcaagggactgggtgta<br>gacctcctgtggactctggagaaagcccagaggtggtgtgagcagccagaatgggtcca<br>cattgacaccacaccctttgccagcctcctcaagaacctgggcaccctctttggcctggggc<br>tggctctcaactccagcatgtacagggagagctgcaaggggaaactcagcaagtggctcc<br>cattcaggctcagctgtattgtagcctccctggtcctcctgcatgtctttgactccttgaaaccc<br>ccatcccaagtggagctggtcttctatgtcttgtccttctgcaagagtgctgtagtgcccctgg<br>catctgtcagtgtcatcccctactgcctggcccaggtcctgggccagccccacaagaagtcc<br>ttgtaa |
| 53 | hAAT_HBB2co_ hG6pc mut co1 (expression cassette) | aaggctcagaggcacacaggagtttctgggctcaccctgccccettccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>cccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatacttttttgtttatcttatttctaatact<br>ttccctaatctctttctttcagggcaataatgatacaatgtatcatgcctctttgcaccattctaa<br>agaataacagtgataatttctgggttaaggcaatagcaatatttctgcatataaatatttctg<br>catataaattgtaactgatgtaagaggtttcatattgctaatagcagctacaatccagctacc<br>attctgcttttattttctggttgggataaggctggattattctgagtccaagctaggcccttttg<br>ctaatcttgttcatacctcttatcttcctcccacagctcctgggcaacctgctggtctctctgctg<br>gcccatcactttggcaaagcacgcgtgccaccatggaggaaggaatgaatgttctccatg<br>actttgggatccagtcaacacattacctccaggtgaattaccaagactcccaggactggttc<br>atcttggtgtctgtgattgcagacctcaggaatgccttctatgtcctcttccccatctggttcca<br>tcttcaggaagctgtgggcattaaactcctttgggtagctgtgattggagactggctcaacct<br>ggtctttaagtggattctctttggacagaggccatactggtgggttttggatactgactacta<br>cagcaacacttctgtgcccctgataaagcagttccctgtaacctgtgagactggaccaggg |

-continued

| SEQ ID NO: | Description | Sequence |
|---|---|---|
| | | agcccctctggccatgccatgggcacagcaggtgtatactatgtgatggtcacatctactctt<br>tccatctttcagggaaagataaagcccacctacagatttaggtgcttgaatgtcattttgtgg<br>ttgggattctgggctgtgcagctgaatgtctgtctgtcaaggatctaccttgctgctcattttcc<br>tcatcaagttgttgctggagtcctgtcaggcattgctgttgcagaaactttcagccacatcca<br>cagcatctataatgccagcctcaagaaatattttctcattaccttcttcctgttcagctttgccat<br>tggattttatctgctgctcaagggactgggtgtagacctcctgtggactctggagaaagccc<br>agaggtggtgtgagcagccagaatgggtccacattgacaccacaccctttgccagcctcct<br>caagaacctgggcaccctctttggcctggggctggctctcaactccagcatgtacagggag<br>agctgcaaggggaaactcagcaagtggctcccattcaggctcagctgtattgtagcctccc<br>tggtcctcctgcatgtctttgactccttgaaaccccccatcccaagtggagctggtcttctatgt<br>cttgtccttctgcaagagtgctgtagtgcccctggcatctgtcagtgtcatcccctactgcctg<br>gcccaggtcctgggccagccccacaagaagtccttgtaactcgaggaattcaccccacca<br>gtgcaggctgcctatcagaaagtggtggctggtgtggctaatgccctggcccacaagtatc<br>actaagctcgctttcttgctgtccaatttctattaaaggttcctttgttccctaagtccaactact<br>aaactgggggatattatgaagggccttgagcatctggattctgcctaataaaaaacatttat<br>tttcattgcaatgatgtatttaaattatttctgaatattttactaaaaagggaatgtgggaggt<br>cagtgcatttaaaacataaagaaatgaagagctagttcaaaccttgggaaaatacactata<br>tcttaaactccatgaaagaaggtgaggctgcaaacagctaatgcacattggcaacagccc<br>ctgatgcctatgccttattcatccctcagaaaaggattcaagtagaggcttgatttggaggtt<br>aaagttttgctatgctgtattttacattacttattgttttagctgtcctcatgaatgtcttttcacta<br>cccatttgcttatcctgcatctctcagccttgactccactcagttctcttgcttagagataccac<br>ctttcccctgaagtgttccttccatgttttacggcgagatggtttctcctcgcctggccactcag<br>ccttagttgtctctgttgtcttatagaggtctacttgaagaaggaaaaacaggggggcatggt<br>ttgactgtcctgtgagcccttcttccctgcctcccccactcacagtgacccggaatc |
| 54 | Codon optimized hG6pc mut (co2) | atggaggaggggatgaacgtgctgcacgactttgggatccagagcacccactacctgca<br>ggtgaactaccaggacagccaggactggtttatcctggtgtctgtgattgctgacctgagg<br>aacgccttctacgtgctgttccctatctggttccacctgcaggaggctgtggggatcaagct<br>gctgtgggtggctgtgattggggactggctgaacctggtgttcaagtggatcctgtttggcc<br>agaggccctactggtgggtgctggacacagactactacagcaacacctctgtgcccctgat<br>caagcagttccctgtgacctgtgagacaggccctggcagcccctctggccacgctatgggc<br>acagctggggtgtactacgtgatggtgaccagcaccctgtctatcttccagggcaagatca<br>agcccacctacaggttcaggtgcctgaacgtgatcctgtggctgggcttctgggctgtgca<br>gctgaacgtgtgcctgagcaggatctacctggctgcccacttcccccaccaggtggtggct<br>ggggtgctgtctgggattgctgtggctgagaccttcagccacatccactctatctacaacgc<br>cagcctgaagaagtacttcctgatcaccttcttcctgttcagctttgctattggcttctacctgct<br>gctgaagggcctgggggtggacctgctgtggaccctggagaaggcccagaggtggtgtg<br>agcagcctgagtgggtgcacattgacaccacccccttttgccagcctgctgaagaacctggg<br>caccctgtttggcctgggcctggccctgaacagctctatgtacagggagagctgcaaggg<br>caagctgagcaagtggctgcccttcaggctgagctgtattgtggccagcctggtgctgctg<br>cacgtgtttgacagcctgaagcccccccagccaggtggagctggtgttctacgtgctgagctt<br>ctgcaagtctgctgtggtgcccctggcctctgtgtctgtgatcccctactgcctggcccaggt<br>gctgggccagccccacaagaagagcctgtag |
| 55 | hAAT_HBB2co_ hG6pc mut co2 (expression cassette) | aaggctcagaggcacacaggagtttctgggctcaccctgccccc ttccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>cccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatacttttttgtttatcttatttctaatact<br>ttccctaatctctttctttcagggcaataatgatacaatgtatcatgcctctttgcaccattctaa<br>agaataacagtgataatttctgggttaaggcaatagcaatatttctgcatataaatatttctg<br>catataaattgtaactgatgtaagaggtttcatattgctaatagcagctacaatccagctacc<br>attctgcttttattttctggttgggataaggctggattattctgagtccaagctaggcccttttg<br>ctaatcttgttcatacctcttatcttcctcccacagctcctgggcaacctgctggtctctctgctg<br>gcccatcactttggcaaagcacgcgtgccaccatggaggaggggatgaacgtgctgcac<br>gactttgggatccagagcacccactacctgcaggtgaactaccaggacagccaggactgg<br>tttatcctggtgtctgtgattgctgacctgaggaacgccttctacgtgctgttccctatctggtt<br>ccacctgcaggaggctgtggggatcaagctgctgtgggtggctgtgattggggactggct<br>gaacctggtgttcaagtggatcctgtttggccagaggccctactggtgggtgctggacaca<br>gactactacagcaacacctctgtgcccctgatcaagcagttccctgtgacctgtgagacag<br>gccctggcagcccctctggccacgctatgggcacagctggggtgtactacgtgatggtgac<br>cagcaccctgtctatcttccagggcaagatcaagcccacctacaggttcaggtgcctgaac<br>gtgatcctgtggctgggcttctgggctgtgcagctgaacgtgtgcctgagcaggatctacct<br>ggctgcccacttcccccaccaggtggtggctggggtgctgtctgggattgctgtggctgag |

-continued

Sequence listing

| SEQ ID NO: | Description | Sequence |
|---|---|---|
| | | acctttcagccacatccactctatctacaacgccagcctgaagaagtacttcctgatcaccttc<br>ttcctgttcagctttgctattggcttctacctgctgctgaagggcctgggggtggacctgctgt<br>ggaccctggagaaggcccagaggtggtgtgagcagcctgagtgggtgcacattgacacc<br>acccccctttgccagcctgctgaagaacctgggcaccctgtttggcctgggcctggccctgaa<br>cagctctatgtacagggagagctgcaagggcaagctgagcaagtggctgcccttcaggct<br>gagctgtattgtggccagcctggtgctgctgcacgtgtttgacagcctgaagccccccagcc<br>aggtggagctggtgttctacgtgctgagcttctgcaagtctgctgtggtgcccctggcctctg<br>tgtctgtgatcccctactgcctggcccaggtgctgggccagccccacaagaagagcctgta<br>gctcgaggaattcaccccaccagtgcaggctgcctatcagaaagtggtggctggtgtggct<br>aatgccctggcccacaagtatcactaagctcgctttcttgctgtccaatttctattaaaggttc<br>ctttgttccctaagtccaactactaaactgggggatattatgaagggccttgagcatctggat<br>tctgcctaataaaaaacatttattttcattgcaatgatgtatttaaattatttctgaatattttact<br>aaaaagggaatgtgggaggtcagtgcatttaaaacataaagaaatgaagagctagttca<br>aaccttgggaaaatacactatatcttaaactccatgaaagaaggtgaggctgcaaacagct<br>aatgcacattggcaacagcccctgatgcctatgccttattcatccctcagaaaaggattcaa<br>gtagaggcttgatttggaggttaaagttttgctatgctgtattttacattacttattgttttagct<br>gtcctcatgaatgtcttttcactacccatttgcttatcctgcatctctcagccttgactccactca<br>gttctcttgcttagagataccacctttcccctgaagtgttccttccatgttttacggcgagatgg<br>tttctcctcgcctggccactcagccttagttgtctctgttgtcttatagaggtctacttgaagaa<br>ggaaaaacaggggggcatggtttgactgtcctgtgagcccttcttccctgcctcccccactca<br>cagtgacccggaatc |
| 56 | hAAT_HBB2co_<br>hG6pc wt<br>(expression<br>cassette used<br>in example 4<br>and 5)<br>Comprising<br>SEQ ID NO: 2 | aaggctcagaggcacacaggagtttctgggctcaccctgccccccttccaacccctcagttcc<br>catcctccagcagctgtttgtgtgctgcctctgaagtccacactgaacaaacttcagcctact<br>catgtccctaaaatgggcaaacattgcaagcagcaaacagcaaacacacagccctccctg<br>cctgctgaccttggagctggggcagaggtcagagacctctctgggcccatgccacctccaa<br>catccactcgaccccttggaatttcggtggagaggagcagaggttgtcctggcgtggttta<br>ggtagtgtgagaggggtacccggggatcttgctaccagtggaacagccactaaggattct<br>gcagtgagagcagagggccagctaagtggtactctcccagagactgtctgactcacgcca<br>cccccctccaccttggacacaggacgctgtggtttctgagccaggtacaatgactcctttcggt<br>aagtgcagtggaagctgtacactgcccaggcaaagcgtccgggcagcgtaggcgggcg<br>actcagatcccagccagtggacttagcccctgtttgctcctccgataactggggtgaccttg<br>gttaatattcaccagcagcctcccccgttgcccctctggatccactgcttaaatacggacga<br>ggacagggccctgtctcctcagcttcaggcaccaccactgacctgggacagtgaatagatc<br>ctgagaacttcagggtgagtctatgggacccttgatgttttctttccccttcttttctatggttaa<br>gttcatgtcataggaaggggagaagtaacagggtacacatattgaccaaatcagggtaat<br>tttgcatttgtaattttaaaaaatgctttcttcttttaatatactttttttgtttatcttatttctaatact<br>ttccctaatctctttctttcagggcaataatgatacaatgtatcatgcctctttgcaccattctaa<br>agaataacagtgataatttctgggttaaggcaatagcaatatttctgcatataaatatttctg<br>catataaattgtaactgatgtaagaggtttcatattgctaatagcagctacaatccagctacc<br>attctgcttttattttctggttgggataaggctggattattctgagtccaagctaggcccttttg<br>ctaatcttgttcatacctcttatcttcctcccacagctcctgggcaacctgctggtctctctgctg<br>gcccatcactttggcaaagcacgcgtgccaccatggaggaaggaatgaatgttctccatg<br>actttgggatccagtcaacacattacctccaggtgaattaccaagactcccaggactggttc<br>atcttggtgtccgtgatcgcagacctcaggaatgccttctacgtcctcttccccatctggttcc<br>atcttcaggaagctgtgggcattaaactcctttgggtagctgtgattggagactggctcaac<br>ctcgtctttaagtggattctctttggacagcgtccatactggtgggttttggatactgactact<br>acagcaacacttccgtgcccctgataaagcagttccctgtaacctgtgagactggaccagg<br>gagcccctctggccatgccatgggcacagcaggtgtatactacgtgatggtcacatctactc<br>tttccatctttcagggaaagataaagccgacctacagatttcggtgcttgaatgtcattttgtg<br>gttgggattctgggctgtgcagctgaatgtctgtctgtcacgaatctaccttgctgctcattttc<br>ctcatcaagttgttgctggagtcctgtcaggcattgctgttgcagaaactttcagccacatcc<br>acagcatctataatgccagcctcaagaaatattttctcattaccttcttcctgttcagcttcgcc<br>atcggattttatctgctgctcaagggactgggtgtagacctcctgtggactctggagaaagc<br>ccagaggtggtgcgagcagccagaatgggtccacattgacaccacacccctttgccagcct<br>cctcaagaacctgggcacgctctttggcctggggctggctctcaactccagcatgtacagg<br>gagagctgcaaggggaaactcagcaagtggctcccattccgcctcagctctattgtagcct<br>ccctcgtcctcctgcacgtctttgactccttgaaacccccatcccaagtcgagctggtcttcta<br>cgtcttgtccttctgcaagagtgcggtagtgcccctggcatccgtcagtgtcatcccctactg<br>cctcgcccaggtcctgggccagccgcacaagaagtcgttgtaaagatctgaattcacccca<br>ccagtgcaggctgcctatcagaaagtggtggctggtgtggctaatgccctggcccacaagt<br>atcactaagctcgctttcttgctgtccaatttctattaaaggttcctttgttccctaagtccaact<br>actaaactgggggatattatgaagggccttgagcatctggattctgcctaataaaaaacatt<br>tattttcattgcaatgatgtatttaaattatttctgaatattttactaaaaagggaatgtgggag<br>gtcagtgcatttaaaacataaagaaatgaagagctagttcaaaccttgggaaaatacacta<br>tatcttaaactccatgaaagaaggtgaggctgcaaacagctaatgcacattggcaacagc<br>ccctgatgcctatgccttattcatccctcagaaaaggattcaagtagaggcttgatttggag<br>gttaaagttttgctatgctgtattttacattacttattgttttagctgtcctcatgaatgtcttttca<br>ctacccatttgcttatcctgcatctctcagccttgactccactcagttctcttgcttagagatacc<br>acctttcccctgaagtgttccttccatgttttacggcgagatggtttctcctcgcctggccactc<br>agccttagttgtctctgttgtcttatagaggtctacttgaagaaggaaaaacaggggggcatg<br>gtttgactgtcctgtgagcccttcttccctgcctcccccactcacagtgacccggaatc |

-continued

Sequence listing

| SEQ ID NO: | Description | Sequence |
|---|---|---|
| 57 | Synthetic polynucleotide coding for AAVMut5 | atggctgccg atggttatct tccagattgg ctcgaggaca acctctctga<br>gggcattcgc gagtggtggg cgctgaaacc tggagccccg aagcccaaag<br>ccaaccagca aaagcaggacgacggccggg gtctggtgct tcctggctac<br>aagtacctcg gacccttcaa cggactcgac aagggggagc ccgtcaacgc<br>ggcggacgca gcggccctcg agcacgacaa ggcctacgac cagcagctgc<br>aggcgggtga caatccgtac ctgcggtata accacgccga cgccgagttt<br>caggagcgtc tgcaagaaga tacgtctttt gggggcaacc tcgggcgagc<br>agtcttccag gccaagaagc gggttctcga acctctcggt ctggttgagg<br>aaggcgctaa gacggctcct ggaaagaaga gaccggtaga gccatcaccc<br>cagcgttctc cagactcctc tacgggcatc ggcaagaaag gccaacagcc<br>cgccagaaaa agactcaatt ttggtcagac tggcgactca gagtcagttc<br>cagaccctca acctctcgga gaacctccag cagcgccctc tggtgtggga<br>cctaatacaa tggctgcagg cggtggcgca ccaatggcag acaataacga<br>aggcgccgac ggagtgggta gttcctcggg aaattggcat tgcgattcca<br>catggctggg cgacagagtc atcaccacca gcacccgaac ctgggccctg<br>cccacctaca acaaccacct ctacaagcaa atctccaacg ggacatcggg<br>aggagccacc aacgacaaca cctacttcgg ctacagcacc ccctgggggt<br>attttgactt taacagattc cactgccact tttcaccacg tgactggcag cgactcatca<br>acaacaactg gggattccgg cccaagagac tcagcttcaa gctcttcaac<br>atccaggtca aggaggtcac gcagaatgaa ggcaccaaga ccatcgccaa<br>taacctcacc agcaccatcc aggtgtttac ggactcggag taccagctgc<br>cgtacgttct cggctctgcc caccagggct gcctgcctcc gttcccggcg<br>gacgtgttca tgattcccca gtacggctac ctaacactca acaacggtag<br>tcaggccgtg ggacgctcct ccttctactg cctggaatac tttccttcgc agatgctgag<br>aaccggcaac aacttccagt ttacttacac cttcgaggac gtgcctttcc<br>acagcagcta cgcccacagc cagagcttgg accggctgat gaatcctctg<br>attgaccagt acctgtacta tctgaacaag acacaatcaa atagtggaac<br>tcttcagcag tctcggctac tgtttagtca agctggaccc accagcatgt ctcttcaagc<br>taaaaactgg ctgcctggac cttgctaccg ccaacaacgc gtctcaacga<br>caaccgggca aaacaacaat agcaactttg cctggactgc tgggaccaaa<br>taccatctga atggaagaaa ttcattggct aatcctggca tcgctatggc<br>aacacacaaa gacgacgagg agcgtttttt tcccagtaac gggatcctga<br>tttttggcaa acaaaatgct gccagagaca atgcggatta cagcgatgtc<br>atgctcacca gcgaggaaga aatcaaaacc actaaccctg tggctacaga<br>ggaatacggt atcgtggcag ataacttgca gcagcaaaac acggctcctc<br>aaattggaac tgtcaacagc caggggggcct tacccggtat ggtctggcag<br>aaccgggacg tgtacctgca gggtcccatc tgggccaaga ttcctcacac<br>ggacggcaac ttccacccgt ctccgctgat gggcggcttt ggcctgaaac<br>atcctccgcc tcagatcctg atcaagaaca cgcctgtacc tgcggatcct<br>ccgaccacct tcaaccagtc aaagctgaac tctttcatca cgcaatacag<br>caccggacag gtcagcgtgg aaattgaatg ggagctgcag aaggaaaaca<br>gcaagcgctg gaaccccgag atccagtaca cctccaacta ctacaaatct<br>acaagtgtgg actttgctgt taatacagaa ggcgtgtact ctgaaccccg<br>ccccattggc acccgttacc tcacccgtaa tctgtaa |
| 58 | AAVmut5 (amino acid) | MAADGYLPDWLEDNLSEGIREWWALKPGAPKPKANQQKQDDGRGLV<br>LPGYKYLGPFNGLDKGEPVNAADAAALEHDKAYDQQLQAGDNPYLRYN<br>HADAEFQERLQEDTSFGGNLGRAVFQAKKRVLEPLGLVEEGAKTAPGK<br>KRPVEPSPQRSPDSSTGIGKKGQQPARKRLNFGQTGDSESVPDPQPLG<br>EPPAAPSGVGPNTMAAGGGAPMADNNEGADGVGSSSGNWHCDSTWL<br>GDRVITTSTRTWALPTYNNHLYKQISNGTSGGATNDNTYFGYSTPWG<br>YFDFNRFHCHFSPRDWQRLINNNWGFRPKRLSFKLFNIQVKEVTQNEG<br>TKTIANNLTSTIQVFTDSEYQLPYVLGSAHQGCLPPFPADVFMIPQYGYL<br>TLNNGSQAVGRSSFYCLEYFPSQMLRTGNNFQFTYTFEDVPFHSSYAH<br>SQSLDRLMNPLIDQYLYYLNKTQSNSGTLQQSRLLFSQAGPTSMSLQA<br>KNWLPGPCYRQQRVSTTTGQNNNSNFAWTAGTKYHLNGRNSLANPGI<br>AMATHKDDEERFFPSNGILIFGKQNAARDNADYSDVMLTSEEEIKTTNP<br>VATEEYGIVADNLQQQNTAPQIGTVNSQGALPGMVWQNRDVYLQGPI<br>WAKIPHTDGNFHPSPLMGGFGLKHPPPQILIKNTPVPADPPTTFNQSKL<br>NSFITQYSTGQVSVEIEWELQKENSKRWNPEIQYTSNYYKSTSVDFAV<br>NTEGVYSEPRPIGTRYLTRNL |

The invention claimed is:

1. An adeno-associated virus (AAV) vector comprising a nucleic acid construct for the expression of a glucose-6-phosphatase-a (G6Pase-a) in a cell, the construct comprising a nucleic acid sequence encoding the G6Pase-a, wherein the nucleic acid sequence encoding the G6Pase-a is operably linked to a human alpha-1 antitrypsin (hAAT) promoter, wherein the nucleic acid sequence encoding the G6Pase-a is codon optimized by decreasing the content of GC and decreasing GC dimers in said nucleic acid sequence encoding the G6Pase-a.

2. The AAV vector according to claim 1, wherein the G6Pase-a has an amino acid sequence at least 90% identical to SEQ ID NO: 1.

3. The AAV vector according to claim 1, wherein the nucleic acid sequence encoding the G6Pase-a comprises a nucleotide sequence having at least 90% identity with SEQ ID NO: 2.

4. The AAV vector according to claim 1, wherein the hAAT promoter comprises a nucleotide sequence having at least 90% identity with SEQ ID NO: 8.

5. The AAV vector according to claim 1, wherein the hAAT promoter is preceded by an enhancer.

6. The AAV vector according to claim 1, wherein the nucleic acid construct comprises a nucleotide sequence having at least 90% identity with SEQ ID NO: 11, SEQ ID NO: 48, SEQ ID NO: 49, SEQ ID NO: 50, SEQ ID NO: 51, SEQ ID NO: 53, SEQ ID NO: 55, or SEQ ID NO: 56.

7. The AAV vector according to claim 1, wherein the nucleic acid construct comprises, in the 5' to 3' orientation:

(i) the hAAT promoter preceded by an enhancer;
(ii) optionally an intron;
(iii) the nucleic acid sequence encoding the G6Pase-a; and
(iv) a polyadenylation signal.

8. The AAV vector according to claim 1, wherein the cell is a liver cell, a kidney cell, or an intestine cell.

9. The AAV vector of claim 1, which is an AAV serotype 8 (AAV8) vector, an AAV9 vector, an AAVrh74 vector, an AAV218 vector, or an AAVmut5 vector.

10. A cell transformed with the AAV vector of claim 1.

11. The cell according to claim 10, which is a liver cell, an intestinal cell, or a kidney cell.

12. The AAV vector of claim 1, a cell transformed with said AAV vector, or a composition comprising said AAV vector or said cell, for use as a medicament.

13. The AAV vector according to claim 1, wherein the hAAT promoter is preceded by an ApoE enhancer or cis-regulatory modules (CRMs).

14. The AAV vector according to claim 1, wherein the hAAT promoter is preceded by an ApoE enhancer of SEQ ID NO: 9.

15. The AAV vector according to claim 1, wherein the nucleic acid construct comprises SEQ ID NO: 7.

16. The AAV vector according to claim 1, wherein the nucleic acid construct comprises a nucleotide sequence having at least 90% identity with SEQ ID NO: 48.

17. The AAV vector according to claim 1, wherein the nucleic acid construct comprises, in the 5' to 3' orientation:

(i) the hAAT promoter preceded by an ApoE enhancer or cis-regulatory modules (CRMs);

(ii) optionally an intron of a human β globin gene;

(iii) the nucleic acid sequence encoding the G6Pase-a; and (iv) a bovine growth hormone polyadenylation signal, a HBB2 polyadenylation signal, a SV40 polyadenylation signal, or another naturally occurring or artificial polyadenylation signal.

18. The AAV vector according to claim 1, wherein the nucleic acid construct comprises, in the 5' to 3' orientation:

(i) the hAAT promoter preceded by an ApoE enhancer of SEQ ID NO: 9;

(ii) optionally an intron of a human β globin gene of SEQ ID NO: 47;

(iii) the nucleic acid sequence encoding the G6Pase-a; and (iv) a bovine growth hormone polyadenylation signal, a HBB2 polyadenylation signal, a SV40 polyadenylation signal, or another naturally occurring or artificial polyadenylation signal.

19. The AAV vector according to claim 1, which is an AAV8 vector.

20. A composition comprising the AAV vector of claim 1, or a cell transformed with said AAV vector.

21. A method for treating glycogen storage disease (GSD), comprising administering to a subject the AAV vector of claim 1, a cell transformed with said AAV vector, or a composition comprising said AAV vector or said cell.

22. The method of claim 21, wherein the GSD is GSD-Ia.

* * * * *